United States Patent
Mingozzi et al.

(10) Patent No.: US 11,541,131 B2
(45) Date of Patent: Jan. 3, 2023

(54) TREATMENT OF GLYCOGEN STORAGE DISEASE III

(71) Applicants: GENETHON, Evry (FR); UNIVERSITE D'EVRY VAL D'ESSONNE, Evry (FR); INSTITUT NATIONAL DE LA SANTÉ ET DE LA RECHERCHE MÉDICALE, Paris (FR); SORBONNE UNIVERSITÉ, Paris (FR)

(72) Inventors: Federico Mingozzi, Paris (FR); Giuseppe Ronzitti, Fontainebleau (FR); Patrice Vidal, Ris-Orangis (FR)

(73) Assignees: GENETHON, Evry (FR); UNIVERSITE D'EVRY VAL D'ESSONNE, Evry (FR); INSITUT NATIONAL DE LA SANTE ET DE LA RECHERCHE MEDICALE, Paris (FR); SORBONNE UNIVERSITÉ, Paris (FR)

( * ) Notice: Subject to any disclaimer, the term of this patent is extended or adjusted under 35 U.S.C. 154(b) by 719 days.

(21) Appl. No.: 16/491,623

(22) PCT Filed: Mar. 9, 2018

(86) PCT No.: PCT/EP2018/055976
§ 371 (c)(1),
(2) Date: Sep. 6, 2019

(87) PCT Pub. No.: WO2018/162748
PCT Pub. Date: Sep. 13, 2018

(65) Prior Publication Data
US 2020/0289673 A1  Sep. 17, 2020

(30) Foreign Application Priority Data
Mar. 10, 2017 (EP) .................... 17305261

(51) Int. Cl.
| A61K 48/00 | (2006.01) |
| C07H 21/04 | (2006.01) |
| C12N 15/00 | (2006.01) |
| C12N 15/63 | (2006.01) |
| C12N 7/00  | (2006.01) |
| A61P 3/08  | (2006.01) |
| C12N 9/16  | (2006.01) |

(52) U.S. Cl.
CPC ...... *A61K 48/0066* (2013.01); *A61K 48/0033* (2013.01); *A61P 3/08* (2018.01); *C12N 7/00* (2013.01); *C12N 9/16* (2013.01); *C12Y 301/03001* (2013.01); *C12N 2750/14121* (2013.01); *C12N 2750/14132* (2013.01); *C12N 2750/14143* (2013.01); *C12N 2750/14145* (2013.01)

(58) Field of Classification Search
CPC .......... C12N 2750/14143; C12N 15/86; A61P 3/00; A61K 38/47
See application file for complete search history.

(56) References Cited

U.S. PATENT DOCUMENTS

2010/0003218 A1  1/2010  Duan et al.

FOREIGN PATENT DOCUMENTS

WO  WO 2014/170480  10/2014

OTHER PUBLICATIONS

Chamberlain, K. et al. "Expressing Transgenes That Exceed the Packaging Capacity of Adeno-Associated Virus Capsids" *Human Gene Therapy Methods*, 2016, pp. 1-12, vol. 27, No. 1.
Ghosh, A. et al. "A Hybrid Vector System Expands Adeno-associated Viral Vector Packaging Capacity in a Transgene-independent Manner" *Molecular Therapy*, Jan. 2008, pp. 124-130, vol. 16, No. 1.
Ghosh, A. et al. "Efficient Transgene Reconstitution with Hybrid Dual AAV Vectors Carrying the Minimized Bridging Sequences" *Human Gene Therapy*, Jan. 2011, pp. 77-83, vol. 22.
Hirsch, M. L. et al. "Delivering Transgenic DNA Exceeding the Carrying Capacity of AAV Vectors" *Methods Mol Biol.*, 2016, pp. 1-20, vol. 1382.
Sun, B. et al. "Preclinical Development of New Therapy for Glycogen Storage Diseases" *Curr Gene Ther.*, 2015, pp. 1-20, vol. 15, No. 4.
Vidal, P. et al. "Rescue of GSDIII Phenotype with Gene Transfer Requires Liver- and Muscle-Targeted GDE Expression" *Molecular Therapy*, Mar. 2018, pp. 890-901, vol. 26, No. 3.
Zhang, P. et al. "Immunodominant Liver-Specific Expression Suppresses Transgene-Directed Immune Responses in Murine Pompe Disease" *Human Gene Therapy*, May 2012, pp. 460-472, vol. 23, No. 5.
Written Opinion in International Application No. PCT/EP2018/055976, dated Jul. 3, 2018, pp. 1-6.

*Primary Examiner* — Barry A Chestnut
(74) *Attorney, Agent, or Firm* — Saliwanchik, Lloyd & Eisenschenk

(57) ABSTRACT

The present invention relates to vectors and compositions for the treatment of glycogen storage disease III.

Figure 1:
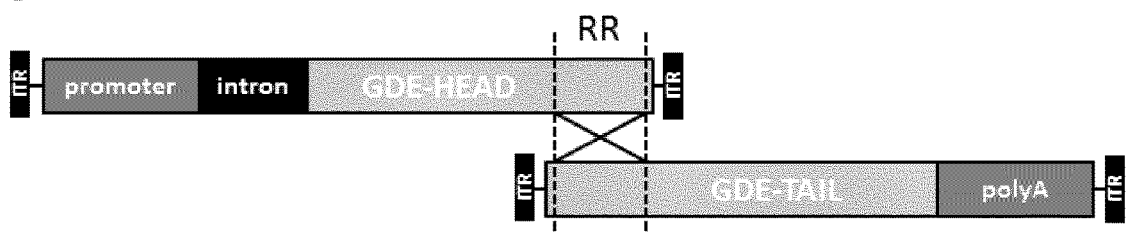
Figure 1:
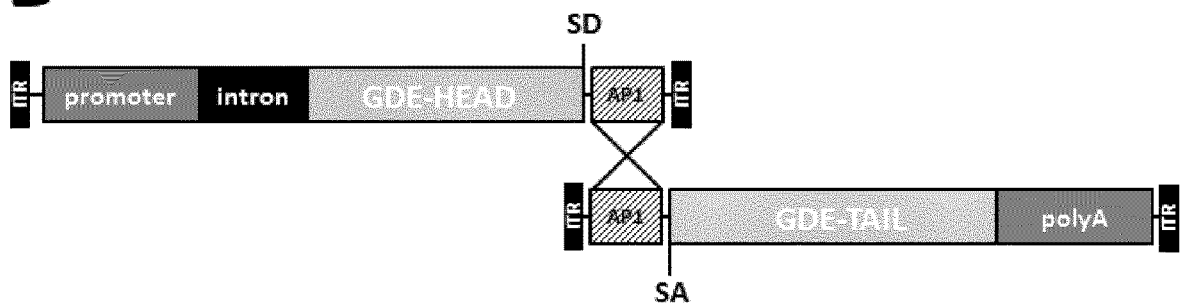

21 Claims, 6 Drawing Sheets
Specification includes a Sequence Listing.

TREATMENT OF GLYCOGEN STORAGE DISEASE III

CROSS-REFERENCE TO RELATED APPLICATION

This application is the U.S. national stage application of International Patent Application No. PCT/EP2018/055976, filed Mar. 9, 2018.

The Sequence Listing for this application is labeled "Seq-List.txt" which was created on Aug. 8, 2019 and is 77 KB. The entire content of the sequence listing is incorporated herein by reference in its entirety.

FIELD OF THE INVENTION

The present invention relates to the treatment of glycogen storage disease III (GSDIII).

BACKGROUND OF THE INVENTION

Genetic deficiency of glycogen debranching enzyme (GDE) causes an incomplete glycogenolysis in glycogen storage disease III (GSD III), resulting in accumulation of abnormal glycogen with short outer chain in various organs, mostly liver and muscle. The disease is characterized by hepatomegaly, hypoglycemia, short stature, variable myopathy and cardiomyopathy. Most patients have diseases involving both liver and muscle (type IIIa), while some patients (~15 percent) have only liver involvement (type IIIb). Liver symptoms normally occur in childhood. Liver cirrhosis and hepatocellular carcinoma have been reported in some cases (Chen et al., 2009, Scriver's Online Metabolic & Molecular Bases of inherited Disease, New York: McGraw-Hill; Kishnani et al., 2010, Genet Med 12, 446-463). Muscle weakness could be present during childhood. It becomes more prevalent in adults with onset in the third or fourth decade. There is significant morbidity from progressive muscle weakness and patients in later stages can become wheel chair bound. Patients can also develop cardiomyopathy. There is significant clinical variability in the severity of the symptoms that these patients develop. The progressive myopathy and/or cardiomyopathy and/or peripheral neuropathy are major causes of morbidity in adults (Kishnani et al., 2010, Genet Med 12, 446-463; Cornelio et al., 1984, Arch Neurol 41, 1027-1032; Coleman et al., 1992, Ann Intern Med 116, 896-900). Reports of possible neurological manifestations associated with the disease derive from clinicians working with GSDIII patients, who reported attention fluctuations, deficiencies in executive functions and impaired emotional skills (Michon et al., 2015, J Inherit Metab Dis, 38(3): 573-580). Accordingly, in the GDE-/- mouse model of the disease, an extensive accumulation of glycogen throughout the nervous system was documented (Pagliarani et al., 2014, Biochim Biophys Acta, 1842(11): 2318-2328; Liu et al., 2014, Mol Genet Metab, 111(4): 467-476) although a careful characterization of the phenotype associated with the accumulation of glycogen is still missing. Current treatment is symptomatic, and there is no effective therapy for the disease. Hypoglycemia can be controlled by frequent meals high in carbohydrates with cornstarch supplements or nocturnal gastric drip feedings. Patients with myopathy have been treated with a diet high in protein during the daytime plus overnight enteral infusion. In some patients transient improvement in symptoms has been documented, but there are no systemic studies or long-term data demonstrating that the high protein diet prevents or treats the progressive myopathy (Kishnani et al., 2010, Genet Med 12, 446-463). These approaches do little to alter the long term course and morbidity of these diseases.

Therefore, there is still a need for a long-term treatment of GSD III.

SUMMARY OF THE INVENTION

In a first aspect, the invention relates to a dual recombinant AAV vector system comprising two AAV vectors, wherein
  a first AAV vector comprises, between 5' and 3' AAV ITRs, a first nucleic acid sequence that encodes a N-terminal part of a glycogen debranching enzyme (GDE), and
  a second AAV vector comprises, between 5' and 3' AAV ITRs, a second nucleic acid sequence that encodes a C-terminal part of said GDE, and
  wherein the first and second nucleic acid sequences encoding said GDE comprise a polynucleotide region that permits the production of a full-length GDE protein, in particular a polynucleotide region that permits the production of a full-length nucleic acid sequence that encodes full-length GDE.

In a particular embodiment, said polynucleotide region may be a GDE polynucleotide sequence that overlaps between said first and second nucleic acid sequences. The length of said polynucleotide sequence that overlaps between said first and second nucleic acid sequences is between about 100 and about 4500 nucleotides. In a particular embodiment, the nucleic acid sequence encoding the N-terminal part of GDE and the nucleic acid sequence encoding the C-terminal part of GDE are selected from the combinations shown in table 2 below. In a further particular embodiment, the dual AAV vector system is designed as follows:
  a) the first AAV vector comprises a genome comprising, in the 5' to 3' orientation:
    a 5' ITR;
    a promoter optionally preceded by an enhancer;
    optionally, an intron;
    a nucleic acid sequence encoding a N-terminal part of GDE selected in the group consisting of the nucleic acid sequences encoding a N-terminal part of GDE shown in table 2 below; and
    a 3'-ITR; and
  b) the second AAV vector comprises a genome comprising, in the 5' to 3' orientation:
    a 5' ITR;
    a nucleic acid sequence encoding a C-terminal part of GDE selected in the group consisting of the nucleic acid sequences encoding a C-terminal part of GDE shown in table 2;
    a polyadenylation signal; and
    a 3'-ITR.

More particularly, the nucleic acid sequence encoding the N-terminal part of GDE may be the nucleotide sequence comprised between nucleotides 1 and 2688 of SEQ ID NO:13 (shown in SEQ ID NO:25) or a corresponding optimized sequence such as SEQ ID NO:27 or SEQ ID NO:28; and the nucleic acid sequence encoding the C-terminal part of GDE may be the nucleotide sequence comprised between nucleotides 1693 and 4599 of SEQ ID NO:13 (shown in SEQ ID NO:26) or a corresponding optimized sequence such as SEQ ID NO:29 or SEQ ID NO:30. In yet another particular embodiment, the nucleic acid sequence encoding the N-terminal part of GDE may be the nucleotide sequence comprised between nucleotides 1 and 1809 of SEQ ID NO:13, or a corresponding optimized sequence such as nucleotides 1-1809 of SEQ ID NO:25, 27 or 28; and the nucleic acid sequence encoding the C-terminal part of GDE may be the nucleotide sequence comprised between nucleotides 2641 and 4599 of SEQ ID NO:13, or a corresponding optimized sequence such as nucleotides 949-2907 of SEQ ID NO:26, 29 or 30.

In another particular embodiment, said first nucleic acid sequence comprises a sequence encoding said N-terminal part of said GDE followed by a splice donor site; and said second nucleic acid sequence comprises a splice acceptor site followed by a sequence encoding said C-terminal part of said GDE. Optionally, the splice donor site in said first nucleic acid sequence may be followed by a recombinogenic sequence; and the splice acceptor site in said second nucleic acid sequence may be preceded by said recombinogenic sequence. Illustrative recombinogenic sequences include an alkaline phosphatase (AP1) fragment, in particular an AP1 fragment selected from the sequences shown in SEQ ID NO:1 to 7, in particular the sequence shown in SEQ ID NO:7; and a AK, F1 phage recombinogenic sequence, such as the sequence shown in SEQ ID NO:8 (WO2014170480 and Trapani et al., 2014, Embo Mol Med, 6(2), 194-211).

In a particular embodiment, said first and second nucleic acid sequences are optimized sequences.

In a further particular embodiment, said first nucleic acid sequence may be preceded by a promoter optionally followed by an intron, and said second nucleic acid sequence may be followed by a polyadenylation signal. Illustrative promoters include, without limitation, ubiquitous, artificial (such as those disclosed in WO2014064277 and WO2015110449) or tissue-specific promoters such as muscle-specific promoters and liver-specific promoters. Muscle-specific promoters include, among others, the SPc5-12, desmin, and MCK promoters. In a further particular embodiment, the muscle-specific promoter is a hybrid muscle-specific promoter such as the E-Syn promoter. The CMV promoter is an illustrative ubiquitous promoter useful in the practice of the present invention. Illustrative introns include, without limitation, introns selected in the group consisting of a human beta globin b2 (or HBB2) intron, a FIX intron and a chicken beta-globin intron, wherein said intron may optionally be a modified intron such as a modified HBB2 intron of SEQ ID NO:9, a modified FIX intron of SEQ ID NO:10, or a modified chicken beta-globin intron of SEQ ID NO:11. Illustrative polyadenylation signals include, without limitation, the human beta globin polyadenylation signal, the bovine growth hormone polyadenylation signal, the SV40 polyadenylation signal, or another naturally occurring or artificial polyadenylation signal.

According to another particular embodiment, each of said first and second AAV vectors may be, independently, a single-stranded or double-stranded self-complementary AAV vector, preferably an AAV vector with an AAV-derived capsid, such as an AAV1, AAV2, variant AAV2, AAV3, variant AAV3, AAV3B, variant AAV3B, AAV4, AAV5, AAV6, variant AAV6, AAV7, AAV8, AAV9, AAV2G9, AAV10 such as AAVcy10 and AAVrh10, AAVrh74, AAVdj, AAV-Anc80, AAV-LK03, AAV2i8, and porcine AAV, such as AAVpo4 and AAVpo6 capsid or with a chimeric capsid, in particular an AAV vector having an AAV8, AAV9, AAVrh74 or AAV2i8 capsid, in particular an AAV9, AAV8 or AAVrh74 capsid, more particularly an AAV8 capsid.

In a second aspect, the invention relates to a cell transduced with the dual recombinant AAV system as described herein, wherein the cell is in particular a liver, muscle, cardiac or CNS cell (such as a neuron, glial cell or an oligodendrocyte).

In a third aspect, the invention relates to a composition, comprising, in a pharmaceutically acceptable carrier, the dual recombinant AAV system or the cell as described herein.

In a fourth aspect, the invention relates to the dual recombinant AAV system, the cell or the composition as described herein, for use as a medicament.

In a fifth embodiment, the invention relates to the dual recombinant AAV system, the cell or the composition as described herein, for use in a method for treating glycogen storage disease III.

In a sixth embodiment, the invention relates to an AAV vector corresponding to the first AAV vector of the dual AAV vector system described herein.

In a seventh embodiment, the invention relates to an AAV vector corresponding to the second AAV vector of the dual AAV vector system described herein.

LEGENDS TO THE FIGURES

FIG. 1. Schematic representation of the GDE expression vectors. Panel A. Following the overlapping strategy, the cDNA of GDE (in light gray) is divided in two portions. The 5' portion of GDE cDNA (GDE-HEAD) was fused with a promoter and an intron. The 3' portion of GDE cDNA (GDE-TAIL) was fused with a polyadenylation signal (polyA). The two GDE cDNA portions shared a homologous sequence which allows, after cell infection, for the reconstitution of full size GDE cDNA (recombination region, RR). Panel B. Dual-hybrid strategy. The GDE-HEAD sequence is fused at the 5' with a promoter and an intron and at the 3' with a splicing donor (SD) and a highly recombinogenic sequence derived from alkaline phosphatase (AP1). The GDE-TAIL sequence is fused at the 3' with the same AP1 sequence and a splicing acceptor (SA), at the 5' a poly-adenylation site has been inserted (polyA). All the transgene expression cassettes are flanked by inverted terminal repeats derived from AAV2 (ITR) for packaging into AAV vectors.

Figure 2:
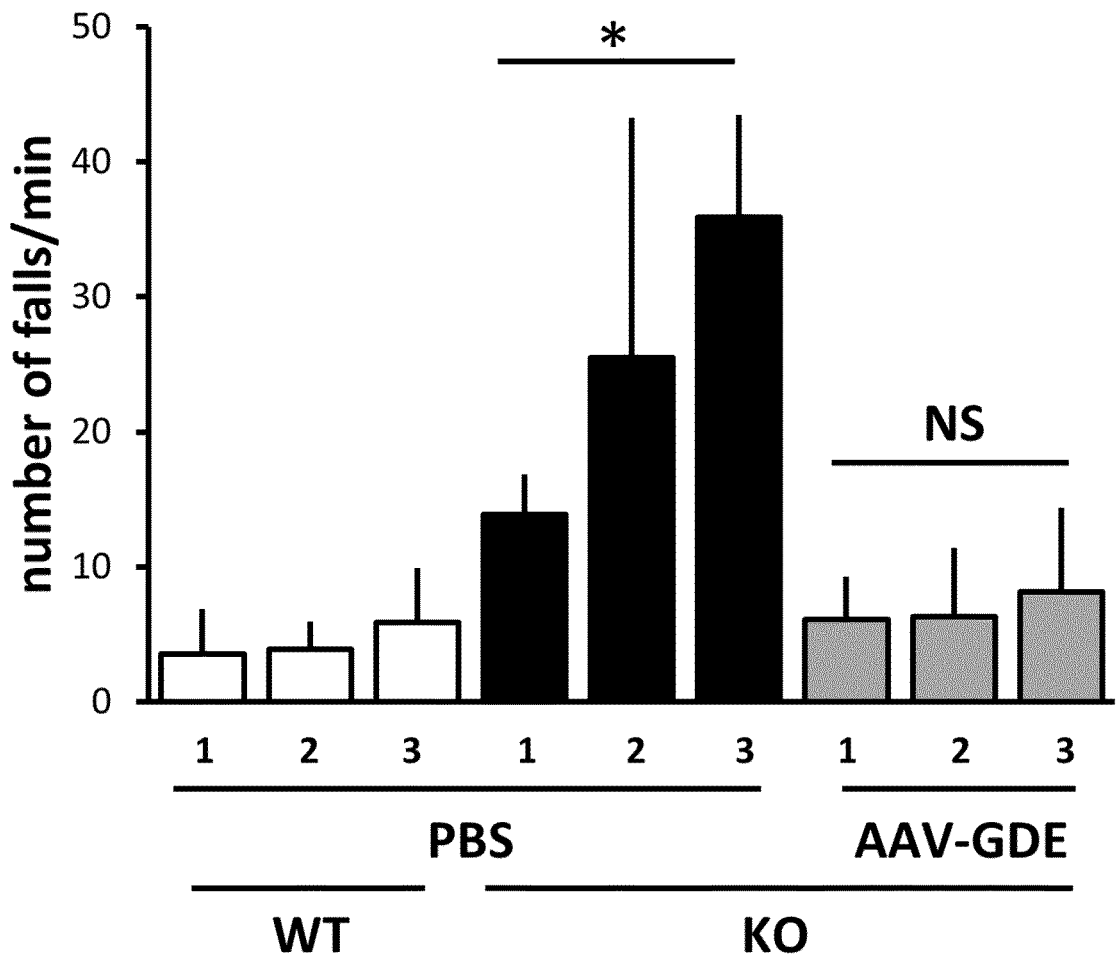

FIG. 2. AAV mediated gene transfer rescues muscle impairment in GDE-KO mice. 3 months-old GDE-KO (n=5 per group) mice were intravenously injected with PBS (KO PBS) or with the two AAV9 vectors expressing the GDE transgene described in FIG. 1A (AAV-GDE). A group of wild-type animals injected with PBS was used as control (WT PBS). In the histograms are shown the results of the wire-hang functional test performed one, two or three months after the injection by measuring the number of falls per minute over a three minutes interval. Statistical analysis has been performed by two way ANOVA time x group with Tukey post-hoc test for group comparison (*=p<0.05 vs WT, NS =not significant).

Figure 3:
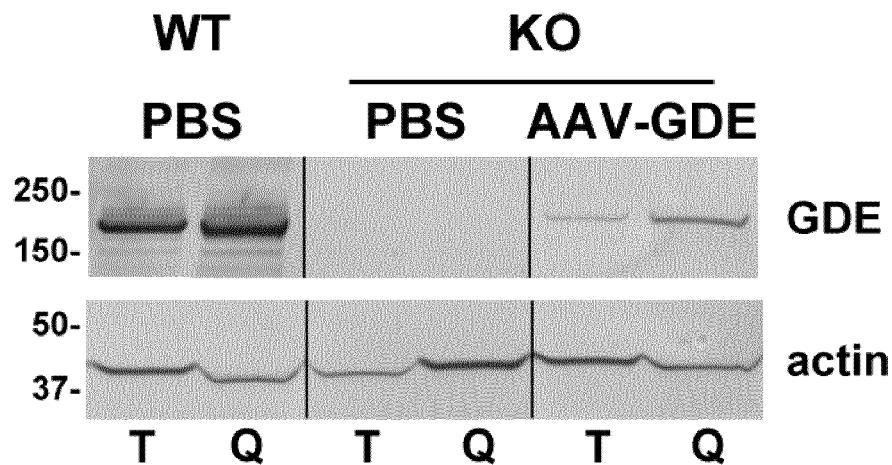

FIG. 3. AAV-mediated GDE expression in skeletal muscles. Wild-type (WT) and GDE knock-out mice (KO) were injected as described in FIG. 2. Mice were sacrificed three months after vectors injection. Triceps (T) and quadriceps (Q) were mechanically homogenized and analyzed by western blot using an antibody specific for GDE. Western-blot with anti-actin antibody has been used as loading control. The positions of a molecular weight marker running in parallel with samples are indicated on the left.

Figure 4:
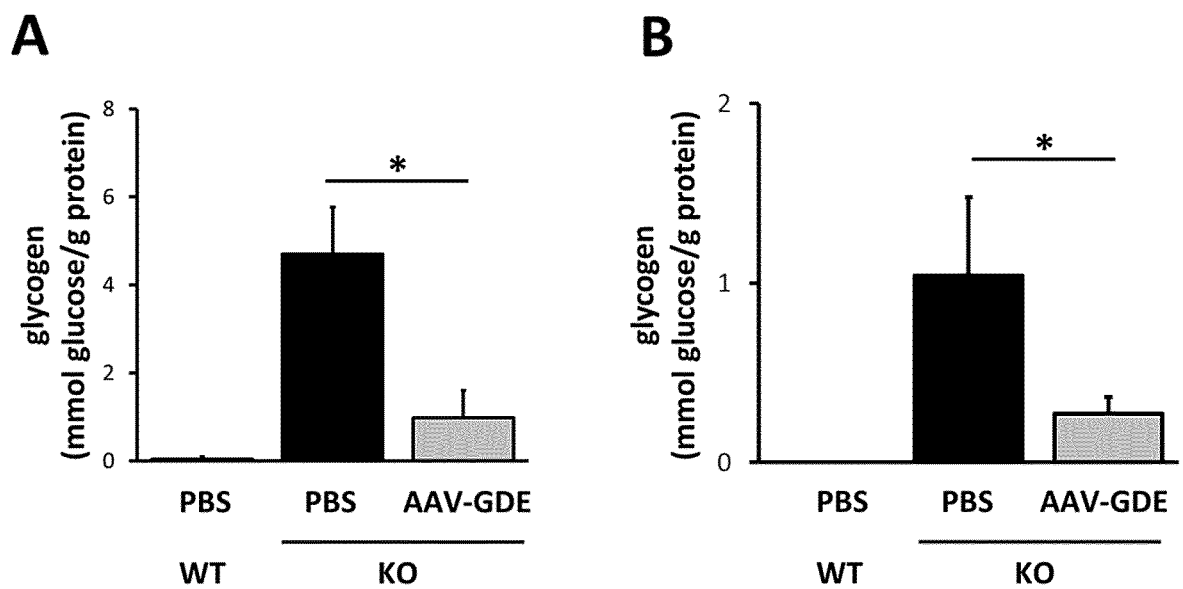

FIG. 4. AAV-mediated gene transfer decreases muscle glycogen accumulation in GDE-KO mice. Mice injected as described in FIG. 2 were sacrificed three months after vectors injection. Quadriceps (Panel A) or hearts (Panel B) were mechanically homogenized and glycogen content has been measured and expressed as the quantity of glucose released after enzymatic digestion of the samples. Statistical analysis has been performed by ANOVA (*=p<0.05 vs KO-PBS).

Figure 5:
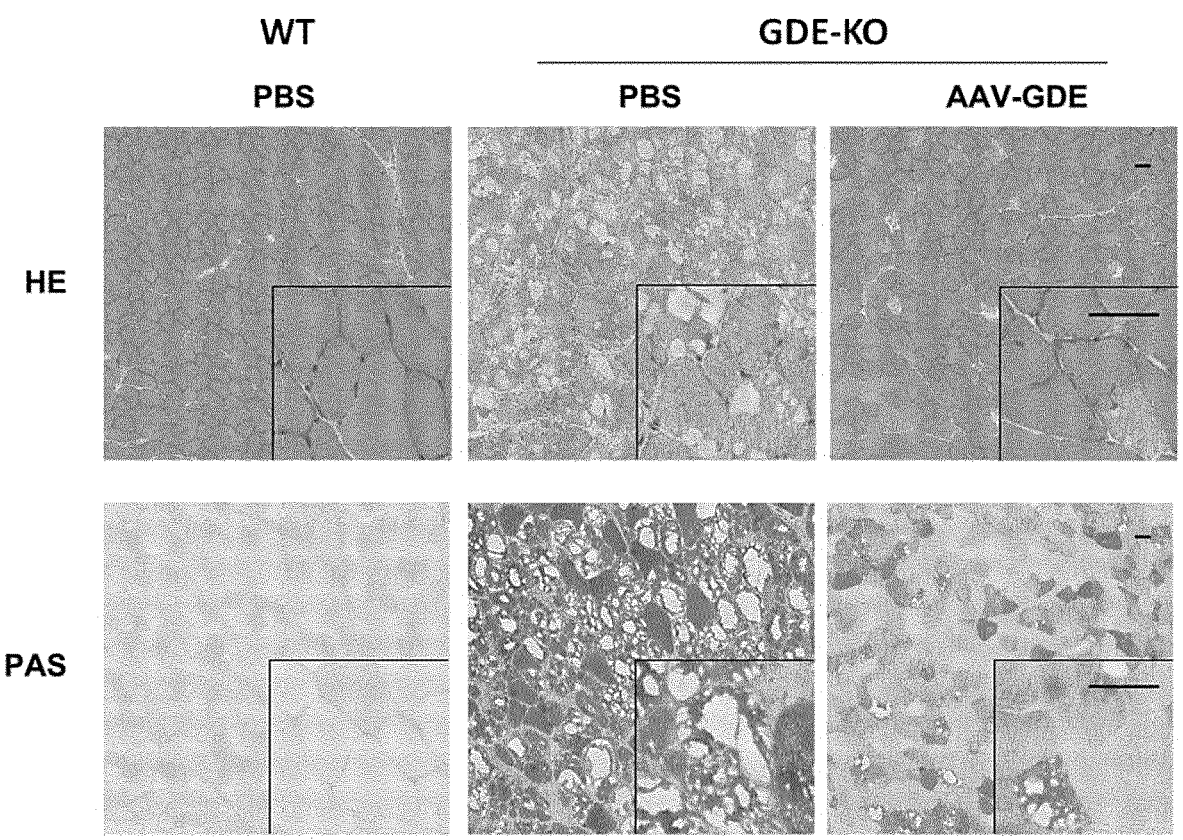

FIG. 5. AAV-mediated gene transfer rescues muscle structure and glycogen accumulation in GDE-KO mice. Mice injected as described in FIG. 2 were sacrificed three months after vectors injection. Hematoxylin eosin (HE, upper panel) and periodic acid-Schiff staining (PAS lower panel) were performed on slices of quadriceps. Scale bar=50 µm are indicated on the right. Inset magnification 4X.

Figure 6:
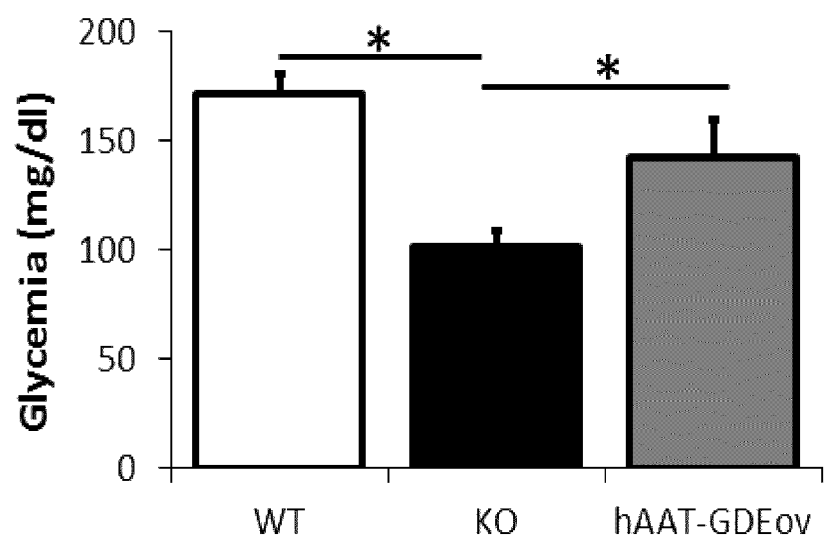

FIG. 6. Dual AAV vector expressing GDE rescues hypoglycemia in GSDIII mice. 3 months old GDE-KO mice were intravenously injected with PBS or with 2E12 vg/mouse of the combination of AAV8-GDE-HEAD and AAV8-GDE-TAIL in a 1:1 ratio (hAAT-GDEov). In parallel wild-type littermates (WT) were intravenously injected with PBS. One month after the injection mice were bled. In the histogram is shown the glycemia measured 1 month post-injection. Statistical analysis was performed by ANOVA (*=p<0.05 as indicated, n=5 mice/group).

Figure 7:
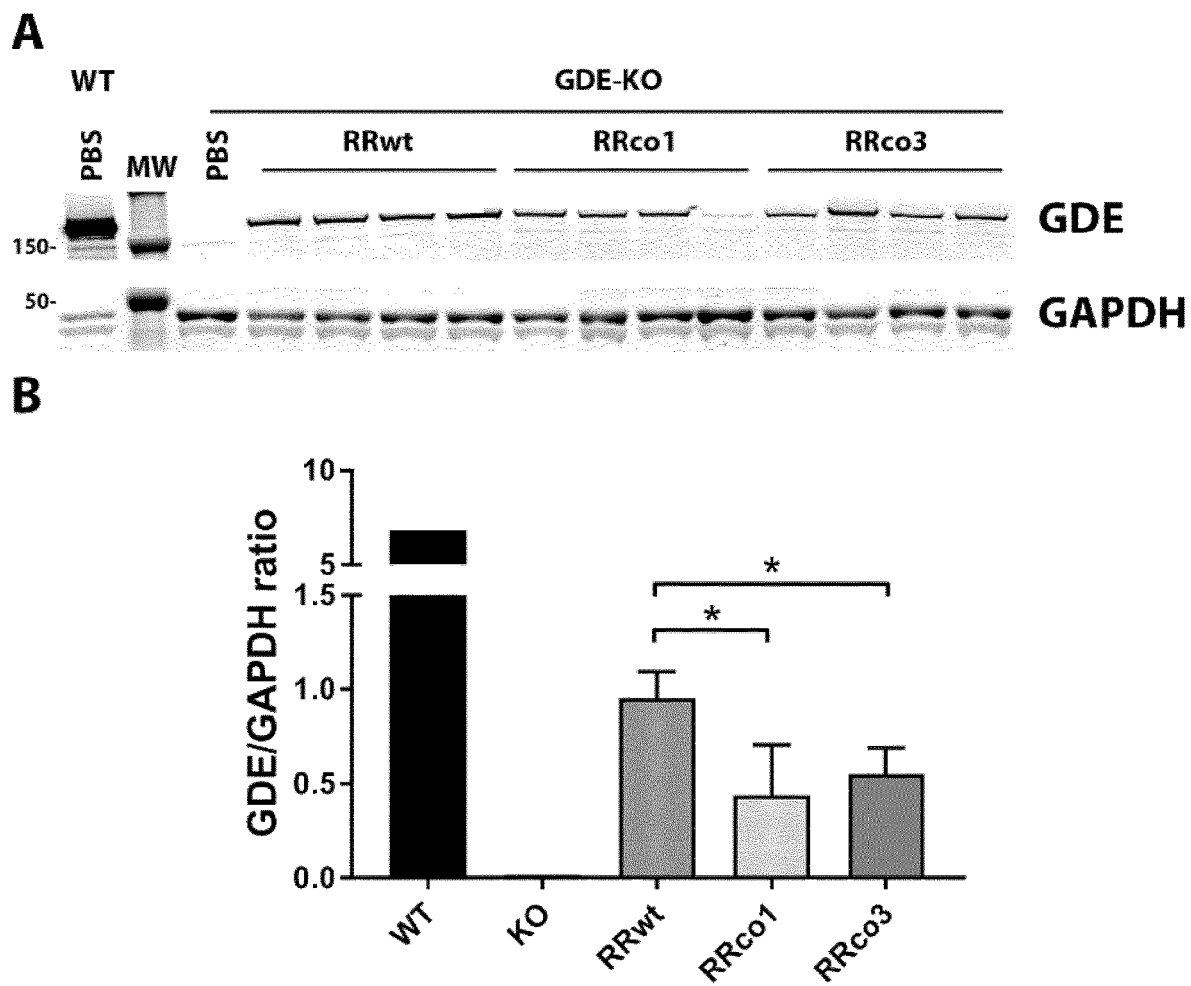

FIG. 7. Recombination region (RR) sequence influences the recombination efficacy of dual overlapping AAV vectors. (A) GDE western-blot performed on the hearts of 3 month-old GDE-KO mice injected with 2E12 vg/mouse of dual AAV vectors bearing the wild-type RR (RRwt) or two different codon optimized versions of the RR (RRco1, RRco3). Anti-GAPDH western-blot was used as loading control. (B) Quantification of the western blot in panel A. Histogram shows the GDE/GAPDH ratio. Statistical analyses to identify significant differences between the three vectors bearing the three RR were performed by ANOVA (* p<0.05, n=4). MW: molecular weight marker.

DETAILED DESCRIPTION OF THE INVENTION

As used herein with respect to any disclosed values or ranges, the term "about" indicates that the stated numerical value allows for slight imprecision, e.g., reasonably close to the value or nearly, such as plus or minus 10% of the stated values or ranges.

An aspect of the invention relates to a dual AAV vector system comprising two AAV vectors, wherein
  a first AAV vector comprises, between 5' and 3' AAV ITRs, a first nucleic acid sequence that encodes a N-terminal part of a glycogen debranching enzyme (GDE), and
  a second AAV vector comprises, between 5' and 3' AAV ITRs, a second nucleic acid sequence that encodes a C-terminal part of said GDE, and
  wherein the first and second nucleic acid sequences encoding said GDE comprise a polynucleotide region that permits the production of a full-length GDE protein, in particular polynucleotide region that permits the production of a full-length nucleic acid sequence that encodes full-length GDE.

Glycogen debranching enzyme, or "GDE", or "amylo-alpha-1,6-glucosidase, 4-alpha-glucanotransferase", encoded by the AGL gene (NCBI gene ID: 178), is an enzyme involved in glycogen degradation. This enzyme has two independent catalytic activities which occur at different sites on the protein: a 4-alpha-glucotransferase activity and an amylo-1,6-glucosidase activity. Mutations in this gene are associated with glycogen storage disease. The AGL gene, located on chromosome 1, is 85 kb in size with 34 exons (NM_000642.2). Bao and colleagues (Genomics, 1997, 38, 155-165) recognized the presence of six different isoforms that differ in the 5' end by using several cryptic splice sites upstream of the translation initiation site. This allows the inclusion or removal of exons. Isoform 1 is the generalized form present in liver, muscle, kidney, and lymphoblastoid cells. Isoforms 2, 3, and 4 are present in the muscle and heart. These isoforms are formed as a result of either alternative splicing or a difference in transcription start points. Isoform 1 contains exons 1 and 3; isoforms 2, 3, and 4 start with exon 2. Isoforms 1 through 4 all contain exon 3 which includes the normal initiation codon for protein translation. Exons 4-35 are present in all isoforms in humans (Bao et al., Genomics, 1997, 38, 155-165; Bao et al 1997, 197, 389-398). The glycogen binding site is encoded by exons 31 and 32 and the active site is encoded by exons 6, 13, 14, and 15 (Elpeleg, 1999, J Pediatr Endocrinol Metab, 12, 363-379).

The term "GDE" or "GDE polypeptide", as used herein, encompasses all natural isoforms of GDE, in particular the precursor form, as well as modified or mutated by insertion(s), deletion (s) and/or substitution(s) GDE proteins or fragments thereof that are functional derivatives of GDE, i.e. that retain biological function of GDE (i.e., have at least one biological activity of the native GDE protein, e. g., can hydrolyze glycogen, as defined above). Any GDE coding sequence known in the art may be used, for example, see SEQ ID NO:12; GenBank Accession number NM_000642.2. In a particular embodiment, the GDE coding sequence is that shown in SEQ ID NO:13, corresponding to SEQ ID NO:12 wherein some restriction sites were removed.

The full-length coding sequence of the GDE polypeptide can be derived from any source, including avian and mammalian species. The term "avian" as used herein includes, but is not limited to, chickens, ducks, geese, quail, turkeys and pheasants. The term "mammal" as used herein includes, but is not limited to, humans, simians and other non-human primates, bovines, ovines, caprines, equines, felines, canines, lagomorphs, etc. In embodiments of the invention, the nucleic acids of the invention encode a human, mouse or quail, in particular a human, GDE polypeptide.

The nucleic acid molecule encoding the GDE polypeptide preferably has at least 50 percent, more preferably at least 60 percent, and even more preferably at least 70 percent identity, such as at least 75, 80, 85, 90 or at least 95 percent identity to the nucleotide sequence of SEQ ID NO:12 or 13. In another particular embodiment, the nucleic acid molecule of the invention has at least 95 percent identity, for example at least 98, 99 or 100 percent identity to the nucleotide sequence of SEQ ID NO:12 or 13.

The term "identical" and declinations thereof refers to the sequence identity between two nucleic acid molecules. When a position in both of the two compared sequences is occupied by the same base e.g., if a position in each of two DNA molecules is occupied by adenine, then the molecules are identical at that position. The percent of identity between two sequences is a function of the number of matching positions shared by the two sequences divided by the number of positions compared×100. For example, if 6 of 10 of the positions in two sequences are matched then the two sequences are 60% identical. Generally, a comparison is made when two sequences are aligned to give maximum identity. Various bioinformatics tools known to the one skilled in the art might be used to align nucleic acid sequences such as BLAST or FASTA.

Furthermore, the nucleic acid molecules of the invention encode a functional GDE protein, i.e. it encodes for a GDE protein that, when expressed, has the functionality of wild-type GDE protein. As defined above, the functionality of wild-type GDE is a 4-alpha-glucotransferase activity and an amylo-1,6-glucosidase activity, involved in glycogen degradation. The functional full-length GDE protein encoded by the reconstituted full-length nucleic acid may have an activity of at least 50%, 60%, 70%, 80%, 90%, 95%, 99% in relation to one, preferably both, functions, or at least 100% as compared to the wild-type GDE protein encoded by the nucleic acid sequence of SEQ ID NO:12 or 13. The activity of the GDE protein encoded by the nucleic acid of the invention may even be of more than 100%, such as of more than 110%, 120%, 130%, 140%, or even more than 150% of the activity of the wild-type GDE protein encoded by the nucleic acid sequence of SEQ ID NO:12 or 13.

A skilled person is readily able to determine whether a nucleic acid expresses a functional GDE protein. Suitable methods would be apparent to those skilled in the art. For example, one suitable in vitro method involves inserting the nucleic acid encoding full-length GDE into a vector, such as a plasmid or viral vector, transfecting or transducing host cells, such as 293T or HeLa cells, or other cells such as Huh7, with the vector, and assaying for GDE activity. Suitable methods are described in more details in the experimental part below. These methods include testing the activity of GDE by determining GDE expression in tissues of a GDE KO animal, such as by western-blot, by following the glucose produced from glycogen phosphorylase-digested glycogen, by evaluating muscle strength of treated GDE-KO animals by wire-hang after administration of the vectors, such as after one, two or three months after administration, or by evaluating the rescue of glycogen accumulation in muscle and/or cardiac tissue.

The sequences in the vectors of the dual AAV vector system of the invention may be optimized, either for optimizing the expression of the GDE polypeptide in vivo or for optimizing the production of full-length GDE, in particular for optimizing recombination when the production of the full-length GDE nucleic acid sequences relies on a recombination event. In particular, the following sequences may be optimized:

the nucleic acid encoding the full-length GDE;
the nucleic acid encoding split-intein, when implemented;
the first nucleic acid sequence encoding the N-terminal part of a GDE;
the second nucleic acid sequence encoding the C-terminal part of a GDE;
the overlapping region of GDE; and/or
the recombinogenic region.

In a particular embodiment, the full-length sequence of GDE is optimized for improving GDE production by the target or host cell. In a further particular embodiment, when recombination is relied on for permitting the production of a full-length GDE-encoding nucleic acid, the region of recombination (for example a GDE polynucleotide sequence that overlaps between the first and second nucleic acid sequences, or a recombinogenic sequence such as an AP1-derived sequence or an AK, F1 recombinogenic sequence) is optimized for improving the recombination between the first and the second nucleic acids. In a particular embodiment, both the full-length sequence of GDE and the region of recombination are optimized. In another embodiment, none of the full-length sequence of GDE and the region of recombination is optimized In yet another embodiment, the full-length sequence of GDE is not optimized, and the region of recombination is optimized. In a further embodiment, the full-length sequence of GDE is optimized, and the region of recombination is not optimized. Sequence optimization may include a number of changes in a nucleic acid sequence, including codon optimization, increase of GC content, decrease of the number of CpG islands, decrease of the number of alternative open reading frames (ARFs) and/or decrease of the number of splice donor and splice acceptor sites. Because of the degeneracy of the genetic code, different nucleic acid molecules may encode the same protein. It is also well known that the genetic codes of different organisms are often biased towards using one of the several codons that encode the same amino acid over the others. Through codon optimization, changes are introduced in a nucleotide sequence that take advantage of the codon bias existing in a given cellular context so that the resulting codon optimized nucleotide sequence is more likely to be expressed in such given cellular context at a relatively high level compared to the non-codon optimised sequence. In a preferred embodiment of the invention, such sequence optimized nucleotide sequence encoding a functional GDE is codon-optimized to improve its expression in human cells compared to non-codon optimized nucleotide sequences coding for the same GDE protein, for example by taking advantage of the human specific codon usage bias.

In a particular embodiment, the optimized GDE coding sequence is codon optimized, and/or has an increased GC content and/or has a decreased number of alternative open reading frames, and/or has a decreased number of splice donor and/or splice acceptor sites, as compared to nucleotides 1-4599 of the wild-type hGDE coding sequence of SEQ ID NO:12 or 13. For example, sequence optimization may result in an at least 2, 3, 4, 5, 10, 11, 12, 13, 14, 15, 16 or 17%, or more (such as up to 26%), increase of GC content in the GDE coding sequence as compared to the sequence of the wild-type GDE sequence. Alternatively, sequence optimization may result in about 2, 3, 4, 5, 6, 7, 8, 9, 10, 11, 12, 13, 14, 15, 16, 17, 18, 19, 20, 21, 22, 23, 24, 25 or 26% increase of GC content in the GDE coding sequence as compared to the sequence of the wild-type GDE sequence. As used herein, a "x % increase of GC content" in an optimized sequence compared to a wild-type reference sequence means that the final GC content of said optimized sequence is the sum of x and of the GC content of the wild type reference sequence. For example, 7% GC increase in a GDE optimized coding sequence compared to a wild-type GDE coding sequence comprising 40% of GC results in an optimized GDE coding sequence having a 47% GC content. In a particular embodiment, sequence optimization results in about 9% increase of GC content in the GDE coding sequence as compared to the sequence of the wild-type GDE sequence. In a particular embodiment, sequence optimization results in about 17% increase of GC content in the GDE coding sequence as compared to the sequence of the wild-type GDE sequence. In a particular embodiment, the nucleic acid sequence encoding a functional full-length GDE polypeptide is "substantially identical", that is, about 70% identical, more preferably about 75% identical, even more preferably about 90% identical, even more preferably about 95% identical, even more preferably about 97%, 98% or even 99% identical to nucleotides 1-4599 of the sequence shown in SEQ ID NO: 14 or 15. Optimization features of two GDE optimized sequences are provided in table 1.

TABLE 1

Comparative analysis of the codon optimized sequences. Sequence analysis has been performed on the wild-type GDE sequence (wt) and on two codon optimized sequences (co1 and co2).

| GDE sequence | % vs wt | % v col | SD (score > 0.8)[a] | SA (score > 0.8)[a] | GC content (%)[b] | CAI[b] | CpG islands[c] |
|---|---|---|---|---|---|---|---|
| wt | | | | | | | |
| (SEQ ID NO: 13) | — | — | 4 | 2 | 40.20 | 0.69 | 0 |
| co1 | | | | | | | |
| (SEQ ID NO: 14) | 75.7 | — | 0 | 1 | 49.67 | 0.72 | 0 |
| co2 | | | | | | | |
| (SEQ ID NO: 15) | 75.0 | 77.3 | 2 | 3 | 57.15 | 0.94 | 11 |

[a]Splicing donor (SD) and splicing acceptor (SA) were predicted using an online tool (http://www.fruitfly.org/seq_tools/splice.html) with a minimum score of 0.8.
[b]GC content and codon adaptation index (CAI) were calculated using the online molecular biology tool (www.genescript.com).
[c]CpG islands smaller than 100 bp and with a GC content threshold of 60% were predicted with the online tool MethPrimerDB (www.urogene.org).

As mentioned above, in addition to the GC content and/or number of ARFs, sequence optimization may also comprise a decrease in the number of CpG islands in the sequence and/or a decrease in the number of splice donor and acceptor sites. Of course, as is well known to those skilled in the art, sequence optimization is a balance between all these parameters, meaning that a sequence may be considered optimized if at least one of the above parameters is improved while one or more of the other parameters is not, as long as the optimized sequence leads to an improvement of the transgene, such as an improved expression and/or a decreased immune response to the transgene in vivo.

In addition, the adaptiveness of a nucleotide sequence encoding a functional GDE to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al, Gene. 1997, 199:293-301; zur Megede et al, Journal of Virology, 2000, 74: 2628-2635). Preferably, a nucleic acid molecule encoding a GDE has a CAI of at least 0.65 (in particular 0.69), 0.7, 0.8, 0.90, 0.92 or 0.94.

In one embodiment, the nucleic acid molecule encoding full-length GDE encodes a protein having between 0 and 50, between 0 and 30, between 0 and 20, between 0 and 15, between 0 and 10, or between 0 and 5 amino acid changes to the protein encoded by the nucleotide sequence of SEQ ID NO:12 or 13. Furthermore, the GDE protein encoded by the full-length nucleic acid may be a variant of GDE known in the art wherein the full-length nucleic acid molecule encodes a protein having between 0 and 50, between 0 and 30, between 0 and 20, between 0 and 15, between 0 and 10, or between 0 and 5 amino acid changes to the GDE protein known in the art.

The GDE transgene is a large transgene that cannot fit the size limit of the cargo of an AAV vector, which is typically of about 5 kb. In addition, GDE is a cytosolic protein that cannot be taken-up by cells in absence of sequences promoting endocytosis and endosomal escape. Therefore, there is an urgent need for efficient means for introducing genetic material into target cells of interest for the expression of functional GDE. Yet, among the means available for large transgene expression into a cell, the use of dual AAV vectors was not straightforward to those skilled in the art. Indeed, to date dual vector technology have been used for expressing structural proteins such as mini- or micro-dystrophins (EP2125006) and dysferlin (Pryadkina et al., 2015, Mol Ther—Methods & Clinical Development, 2, 15009) in the muscle. The present inventors have unexpectedly shown that full-length GDE reconstitution is achievable using a dual AAV vector system of the invention. Therefore, the present invention implements cellular large gene reconstitution by providing to a target cell the large GDE coding sequence split into two different AAV vectors which are designed i) to encode complementary parts of GDE and ii) to contain a polynucleotide region able to promote reconstitution of a long nucleic acid encoding a full-length GDE or to promote reconstitution of a full-length GDE protein from two split-GDE polypeptides. The inventors have also shown for the first time that the dual AAV vector technology may be used for expressing large proteins in the liver, which was never reported before.

By "dual AAV system", it is meant a vector system composed of two AAV vectors, in which system each vector carries a part of a GDE gene to be delivered to a cell and the entire gene is reconstituted by interaction between the first and the second nucleic acid sequences into the cell. Alternatively, the GDE protein is reconstituted by implementation of protein trans-splicing by adding appropriate split-intein coding sequences to each of part of the GDE gene introduced in each AAV vector. In a particular embodiment, the nucleic acid sequences encoding a part of the GDE introduced in each AAV vector have a length of less than 4,6 kb. In another embodiment, the nucleic acid sequences encoding a part of the GDE introduced in each AAV vector have a length of less than 4.5 kb, in particular of less than 4 kb, such as less than 3.5 kb, or less than 3 Kb.

This system implements a polynucleotide region on each of the nucleic acid sequence present in the AAV vectors that permits either the production of a full-length nucleic acid sequence that encodes full-length GDE or the reconstitution of the protein from two split-GDE polypeptides implementing protein trans-splicing using a split-intein (as described in particular in Li et al., 2008, Human Gene Therapy, 19: 958-964). The polynucleotide regions may be selected depending on the mechanism used to promote full-length GDE reconstitution. In particular, the dual vector system of the invention may implement trans-splicing vectors or vectors comprising sequences allowing (homologous) recombination such as overlapping vectors or hybrid transplicing vectors. Alternatively, the polynucleotides are split-intein coding sequences as described in Li et al. (cited above).

Accordingly, in one embodiment, the two vectors of the dual AAV system of the present invention are overlapping vectors. In another embodiment, the two vectors of the dual AAV system are trans-splicing AAV vectors. In still another embodiment, the two vectors of the dual AAV system of the present invention are hybrid trans-splicing AAV vectors.

In the overlapping vector system, the first and second vectors display a region of sequence homology to promote intermolecular homologous recombination, thus generating the large GDE transgene by recombining the two vectors of the dual AAV system (FIG. 1A). In a particular embodiment implementing this overlapping system, the length of the region of sequence homology may vary to a large extent as long as the size of the resulting genome (including the 5'- and 3'-ITR sequences, and any expression control sequence) is compatible with the size limit for encapsidation within an AAV vector. One skilled in the art is well aware of this size limit and is able to adapt the size of both the first and second nucleic acid sequences, and therefore of the region of sequence of homology, according to this knowledge. Therefore, in a particular embodiment, the region of sequence of homology is a polynucleotide sequence of the GDE gene having a length of less than 4599 nucleotides, for example of less than 4500, 4400, 4300, 4200, 4100, 4000, 3500, 3000, 2500, 2000, 1500 or 1000 nucleotides. In another particular embodiment, the region of sequence of homology is a polynucleotide sequence of the GDE gene having a length of at least 100 nucleotides, such as of at least 100, 200, 300, 400, 500, 600, 700 or 800 nucleotides. In a particular embodiment, the maximum region of overlap is from nucleotide 1 to nucleotide 4005 of the GDE nucleotide sequence. In this embodiment, the first AAV vector comprises, between 5' and 3' ITRs, a promoter operably linked to a first nucleic acid sequence that encodes a N-terminal part of GDE, wherein said first nucleic acid sequence consists of nucleotides 1 to nucleotides 4005 of GDE (SEQ ID NO:36); and the second AAV vector comprises, between 5' and 3' ITRs, a second nucleic acid sequence that consists of the full length GDE coding sequence and a polyadenylation signal. Thanks to this embodiment, each first and second nucleotide sequence may be included into an AAV genome whose size is compatible with inclusion into an AAV particle. Indeed, should the full length of GDE be introduced between 5' and 3' AAV ITRs in addition to a promoter and a polyadenylation signal, the resulting sequence would have a size exceeding the size limit of the cargo of an AAV vector. In particular embodiments of the invention, the region of recombination may be any sequence corresponding to a fragment of SEQ ID NO:36. In a further particular embodiment, the region of sequence of homology is a polynucleotide sequence of the GDE gene having a length comprised between 100 and 4599 nucleotides, in particular between 100 and 4500, in particular between 250 and 2500 nucleotides, in particular between 500 and 2000 nucleotides, in particular between 700 and 1500 nucleotides, such as between 750 and 1200 nucleotides, such as between 800 and 1000 nucleotides. For example, In a further particular embodiment, the first nucleic acid sequence comprises a 5' region of SEQ ID NO:12 or 13 comprised between nucleotides 1 and 4599, such as between nucleotides 1 and 2800, for example between nucleotides 1 and 2700, such as nucleotides 1-2640 or 1-2688 of SEQ ID NO:12 or 13 (or of a variant thereof encoding the same GDE polypeptide as SEQ ID NO:12 or 13, or encoding a functional variant thereof) and the second nucleic acid sequence comprises a 3' region of SEQ ID NO:12 or 13 comprised between nucleotides 1 and 4599, such as between nucleotides 100 and 4599, such as between nucleotides 1500 and 4599, for example between nucleotides 1600 and 4599, in particular between nucleotides 1693-4599 or 1810-4599 of SEQ ID NO:12 or 13 (or of a variant thereof encoding the same GDE polypeptide as SEQ ID NO:12 or 13, or encoding a functional variant thereof). In a particular embodiment, the resulting region of sequence homology is comprised between nucleotides 1693 and 2688 or 1810 and 2640 of SEQ ID NO:12 or 13 (or of a variant thereof encoding the same GDE polypeptide as SEQ ID NO:12 or 13, or encoding a functional variant thereof). As mentioned above, the region of sequence homology may be a sequence optimized for recombination. Such sequences include those shown in SEQ ID NO: 16, 17 and 18, optimized from the corresponding wild-type sequence of SEQ ID NO:19 that corresponds to nucleotides 1810-2640 of SEQ ID NO:13. In a particular embodiment, the region of sequence homology is not an optimized sequence, i.e. it corresponds to the wild type sequence. In a particular embodiment, the non-optimized region of homology has a sequence that corresponds to nucleotides 1693 to 2688 or 1810-4599 of SEQ ID NO: 12 or SEQ ID NO:13 (or of a variant thereof encoding the same GDE polypeptide as SEQ ID NO:12 or 13, or encoding a functional variant thereof). In a particular embodiment, the non-optimized region of homology has the sequence shown in SEQ ID NO:19.

In a particular embodiment, in case an overlapping strategy is used, the dual AAV system may comprise a combination of a nucleic acid encoding the N-terminal part of GDE and of a nucleic acid encoding the C-terminal part of GDE selected from the combinations shown in table 2:

TABLE 2 particular combinations of nucleic acid sequence encoding N-terminal and C-terminal parts of GDE, useful in the practice of the invention.

| Nucleic acid encoding the N-terminal part of GDE | Nucleic acid encoding the C-terminal part of GDE | | |
|---|---|---|---|
| 1-1692 of SEQ ID NO: 12 | 1693-2688 of SEQ ID NO: 12 | 1693-2688 of SEQ ID NO: 12 | 2689-4599 of SEQ ID NO: 12 |
| 1-1692 of SEQ ID NO: 12 | 1693-2688 of SEQ ID NO: 13 | 1693-2688 of SEQ ID NO: 13 | 2689-4599 of SEQ ID NO: 12 |
| 1-1692 of SEQ ID NO: 12 | 1693-2688 of SEQ ID NO: 14 | 1693-2688 of SEQ ID NO: 14 | 2689-4599 of SEQ ID NO: 12 |
| 1-1692 of SEQ ID NO: 12 | 1693-2688 of SEQ ID NO: 15 | 1693-2688 of SEQ ID NO: 15 | 2689-4599 of SEQ ID NO: 12 |
| 1-1692 of SEQ ID NO: 13 | 1693-2688 of SEQ ID NO: 12 | 1693-2688 of SEQ ID NO: 12 | 2689-4599 of SEQ ID NO: 13 |
| 1-1692 of SEQ ID NO: 13 | 1693-2688 of SEQ ID NO: 13 | 1693-2688 of SEQ ID NO: 13 | 2689-4599 of SEQ ID NO: 13 |
| 1-1692 of SEQ ID NO: 13 | 1693-2688 of SEQ ID NO: 14 | 1693-2688 of SEQ ID NO: 14 | 2689-4599 of SEQ ID NO: 13 |
| 1-1692 of SEQ ID NO: 13 | 1693-2688 of SEQ ID NO: 15 | 1693-2688 of SEQ ID NO: 15 | 2689-4599 of SEQ ID NO: 13 |
| 1-1692 of SEQ ID NO: 14 | 1693-2688 of SEQ ID NO: 12 | 1693-2688 of SEQ ID NO: 12 | 2689-4599 of SEQ ID NO: 14 |
| 1-1692 of SEQ ID NO: 14 | 1693-2688 of SEQ ID NO: 13 | 1693-2688 of SEQ ID NO: 13 | 2689-4599 of SEQ ID NO: 14 |
| 1-1692 of SEQ ID NO: 14 | 1693-2688 of SEQ ID NO: 14 | 1693-2688 of SEQ ID NO: 14 | 2689-4599 of SEQ ID NO: 14 |
| 1-1692 of SEQ ID NO: 14 | 1693-2688 of SEQ ID NO: 15 | 1693-2688 of SEQ ID NO: 15 | 2689-4599 of SEQ ID NO: 14 |
| 1-1692 of SEQ ID NO: 15 | 1693-2688 of SEQ ID NO: 12 | 1693-2688 of SEQ ID NO: 12 | 2689-4599 of SEQ ID NO: 15 |
| 2689-4599 of SEQ ID NO: 15 | 1693-2688 of SEQ ID NO: 13 | 1693-2688 of SEQ ID NO: 13 | 2689-4599 of SEQ ID NO: 15 |
| 2689-4599 of SEQ ID NO: 15 | 1693-2688 of SEQ ID NO: 14 | 1693-2688 of SEQ ID NO: 14 | 2689-4599 of SEQ ID NO: 15 |
| 2689-4599 of SEQ ID NO: 15 | 1693-2688 of SEQ ID NO: 15 | 1693-2688 of SEQ ID NO: 15 | 2689-4599 of SEQ ID NO: 15 |
| 1-1809 of SEQ ID NO: 12 | 1810-2640 of SEQ ID NO: 12 | 1810-2640 of SEQ ID NO: 12 | 2641-4599 of SEQ ID NO: 12 |
| 1-1809 of SEQ ID NO: 12 | 1810-2640 of SEQ ID NO: 13 | 1810-2640 of SEQ ID NO: 13 | 2641-4599 of SEQ ID NO: 12 |

TABLE 2-continued particular combinations of nucleic acid sequence encoding N-terminal and C-terminal parts of GDE, useful in the practice of the invention.

| Nucleic acid encoding the N-terminal part of GDE | | | Nucleic acid encoding the C-terminal part of GDE |
|---|---|---|---|
| 1-1809 of SEQ ID NO: 12 | 1810-2640 of SEQ ID NO: 14 | 1810-2640 of SEQ ID NO: 14 | 2641-4599 of SEQ ID NO: 12 |
| 1-1809 of SEQ ID NO: 12 | 1810-2640 of SEQ ID NO: 15 | 1810-2640 of SEQ ID NO: 15 | 2641-4599 of SEQ ID NO: 12 |
| 1-1809 of SEQ ID NO: 12 | SEQ ID NO: 18 | SEQ ID NO: 18 | 1-1809 of SEQ ID NO: 12 |
| 1-1809 of SEQ ID NO: 13 | 1810-2640 of SEQ ID NO: 12 | 1810-2640 of SEQ ID NO: 12 | 2641-4599 of SEQ ID NO: 13 |
| 1-1809 of SEQ ID NO: 13 | 1810-2640 of SEQ ID NO: 13 | 1810-2640 of SEQ ID NO: 13 | 2641-4599 of SEQ ID NO: 13 |
| 1-1809 of SEQ ID NO: 13 | 1810-2640 of SEQ ID NO: 14 | 1810-2640 of SEQ ID NO: 14 | 2641-4599 of SEQ ID NO: 13 |
| 1-1809 of SEQ ID NO: 13 | 1810-2640 of SEQ ID NO: 15 | 1810-2640 of SEQ ID NO: 15 | 2641-4599 of SEQ ID NO: 13 |
| 1-1809 of SEQ ID NO: 13 | SEQ ID NO: 18 | SEQ ID NO: 18 | 1-1809 of SEQ ID NO: 13 |
| 1-1809 of SEQ ID NO: 14 | 1810-2640 of SEQ ID NO: 12 | 1810-2640 of SEQ ID NO: 12 | 2641-4599 of SEQ ID NO: 14 |
| 2641-4599 of SEQ ID NO: 14 | 1810-2640 of SEQ ID NO: 13 | 1810-2640 of SEQ ID NO: 13 | 2641-4599 of SEQ ID NO: 14 |
| 1-1809 of SEQ ID NO: 14 | 1810-2640 of SEQ ID NO: 14 | 1810-2640 of SEQ ID NO: 14 | 2641-4599 of SEQ ID NO: 14 |
| 1-1809 of SEQ ID NO: 14 | 1810-2640 of SEQ ID NO: 15 | 1810-2640 of SEQ ID NO: 15 | 2641-4599 of SEQ ID NO: 14 |
| 1-1809 of SEQ ID NO: 14 | SEQ ID NO: 18 | SEQ ID NO: 18 | 2641-4599 of SEQ ID NO: 14 |
| 1-1809 of SEQ ID NO: 15 | 1810-2640 of SEQ ID NO: 12 | 1810-2640 of SEQ ID NO: 12 | 2641-4599 of SEQ ID NO: 15 |
| 2641-4599 of SEQ ID NO: 15 | 1810-2640 of SEQ ID NO: 13 | 1810-2640 of SEQ ID NO: 13 | 2641-4599 of SEQ ID NO: 15 |
| 2641-4599 of SEQ ID NO: 15 | 1810-2640 of SEQ ID NO: 14 | 1810-2640 of SEQ ID NO: 14 | 2641-4599 of SEQ ID NO: 15 |
| 2641-4599 of SEQ ID NO: 15 | 1810-2640 of SEQ ID NO: 15 | 1810-2640 of SEQ ID NO: 15 | 2641-4599 of SEQ ID NO: 15 |
| 1-1809 of SEQ ID NO: 15 | SEQ ID NO: 18 | SEQ ID NO: 18 | 2641-4599 of SEQ ID NO: 15 |

For the sake of clarity, the table should be understood as follows. Taking as an example the first combination appearing in the table:

the nucleic acid sequence encoding the N-terminal part of GDE consists of nucleotides 1-1692 of SEQ ID NO:12 fused to nucleotides 1693-2688 of SEQ ID NO:12; and the nucleic acid sequence encoding the C-terminal part of GDE consists of nucleotides 1693-2688 of SEQ ID NO:12 fused to nucleotides 2689-4599 of SEQ ID NO:12.

In this combination, the region of recombination corresponds to nucleotides 1693-2688 of SEQ ID NO:12. Taking as an example the second combination appearing in the table:

the nucleic acid sequence encoding the N-terminal part of GDE consists of nucleotides 1-1692 of SEQ ID NO:12 fused to nucleotides 1693-2688 of SEQ ID NO:13; and the nucleic acid sequence encoding the C-terminal part of GDE consists of nucleotides 1693-2688 of SEQ ID NO:13 fused to nucleotides 2689-4599 of SEQ ID NO:12.

In this combination, the region of recombination corresponds to nucleotides 1693-2688 of SEQ ID NO:13. Etc.

Trans-splicing AAV vectors typically carry a splicing donor signal and a splicing acceptor signal. More specifically, the trans-splicing approach also relies on a co-transduction approach in which the transgene is split such that one vector may contain a promoter, a 5' portion of the GDE gene (encoding a N-terminal part of a GDE polypeptide, followed by a splice donor sequence. The downstream vector contains a splice acceptor sequence, the remaining 3' portion of the GDE gene (encoding a C-terminal part of a GDE polypeptide), and a polyadenylation signal. A concatamerization event in the correct orientation generates a single DNA molecule containing the intended large transgene expression cassette. The splicing signals may be any set of splicing donor and its corresponding acceptor, such as the splicing signals from the dystrophin gene, the splicing signals from adenovirus, or any synthetic splicing signals. In a particular embodiment, the splice donor and acceptor sites are SV40 splice donor and acceptor sites. As mentioned above, one skilled in the art is well aware of the size limit for encapsidation into an AAV vector and is able to adapt the length of both the first and second nucleic acid sequences to this size limit. In a particular embodiment implementing the trans-splicing system, the first nucleic acid sequence comprises a 5' region of SEQ ID NO:12 or 13 comprised between nucleotides 1 and 4599, such as between nucleotides 1 and 4000, 1-3500, 1-3000, 1-2500, or 1-2000, for example between nucleotides 1 and 1900, such as nucleotides 1-1898 of SEQ ID NO:12 or 13 (or of a variant thereof encoding the same GDE polypeptide as SEQ ID NO:12 or 13, or encoding a functional variant thereof) and the second nucleic acid sequence comprises a 3' region of SEQ ID NO:12 or 13 comprised between nucleotides 100 and 4599, for example between nucleotides 500-4599, 1000-4599, 1500-4599, 1600 and 4599, in particular nucleotides 1899-4599 of SEQ ID NO:12 or 13 (or of a variant thereof encoding the same GDE polypeptide as SEQ ID NO:12 or 13, or encoding a functional variant thereof).

Hybrid trans-splicing technique is a combination of the overlapping and trans-splicing techniques. AAV vectors will typically carry a homologous recombinogenic overlapping sequence, such as sequences from the human alkaline phosphatase (AP1) gene or from the AK, F1 phage recombinogenic region. In a particular embodiment, the recombinogenic overlapping sequence is an AP1 fragment, such as a fragment selected in the group consisting of SEQ ID NO:1 to 7, in particular SEQ ID NO:7. In another particular embodiment, the recombinogenic overlapping sequence is an AK, F1 recombinogenic sequence, such as the sequence shown in SEQ ID NO:8. Again, as mentioned above, one skilled in the art is well aware of the size limit for encapsidation into an AAV vector and is able to adapt the length of both the first and second nucleic acid sequences to this size limit. In a particular embodiment implementing the hybrid trans-splicing system, the first nucleic acid sequence comprises a 5' region of SEQ ID NO:12 or 13 comprised between nucleotides 1 and 4599, such as between nucleotides 1 and 4000, 1-3500, 1-3000, 1-2500, or 1-2000, for example between nucleotides 1 and 1900, such as nucleotides 1-1898 of SEQ ID NO:12 or 13 (or of a variant thereof encoding the same GDE polypeptide as SEQ ID NO:12 or 13, or encoding a functional variant thereof) and the second nucleic acid sequence comprises a 3' region of SEQ ID NO:12 or 13 comprised between nucleotides 100 and 4599, for example between nucleotides 500-4599, 1000-4599, 1500-4599, 1600 and 4599, in particular nucleotides 1899-

4599 of SEQ ID NO:12 or 13 (or of a variant thereof encoding the same GDE polypeptide as SEQ ID NO:12 or 13, or encoding a functional variant thereof).

In a particular embodiment implementing the trans-splicing technique or hybrid trans-splicing technique, oligo-assisted intramolecular genome recombination (as described in Hirsch et al. 2009, PLoS One, 4(11): e7705) may be additionally used to optimize trans-splicing events.

The inventors have found that the above described dual AAV system surprisingly restores GDE expression in skeletal muscles of treated mice three months after their injection, that glycogen accumulation is decreased, and that muscle strength is restored. They have further shown that the above described dual AAV system is able to rescue the hypoglycemic phenotype of GSDIII mice. This means that the present strategy is efficient in treating diseases involving GDE lack of function, in particular GSD III.

In the AAV vectors of the present invention, the first and second nucleic acid may be operably linked to one or more expression control sequences and/or other sequences improving the expression of a transgene. As used herein, the term "operably linked" refers to a linkage of polynucleotide elements in a functional relationship. A nucleic acid is "operably linked" when it is placed into a functional relationship with another nucleic acid sequence. For instance, a promoter, or another transcription regulatory sequence, is operably linked to a coding sequence if it affects the transcription of the coding sequence. Such expression control sequences are known in the art, such as promoters, enhancers (such as cis-regulatory modules (CRM)), introns, polyadenylation signals, etc.

In particular, the first AAV vector, comprising a nucleic acid sequence encoding a N-terminal part of a GDE, may include a promoter. The promoter may be an ubiquitous, artificial (such as those disclosed in WO2014064277 and WO2015110449) or tissue-specific promoter (such as muscle-specific promoters and liver-specific promoters, or combination of such promoters with enhancer sequences such as CRMs (in particular muscle-specific or liver-specific CRMs as described below), in particular a promoter able to promote expression in cells or tissues in which expression of GDE is desirable such as in cells or tissues in which GDE expression is desirable in GDE-deficient patients.

In a particular embodiment, the promoter is a muscle-specific promoter. Non-limiting examples of muscle-specific promoters include the muscle creatine kinase (MCK) promoter. Non-limiting examples of suitable muscle creatine kinase promoters are human muscle creatine kinase promoters and truncated murine muscle creatine kinase (tMCK) promoters) (Wang B et al, Construction and analysis of compact muscle-specific promoters for AAV vectors. Gene Ther. 2008 November;15(22):1489-99) (representative GenBank Accession No. AF188002). Human muscle creatine kinase has the Gene ID No. 1158 (representative GenBank Accession No. NC_000019.9, accessed on Dec. 26, 2012). Other examples of muscle-specific promoters include myosin light chain (MLC) promoters, for example MLC2 (Gene ID No. 4633; representative GenBank Accession No. NG_007554.1, accessed on Dec. 26, 2012); myosin heavy chain (MHC) promoters, for example alpha-MHC (Gene ID No. 4624; representative GenBank Accession No. NG_023444.1, accessed on Dec. 26, 2012); desmin promoters (Gene ID No. 1674; representative GenBank Accession No. NG_008043.1, accessed on Dec. 26, 2012); cardiac troponin C promoters (Gene ID No. 7134; representative GenBank Accession No. NG_008963.1, accessed on Dec. 26, 2012); troponin I promoters (Gene ID Nos. 7135, 7136, and 7137; representative GenBank Accession Nos. NG_016649.1, NG_011621.1, and NG_007866.2, accessed on Dec. 26, 2012); myoD gene family promoters (Weintraub et al., Science, 251, 761 (1991); Gene ID No. 4654; representative GenBank Accession No. NM_002478, accessed on Dec. 26, 2012); actin alpha promoters (Gene ID Nos. 58, 59, and 70; representative GenBank Accession Nos. NG_006672.1, NG_011541.1, and NG_007553.1, accessed on Dec. 26, 2012); actin beta promoters (Gene ID No. 60; representative GenBank Accession No. NG_007992.1, accessed on Dec. 26, 2012); actin gamma promoters (Gene ID No. 71 and 72; representative GenBank Accession No. NG_011433.1 and NM_001199893, accessed on Dec. 26, 2012); muscle-specific promoters residing within intron 1 of the ocular form of Pitx3 (Gene ID No. 5309) (Coulon et al; the muscle-specific promoter corresponds to residues 11219-11527 of representative GenBank Accession No. NG_008147, accessed on Dec. 26, 2012); and the promoters described in US Patent Publication US 2003/0157064. Other muscle-specific promoters include the SPc5-12, desmin and MCK promoters. In a further particular embodiment, the muscle-specific promoter is a hybrid muscle-specific promoter such as a hybrid promoter combining a modified MCK enhancer to a muscle-specific promoter, such as to the SPc5-12 promoter. In a particular embodiment, the hybrid muscle-specific promoter is the E-Syn promoter described in Wang et al., Gene Therapy volume 15, pages 1489-1499 (2008) (sequence shown in SEQ ID NO:35).

Other tissue-specific or non-tissue-specific promoters may be useful in the practice of the invention. For example, the first AAV vector may include a tissue-specific promoter which is a promoter different from a muscle-specific promoter, such as a liver-specific or neuron-specific promoter.

In a particular embodiment, the promoter is a liver-specific promoter such as the alpha-1 antitrypsin promoter (hAAT) (SEQ ID NO: 20), the transthyretin promoter, the albumin promoter, the thyroxine-binding globulin (TBG) promoter, the LSP promoter (comprising a thyroid hormone-binding globulin promoter sequence, two copies of an alpha1-microglobulin/bikunin enhancer sequence, and a leader sequence-III, C. R., et al. (1997). Optimization of the human factor VIII complementary DNA expression plasmid for gene therapy of hemophilia A. Blood Coag. Fibrinol. 8: S23-S30.), etc. Other useful liver-specific promoters are known in the art, for example those listed in the Liver Specific Gene Promoter Database compiled the Cold Spring Harbor Laboratory (http://rulai.cshl.edu/LSPD/). A preferred liver-specific promoter in the context of the invention is the hAAT promoter. In another embodiment, the promoter is a promoter directing expression in one tissue or cell of interest (in particular in muscle cells), and in liver cells. For example, to some extent, promoters specific of muscle cells such as the desmin, Spc5-12, E-syn and MCK promoters, in particular desmin, Spc5-12, E-syn and MCK promoters, may present some leakage of expression into liver cells, which can be advantageous to induce immune tolerance of the subject to the GDE protein expressed from the nucleic acid of the invention.

Neuron-specific promoters include, but are not limited to the following: synapsin-1 (Syn) promoter, neuron-specific enolase (NSE) promoter (Andersen et al. , Cell. Mol. Neurobiol., 13:503-15 (1993)), neurofilament light-chain gene promoter (Piccioli et al. , Proc. Natl. Acad. Sci. USA, 88:5611-5 (1991)), and the neuron-specific vgf gene promoter (Piccioli et al. , Neuron, 15:373- 84 (1995)), among others which will be apparent to the skilled artisan.

In another embodiment, the promoter is a ubiquitous promoter. Representative ubiquitous promoters include the cytomegalovirus enhancer/chicken beta actin (CAG) promoter, the cytomegalovirus enhancer/promoter (CMV) (optionally with the CMV enhancer) [see, e.g., Boshart et al, Cell, 41:521-530 (1985)], the PGK promoter, the SV40 early promoter, the retroviral Rous sarcoma virus (RSV) LTR promoter (optionally with the RSV enhancer), the dihydrofolate reductase promoter, the β-actin promoter, the phosphoglycerol kinase (PGK) promoter, and the EF1 alpha promoter.

In addition, the promoter may also be an endogenous promoter such as the albumin promoter or the GDE promoter.

In a particular embodiment, the promoter is associated to an enhancer sequence, such as a cis-regulatory module (CRMs) or an artificial enhancer sequence. For example, the promoter may be associated to an enhancer sequence such as the human ApoE control region (or Human apolipoprotein E/C-I gene locus, hepatic control region HCR-1 —Genbank accession No. U32510, shown in SEQ ID NO: 21). In a particular embodiment, an enhancer sequence such as the ApoE sequence is associated to a liver-specific promoter such as those listed above, and in particular such as the hAAT promoter. Other CRMs useful in the practice of the present invention include those described in Rincon et al., Mol Ther. 2015 January; 23(1):43-52, Chuah et al., Mol Ther. 2014 September; 22(9):1605-13 or Nair et al., Blood. 2014 May 15;123(20):3195-9. Other regulatory elements that are, in particular, able to enhance muscle-specific expression of genes, in particular expression in cardiac muscle and/or skeletal muscle, are those disclosed in WO2015110449. Particular examples of nucleic acid regulatory elements that comprise an artificial sequence include the regulatory elements that are obtained by rearranging the transcription factor binding sites (TFBS) that are present in the sequences disclosed in WO2015110449. Said rearrangement may encompass changing the order of the TFBSs and/or changing the position of one or more TFBSs relative to the other TFBSs and/or changing the copy number of one or more of the TFBSs. For example, a nucleic acid regulatory element for enhancing muscle-specific gene expression, in particular cardiac and skeletal muscle-specific gene expression, may comprise binding sites for E2A, HNH 1 , NF1 , C/EBP, LRF, MyoD, and SREBP; or for E2A, NF1 , p53, C/EBP, LRF, and SREBP; or for E2A, HNH 1 , HNF3a, HNF3b, NF1 , C/EBP, LRF, MyoD, and SREBP; or E2A, HNF3a, NF1 , C/EBP, LRF, MyoD, and SREBP; or for E2A, HNF3a, NF1 , CEBP, LRF, MyoD, and SREBP; or for HNF4, NF1 , RSRFC4, C/EBP, LRF, and MyoD, or NF1 , PPAR, p53, C/EBP, LRF, and MyoD. For example, a nucleic acid regulatory element for enhancing muscle-specific gene expression, in particular skeletal muscle-specific gene expression, may also comprise binding sites for E2A, NF1 , SRFC, p53, C/EBP, LRF, and MyoD; or for E2A, NF1 , C/EBP, LRF, MyoD, and SREBP; or for E2A, HNF3a, C/EBP, LRF, MyoD, SEREBP, and Tall_b; or for E2A, SRF, p53, C/EBP, LRF, MyoD, and SREBP; or for HNF4, NF1 , RSRFC4, C/EBP, LRF, and SREBP; or for E2A, HNF3a, HNF3b, NF1 , SRF, C/EBP, LRF, MyoD, and SREBP; or for E2A, CEBP, and MyoD. In further examples, these nucleic acid regulatory elements comprise at least two, such as 2, 3, 4, or more copies of one or more of the TFBSs recited before. Other regulatory elements that are, in particular, able to enhance liver-specific expression of genes, are those disclosed in WO2009130208.

In another particular embodiment, the first nucleic acid sequence is preceded by an intron, in particular an intron placed between the promoter and the sequence coding the N-terminal part of GDE. An intron may be introduced to increase mRNA stability and the production of the protein. In a further embodiment, the intron is a human beta globin b2 (or HBB2) intron, a coagulation factor IX (FIX) intron, a SV40 intron or a chicken beta-globin intron. In another further embodiment, the intron is a modified intron (in particular a modified HBB2 or FIX intron) designed to decrease the number of, or even totally remove, alternative open reading frames (ARFs) found in said intron. Preferably, ARFs are removed whose length spans over 50 bp and have a stop codon in frame with a start codon. ARFs may be removed by modifying the sequence of the intron. For example, modification may be carried out by way of nucleotide substitution, insertion or deletion, preferably by nucleotide substitution. As an illustration, one or more nucleotides, in particular one nucleotide, in an ATG or GTG start codon present in the sequence of the intron of interest may be replaced resulting in a non-start codon. For example, an ATG or a GTG may be replaced by a CTG, which is not a start codon, within the sequence of the intron of interest.

The classical HBB2 intron is shown in SEQ ID NO:22. For example, this HBB2 intron may be modified by eliminating start codons (ATG and GTG codons) within said intron. In a particular embodiment, the modified HBB2 intron has the sequence shown in SEQ ID NO:9. The classical FIX intron is derived from the first intron of human FIX and is shown in SEQ ID NO:23. FIX intron may be modified by eliminating start codons (ATG and GTG codons) within said intron. In a particular embodiment, the modified FIX intron has the sequence shown in SEQ ID NO:10. The classical chicken-beta globin intron used in nucleic acid constructs is shown in SEQ ID NO:24. Chicken-beta globin intron may be modified by eliminating start codons (ATG and GTG codons) within said intron. In a particular embodiment, the modified chicken-beta globin intron has the sequence shown in SEQ ID NO:11.

The inventors have previously shown in WO2015/162302 that such a modified intron, in particular a modified HBB2 or FIX intron, has advantageous properties and can significantly improve the expression of a transgene.

In a particular embodiment, in case an overlapping strategy is used, the dual AAV system may be as follows:

a) the first AAV vector comprises a genome comprising, in the 5' to 3' orientation:
  a 5' ITR,
  a promoter optionally preceded by an enhancer,
  optionally, an intron as defined above,
  a nucleic acid sequence encoding a N-terminal part of GDE selected in the group consisting of the nucleic acid sequences encoding a N-terminal part of GDE shown in table 2; and
  a 3'-ITR; and b) the second AAV vector comprises a genome comprising, in the 5' to 3' orientation:
  a 5' ITR,
  a nucleic acid sequence encoding a C-terminal part of GDE selected in the group consisting of the nucleic acid sequences encoding a C-terminal part of GDE shown in table 2,
  a polyadenylation signal, and
  a 3'-ITR.

In a particular embodiment, in case an overlapping strategy is used, the dual AAV system may be as follows:

a) the first AAV vector comprises a genome comprising, in the 5' to 3' orientation:
- a 5' ITR,
- a promoter optionally preceded by an enhancer,
- optionally, an intron as defined above,
- the nucleic acid sequence encoding the N-terminal part of GDE, such as the nucleotide sequence comprised between nucleotides 1 and 2688 of SEQ ID NO:13 (shown in SEQ ID NO:25) or a corresponding optimized sequence such as SEQ ID NO:27 or SEQ ID NO:28; and
- a 3'-ITR; and b) the second AAV vector comprises a genome comprising, in the 5' to 3' orientation:
- a 5' ITR,
- the nucleic acid sequence encoding the C-terminal part of GDE, such as the nucleotide sequence comprised between nucleotides 1693 and 4599 of SEQ ID NO:13 (shown in SEQ ID NO:26) or a corresponding optimized sequence such as SEQ ID NO:29 or SEQ ID NO:30,
- a polyadenylation signal, and
- a 3'-ITR.

In another embodiment, the first and second nucleic acid sequences comprise an overlapping region which corresponds to nucleotides 1810-2640 of SEQ ID NO:13 (as shown in SEQ ID NO:19), or which corresponds to an optimized version of this sequence, in particular selected in the group consisting of SEQ ID NO:16, 17 and 18. In this embodiment, the sequence encoding the N-terminal part and the C-terminal part of GDE may be either nucleotides 1-1809 and 2641-4599 of SEQ ID NO:13, respectively, or optimized sequences derived therefrom, such as nucleotides 1-1809 of SEQ ID NO:25, 27 or 28, and nucleotides 949-2907 of SEQ ID NO:26, 29 or 30, respectively.

In another particular embodiment, wherein a trans-splicing approach is used, the dual AAV system may be as follows:

a) the first AAV vector comprises a genome comprising, in the 5' to 3' orientation:
- a 5' ITR,
- a promoter optionally preceded by an enhancer,
- optionally, an intron as defined above,
- the nucleic acid sequence encoding the N-terminal part of GDE, such as the nucleotide sequence comprised between nucleotides 1 and 1898 of SEQ ID NO:13 (shown in SEQ ID NO:31) or an optimized sequence thereof such as nucleotides 1-1898 of SEQ ID NO:27 or SEQ ID NO:28),
- a splice donor site, and
- a 3'-ITR; and b) the second AAV vector comprises a genome comprising, in the 5' to 3' orientation:
- a 5' ITR
- a splice acceptor site,
- the nucleic acid sequence encoding the C-terminal part of GDE, such as the nucleotide sequence comprised between nucleotides 1899 and 4599 of SEQ ID NO:13 (shown in SEQ ID NO:32) or an optimized sequence thereof such as nucleotides 207-2907 of SEQ ID NO:29 or SEQ ID NO:30,
- a polyadenylation signal, and
- a 3'-ITR.

In another particular embodiment, wherein a hybrid trans-splicing approach is used, the dual AAV system may be as follows:

a) the first AAV vector comprises a genome comprising, in the 5' to 3' orientation:
- a 5' ITR,
- a promoter optionally preceded by an enhancer,
- optionally, an intron as defined above,
- the nucleic acid sequence encoding the N-terminal part of GDE, such as the nucleotide sequence comprised between nucleotides 1 and 1898 of SEQ ID NO:13 (shown in SEQ ID NO:31) or an optimized sequence thereof such as nucleotides 1-1898 of SEQ ID NO:27 or SEQ ID NO: 28),
- a splice donor site, such as the SV40 splice donor of SEQ ID NO:33,
- a recombinogenic sequence, such as a sequence selected in the group consisting of SEQ ID NO:1 to 8, in particular SEQ ID NO: 7, and
- a 3'-ITR; and b) the second AAV vector comprises a genome comprising, in the 5' to 3' orientation:
- a 5' ITR
- the recombinogenic sequence used in the first AAV vector, in particular SEQ ID NO: 7,
- a splice acceptor site, such as the SV40 splice donor of SEQ ID NO:34,
- the nucleic acid sequence encoding the C-terminal part of GDE, such as the nucleotide sequence comprised between nucleotides 1899 and 4599 of SEQ ID NO:13 (shown in SEQ ID NO:32) or an optimized sequence thereof such as nucleotides 207-2907 of SEQ ID NO:29 or SEQ ID NO:30,
- a polyadenylation signal, and
- a 3'-ITR.

As mentioned above, in designing the AAV vectors of the dual AAV system of the invention, one skilled in the art will take care of respecting the size limit of the vector used for delivering said construct to a cell or organ. In particular, one skilled in the art knows that a major limitation of AAV vector is its cargo capacity which may vary from one AAV serotype to another but is thought to be limited to around the size of parental viral genome. For example, 5 kb is the maximum size usually thought to be packaged into an AAV8 capsid. (Wu Z. et al., Mol Ther., 2010, 18(1): 80-86; Lai Y. et al., Mol Ther., 2010, 18(1): 75-79; Wang Y. et al., Hum Gene Ther Methods, 2012, 23(4): 225-33). Accordingly, those skilled in the art will take care in practicing the present invention to select the components of the nucleic acid construct of the invention so that the resulting nucleic acid sequence, including sequences coding AAV 5'- and 3'-ITRs to preferably not exceed 110% of the cargo capacity of the AAV vector implemented, in particular to preferably not exceed 5.5 kb.

In the present invention, the dual AAV system comprises AAV vectors.

The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter). Therefore, AAV vectors have arisen considerable interest as potential vectors for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV-1, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p.16026), -7, -8, -9, -2G9, -10 such as cy10 and -rh10, -rh74, -dj, Anc80, LK03, AAV2i8, porcine AAV serotypes such as AAVpo4 and AAVpo6, and tyrosine, lysine and serine capsid mutants of the AAV serotypes, etc. In addition, other non-natural engineered variants and chimeric AAV can also be useful.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells. Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. In the context of the present invention, the AAV vector comprises an AAV capsid able to transduce the target cells of interest, in particular hepatocytes, muscle cells, CNS or cardiac cells. According to a particular embodiment, the AAV vector is of the AAV-1, -2, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), --3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p.16026), -7, -8, -9, -2G9, -10 such as -cy10 and -rh10, -rh74, -dj, Anc80, LK03, AAV2i8, AAV-B1, porcine AAV such as AAVpo4 and AAVpo6, and tyrosine, lysine and serine capsid mutants of AAV serotypes. In a particular embodiment, the AAV vector is of the AAV8, AAV9, AAVrh74 or AAV2i8 serotype (i.e. the AAV vector has a capsid of the AAV8, AAV9, AAVrh74 or AAV2i8 serotype). In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype. For example, the genome of the pseudotyped vector may have a capsid derived from the AAV8, AAV9, AAVrh74 or AAV2i8 serotype, and its genome may be derived from and different serotype. In a particular embodiment, the AAV vector has a capsid of the AAV8, AAV9 or AAVrh74 serotype, in particular of the AAV8 or AAV9 serotype, more particularly of the AAV8 serotype. In another particular embodiment, the AAV vector has a capsid of the AAV-B 1 serotype, as disclosed in WO2016054557.

In a specific embodiment, wherein the vector is for use in delivering the transgene to muscle cells, the AAV vector may be selected, among others, in the group consisting of AAV8, AAV9 and AAVrh74. In another specific embodiment, wherein the vector is for use in delivering the transgene to liver cells, the AAV vector may be selected, among others, in the group consisting of AAVS, AAV8, AAV9, AAV-LK03, AAV-Anc80 and AAV3B.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example a chimeric AAV vector can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In addition, capsid variants may include single amino acid changes such as tyrosine mutants (e.g. as described in Zhong et al., 2008)

In addition, the genome of the AAV vector may either be a single stranded or self-complementary double-stranded genome (McCarty et al., Gene Therapy, 2003). Self-complementary double-stranded AAV vectors are generated by deleting the terminal resolution site from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid. As is known in the art, additional suitable sequences may be introduced in the nucleic acid construct of the invention for obtaining a functional viral vector. Suitable sequences include AAV ITRs In a particular embodiment, the first AAV vector comprises a muscle-specific promoter as described above, in particular a muscle-specific promoter that presents some leakage of expression into liver cells.

In another particular embodiment of the invention, the nucleic acid sequence in the first AAV vector comprises a liver-specific promoter as described above, and the AAV vector is capable of transducing liver tissue or cells as described above. The protolerogenic and metabolic properties of the liver are advantageously implemented thanks to this embodiment to develop highly efficient and optimized vectors to express GDE in hepatocytes and to induce immune tolerance to the protein.

The invention also relates to a cell, in particular an isolated cell, for example a liver cell, a cardiac cell, a CNS cell or a muscle cell, that is transduced with the dual AAV system of the invention. The cell of the invention expresses full length GDE. Cells of the invention may be delivered to the subject in need thereof, such as GDE-deficient patient, by any appropriate administration route such as via injection in the liver, in the CNS, in the heart, in the muscle(s) or in the bloodstream of said subject. In a particular embodiment, the invention involves transducing liver or muscle cells, in particular liver or muscle cells of the subject to be treated, and administering said transduced liver and/or muscle cells into which the nucleic acid has been introduced to the subject. In a particular embodiment, the liver cells are liver cells from the patient to be treated, or are liver stem cells that are further transformed, and differentiated in vitro into liver cells, for subsequent administration to the patient. In another embodiment, the cell is a muscle cell from the patient to be treated, or is a muscle stem cell that is further transformed, and optionally differentiated in vitro into muscle cells, for subsequent administration to the patient.

The present invention also relates to a composition comprising the first AAV vector as described above, including any of the specific embodiments disclosed herein.

The present invention also relates to a composition comprising the second AAV vector as described above, including any of the specific embodiments disclosed herein.

The present invention also relates to a dual plasmid system adapted for the production of the first and second AAV vector genomes. Said dual plasmid system comprises:
   a first plasmid comprising, between 5' and 3' AAV ITRs, the first nucleic acid sequence that encodes a N-terminal part of a glycogen debranching enzyme (GDE) as described above according to any specific embodiment disclosed herein, and
   a second plasmid comprising, between 5' and 3' AAV ITRs, a second nucleic acid sequence that encodes a C-terminal part of said GDE as described above according to any specific embodiment disclosed herein, and
   wherein the first and second nucleic acid sequences encoding said GDE comprise a polynucleotide region that permits the production of a full-length GDE protein, in particular a polynucleotide region that permits the production of a full-length nucleic acid sequence that encodes full-length GDE, as described above.

All embodiments and specific features disclosed above for the dual AAV vector system may be introduced into the corresponding dual plasmid system of the invention.

Furthermore, in another aspect, the present invention also relates to a composition comprising the first plasmid as described above, including any of the specific embodiments disclosed herein.

Furthermore, in another aspect, the present invention also relates to a composition comprising the second plasmid as described above, including any of the specific embodiments disclosed herein.

The invention further relates to a method for the production of the first or second AAV vector of the dual AAV system of the invention, comprising introducing the first or second plasmid of the dual plasmid system of the invention into a cell expressing, either stably or transiently, AAV Rep and Cap proteins as is well known in the art.

The present invention also provides compositions comprising one or both AAV vectors of the dual AAV system of the invention, one or both plasmid vectors of the dual plasmid system of the invention, or the cell of the invention. It should be understood that although the invention relates to a dual AAV system, each AAV component of this system may be included in the same composition, or in separate compositions. In the latter case, both compositions will be administered to a subject in need thereof, either simultaneously, separately or sequentially. Such compositions comprise a therapeutically effective amount of the therapeutic (the AAV vector(s) or the cell of the invention), and a pharmaceutically acceptable carrier. The term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid, vector or cell of the invention is formulated in a composition comprising phosphate-buffered saline and supplemented with 0.25% human serum albumin. In another particular embodiment, the nucleic acid, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous or intramuscular administration, preferably intravenous administration, to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

In an embodiment, the AAV vector(s) or the cell of the invention can be delivered in a vesicle, in particular a liposome. In yet another embodiment, the vector(s) or the cell of the invention can be delivered in a controlled release system.

Methods of administration of the AAV vector(s) or of the cell of the invention include but are not limited to intradermal, intramuscular, intraperitoneal, intravenous, subcutaneous, intranasal, epidural, and oral routes. In a particular embodiment, the administration is via the intravenous or intramuscular route. The AAV vector(s) or the cell of the invention, whether vectorized or not, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment, e.g. the liver or the muscle. This may be achieved, for example, by means of an implant, said implant being of a porous, nonporous, or gelatinous material, including membranes, such as sialastic membranes, or fibers.

The amount of the therapeutic of the invention which will be effective in the treatment of GSDIII can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the AAV vectors or the cell of the invention administered to the subject in need thereof will vary based on several factors including, without limitation, the route of administration, the specific disease treated, the subject's age or the level of expression necessary to obtain the therapeutic effect. One skilled in the art can readily determine, based on its knowledge in this field, the dosage range required based on these factors and others. In case of a treatment comprising administering an AAV vector to the subject, typical doses of the vector are of at least $1\times10^8$ vector genomes per kilogram body weight (vg/kg), such as at least $1\times10^9$ vg/kg, at least $1\times10^{10}$ vg/kg, at least $1\times10^{11}$ vg/kg, at least $1\times10^{12}$ vg/kg at least $1\times10^{13}$ vg/kg, at least $1\times10^{14}$ vg/kg or at least $1\times10^{15}$ vg/kg.

The invention also relates to a method for treating GSD III, which comprises a step of delivering a therapeutic effective amount of the dual AAV system, the composition(s) or the cell of the invention to a subject in need thereof.

The invention also relates to a method for treating GSD III, said method inducing no immune response to the transgene (i.e. to the GDE polypeptide encoded by the reconstituted full-length nucleic acid), or inducing a reduced immune response to the transgene, comprising a step of delivering a therapeutic effective amount of the dual AAV system, pharmaceutical composition or cell of the invention to a subject in need thereof The invention also relates to a method for treating GSD III, said method comprising repeated administration of a therapeutic effective amount of the dual AAV system, pharmaceutical composition or cell of the invention to a subject in need thereof In this aspect, the first AAV vector comprises a promoter which is functional in liver cells, thereby allowing immune tolerance to the expressed GDE polypeptide produced therefrom. As well, in this aspect, the pharmaceutical composition used in this aspect comprises a first AAV vector comprising a promoter which is functional in liver cells. In case of delivery of cells, in particular of liver, cardiac, CNS or muscle cells, said cells may be cells previously collected from the subject in need of the treatment and that were engineered by transducing them with the dual AAV system of the invention to thereby make them able to produce the full-length GDE polypeptide. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a dual AAV system of the invention is done using a different AAV serotype for each successive administration, thereby avoiding a reduction of efficacy because of a possible immune response against a previously administered AAV vector. For example, a first administration of an AAV vector comprising an AAV8 capsid may be done, followed by the administration of a vector comprising an AAV9 capsid.

According to the present invention, a treatment may include curative, alleviation or prophylactic effects. Accordingly, therapeutic and prophylactic treatment includes amelioration of the symptoms of GSD III or preventing or otherwise reducing the risk of developing a particular glycogen storage disease. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition. The term "treatment" is used herein to refer to any regimen that can benefit an animal, in particular a mammal, more particularly a human subject.

The invention also relates to an ex vivo gene therapy method for the treatment of GSD III, comprising transducing the dual AAV system into an isolated cell of a patient in need thereof, for example an isolated hematopoietic stem cell, and introducing said cell into said patient in need thereof.

The invention also relates to the dual AAV system, the pharmaceutical composition or the cell of the invention for use as a medicament.

The invention also relates to the dual AAV system, the pharmaceutical composition or the cell of the invention, for use in a method for treating a disease caused by a mutation in the GDE gene, in particular in a method for treating GSDIII (Cori disease).

The invention further relates to the use of the dual AAV system, the pharmaceutical composition or the cell of the invention, in the manufacture of a medicament useful for treating GSD III (Cori disease).

EXAMPLES

The invention is further described in detail by reference to the following experimental examples and the attached figures. These examples are provided for purposes of illustration only, and are not intended to be limiting.

MATERIAL AND METHODS

Glycogen Content

Glycogen content was measured indirectly as the glucose released after total digestion by amyloglucosidase. The glucose released was determined using a glucose assay kit by measuring the absorbance using an EnSpire alpha plate reader at 540 nm.

Western Blot Analysis

Mouse tissues were prepared as previously described (Amalfitano et al PNAS 1999). Briefly, 50-100 mg of tissue were weighed and homogenized in DNAse/RNAse free water, then centrifuged for 20 minutes at 10000×g. The supernatant was used in the following steps. Protein concentration was determined using the BCA Protein Assay. SDS-page electrophoresis was performed in a 4-15% gradient polyacrylamide gel. After transfer the membrane was blocked with Odyssey buffer and incubated with anti-GDE or anti-actin primary antibodies. The membrane was washed and incubated with the appropriate secondary antibody, and visualized by Odyssey imaging system .

Histology

For muscle histology, after euthanasia triceps brachii, quadriceps femoris, diaphragm, and heart were snap-frozen in isopentane previously chilled in liquid nitrogen. Serial 8 µm cross-sections were cut in a Leica CM3050 S cryostat . To minimize sampling error, 3 sections of each specimen were obtained and stained with hematoxylin-eosin (HE) and periodic acid-Schiff (PAS) according to standard procedures.

Wire-Hang

Forelimbs wire-hanging test was performed as already reported (Zhang et al., 2012, Hum Gene Ther, 23(5): 460-472). A 4-mm wire was used to record the number of fall over a period of 3 minutes. The number of falls per minute was reported.

Glycemia

Glycemia was measured in serum by using a glucose assay kit and by measuring resulting absorbance on an EnSpire alpha plate reader at 540 nm.

Illustrative GDE Activity Test

GDE activity is assayed by following the glucose produced from glycogen phosphorylase-digested glycogen. Glycogen phosphorylase-digested glycogen is produced as previously described (Tabata et al, 1992, Eur J Biochem, 206(2), 345-348). Briefly, 1 g of oyster glycogen and 200 U of rabbit muscle glycogen phosphorylase-a are dissolved in 20 ml digestion buffer (0.2 M phosphate, pH 6.8), and are dialyzed against a large volume of digestion buffer at 37° C. overnight. Afterwards glycogen phosphorylase is precipitated by heating at 95° C. for 30 min and removed by centrifugation. Glycogen phosphorylase-digested glycogen is subsequently precipitated by adding 40 ml of ethanol and collected by centrifugation. Glucose production is coupled to NAD+reduction with hexokinase and glucose-6-phosphate dehydrogenase (Kunst et al, 1984, Methods of Enzymatic Analysis $3^{rd}$ edition 6, 163-172), and the resulting absorption change at 340 nm is monitored on an ultraspec 2100 pro spectrophotometer.

RESULTS

In an effort to develop a therapeutic strategy for type III glycogen storage disease (GSDIII) we obtained a knock-out mouse model for the glycogen debranching enzyme (GDE). This model recapitulates the phenotype of the disease observed in GSDIII patients. In particular GDE knock-out mice (GDE-KO), that completely lacks the GDE activity, have an impairment in the muscular strength and accumulate glycogen in different tissues.

Here we tested the efficacy of GDE gene replacement for the functional and biochemical rescue of muscle impairment in GDE knock-out animals. The development of an AAV-based gene therapy for GDE is complicated by the fact that the transgene size is approximately 4.6 Kb, and this, together with promoter, intron, poly-adenylation site and ITRs, exceed the limit size of AAV vectors. We developed a dual vector strategy for the expression of GDE by fusing the 5' portion (HEAD; SEQ ID NO: 25) of the transgene with a cytomegalovirus promoter and a human beta globin (HBB2) intron whereas the 3' portion (TAIL; SEQ ID NO: 26) was fused with HBB2 polyA signal (HBB2 polyA) as indicated in FIG. 1A. The recombination of the two vectors through the homology region occurring after cell infection leads to the reconstitution of the full size cDNA. The HEAD and TAIL expression cassettes were pseudotyped in AAV9 and co-injected in vivo. We intravenously injected GDE-KO mice (n=5 per group) with 2E12 vg/mouse of AAV9-GDE-HEAD and AAV9-GDE-TAIL combined in a 1:1 ratio (AAV-GDE). As controls, we intravenously injected, with PBS, wild-type (WT) and GDE-KO animals (KO). We evaluated the muscle strength by wire-hang one, two and three months post-injection. Two-way ANOVA time x treatment was used to analyze the data obtained. We observed a statistical significant time dependent increase in the number of fall per minute (p=0.009). Treatment comparison revealed a striking increase ($p<1\times10^{-8}$) in the number of falls per minute in KO animals as compared to WT (FIG. 2). Surprisingly, AAV treatment completely rescues the muscular strength reducing the number of falls per minute to levels undistinguishable to those observed in WT animals (p=0.648). Three months after vector injection mice were sacrificed and muscles analyzed to verify at the biochemical level the correction of the phenotype. We first measured by western-blot with an anti-GDE specific antibody, the GDE protein expression level in triceps and quadriceps (FIG. 3). As expected a clear band with a size compatible to that of GDE was detected in both triceps and quadriceps of WT animals and totally absent in KO mice thus demonstrating the specificity of our assay. Interestingly, we observed a GDE band in the triceps and quadriceps of KO mice injected with the combination of GDE HEAD and TAIL AAV9 vectors. This indicates that the recombination of the two vectors occurred in the muscles thus leading to a substantial expression of the GDE enzyme. We then verified if the expression of the GDE protein was able to rescue the glycogen accumulation observed in KO mice. Quadriceps and heart tissues were homogenized and tested for glycogen content. In WT animals, glycogen accumulation in muscles is almost absent. Conversely when we analyzed KO muscles we observed a significant increase in glycogen accumulation in both quadriceps and heart ($p<1\times10^{-3}$). Surprisingly, when we treated mice with the combination of AAV9 HEAD and TAIL, we measured glycogen levels that were significantly reduced compared to the KO animals ($p<0.01$) (FIG. 4). Consistently, hematoxylin eosin (HE) and periodic acid Schiff (PAS) staining, confirmed biochemical data (FIG. 5). In particular, quadriceps of GDE-KO mice showed an extensive vacuolization, visualized by HE staining, together with a massive glycogen accumulation as displayed in the PAS staining. Three months after the treatment of GDE-KO mice with the combination of AAV9-GDE-HEAD and AAV9-GDE-TAIL vectors, a complete rescue of muscles architecture and glycogen accumulation was observed. Of note HE and PAS staining performed in the quadriceps of GDE-KO animals treated with the two vectors were comparable to similar staining performed in WT animals.

We then developed a dual overlapping AAV vector expressing GDE under the transcriptional control of a potent, liver-specific human alpha1-antitrypsin promoter (hAAT). We intravenously injected GDE-KO mice (n=5 per group) with 2E12 vg/mouse of AAV8-hAAT-GDE-HEAD and AAV8-GDE-TAIL combined in a 1:1 ratio (hAAT-GDEov). As controls, we intravenously injected, with PBS, wild-type (WT) and GDE-KO animals (KO). As expected, one month after the injection KO animals showed reduced glycemia ($p=0.0001$). Surprisingly the administration of the liver-specific dual vector significantly increased glycemia ($p=0.009$) to levels comparable to those measured in WT animals ($p=0.060$), demonstrating for the first time that the dual AAV vector technology may be used for expressing large proteins in the liver.

Taken together these data indicate that the systemic administration of the dual vectors expressing GDE leads to the expression of a functional GDE protein in the muscle, to the complete clearance of glycogen accumulation in muscle and to the rescue of the hypoglycemic phenotype in GSDIII mice. The biochemical rescue observed in the muscle is accompanied by a functional rescue of mice strength, thus indicating the overlapping strategy as a viable strategy for the rescue of GSDIII in vivo.

To evaluate if the nucleotide composition of the recombination region (RR) affects the recombination efficacy of the dual overlapping vectors we modified the sequence of the RR by different codon optimization algorithms that resulted in the progressive increase of the GC content (Table 3). In particular, RRwt was the wild-type 1810-2640 recombination region (GC content 39.55%), RRco1 was a codon optimized version of the same region with a GC content of 46.88% and RRco3 was a co version of the same region containing 65.90% of GC. Regions 1-1809 and 2641-4599 in each of the vector correspond to the wild-type GDE coding sequence. 2E12 vg/mouse of the dual AAV vectors bearing the described recombination regions were produced and injected in three month-old GDE-KO animals. Three months after injection animals were sacrificed. GDE levels of expression were analyzed by western blot in the heart of animals injected with the three vectors (FIG. 7A). The quantification of the GDE bands indicates a significant increased GDE expression in animals injected with the dual AAV vector containing the RRwt (FIG. 7B). These data indicate that the composition of the recombination region affects the recombination efficacy of the two vectors.

TABLE 3

Comparative analysis of the optimized recombination sequences. Sequence analysis has been performed on the wild-type GDE sequence (RRwt) and on the two codon optimized (RRco1, and RRco3) recombination regions.

| RR sequence | % vs wt | % v co1 | % v co2 | SD (score > 0.8)[a] | SA (score > 0.8)[a] | GC content (%)[b] | CAI[b] | CpG islands[c] |
|---|---|---|---|---|---|---|---|---|
| RRwt |
| (SEQ ID NO: 19) | — | — | — | 0 | 0 | 39.55 | 0.70 | 0 |
| RRco1 |
| (SEQ ID NO: 16) | 74.6 | — | — | 5 | 1 | 46.88 | 0.69 | 0 |
| RRco3 |
| (SEQ ID NO: 18) | 69.8 | 74.9 | 89.9 | 2 | 0 | 65.90 | 1.00 | 2 |

[a]Splicing donor (SD) and splicing acceptor (SA) were predicted using an online tool (www.fruitfly.org) with a minimum score of 0.8.
[b]GC content and codon adaptation index (CAI) were calculated using the online molecular biology tool (www.genescript.com).
[c]CpG islands smaller than 100 bp and with a GC content threshold of 60% were predicted with the online tool MethPrimerDB (www.urogene.org).

The invention claimed is:

1. A dual AAV vector system comprising two AAV vectors, wherein:
   a first AAV vector comprises, between 5' and 3' AAV ITRs, a first nucleic acid sequence that encodes a N-terminal part of a glycogen debranching enzyme (GDE), and
   a second AAV vector comprises, between 5' and 3' AAV ITRs, a second nucleic acid sequence that encodes a C-terminal part of said GDE, and
   wherein the first and second nucleic acid sequences encoding said GDE comprise a polynucleotide region that permits the production of a full-length GDE protein.

2. The dual AAV vector system according to claim 1, wherein said polynucleotide region is a GDE polynucleotide sequence that overlaps between said first and second nucleic acid sequences.

3. The dual AAV vector system according to claim 2, wherein said polynucleotide sequence that overlaps between said first and second nucleic acid sequences is between about 100 and about 4500 nucleotides.

4. The dual AAV vector system according to claim 1, wherein:
   said first nucleic acid sequence comprises a sequence encoding said N-terminal part of said GDE followed by a splice donor site; and
   said second nucleic acid sequence comprises a splice acceptor site followed by a sequence encoding said C-terminal part of said GDE.

5. The dual AAV vector system according to claim 4, wherein:
   the splice donor site in said first nucleic acid sequence is followed by a recombinogenic sequence and the splice acceptor site in said second nucleic acid sequence is preceded by said recombinogenic sequence.

6. The dual AAV vector system according to claim 5, wherein said recombinogenic sequence is:
   an alkaline phosphatase (AP1) fragment; or
   an AK, F1 phage recombinogenic sequence.

7. The dual AAV vector system according to claim 5, wherein said recombinogenic sequence is:
   an alkaline phosphatase (AP1) fragment, wherein said AP1 fragment is selected from the sequences shown in SEQ ID NO:1 to 7; or
   an AK, F1 phage recombinogenic sequence as shown in SEQ ID NO:8.

8. The dual AAV vector system according to claim 5, wherein said recombinogenic sequence is:
   an alkaline phosphatase (AP1) fragment, wherein said AP1 fragment is as shown in SEQ ID NO:7; or
   an AK, F1 phage recombinogenic sequence as shown in SEQ ID NO:8.

9. The dual AAV vector system according to claim 1, wherein said first and second nucleic acid sequences are optimized sequences.

10. The dual AAV vector system according to claim 1, wherein said first nucleic acid sequence is preceded by a promoter optionally followed by an intron, and said second nucleic acid sequence is followed by a polyadenylation signal.

11. The dual AAV vector system according to claim 1, wherein the polynucleotide region is a GDE polynucleotide sequence that overlaps between said first and second nucleic acid sequences, and wherein the nucleic acid sequence encoding the N-terminal part of GDE and the nucleic acid sequence encoding the C-terminal part of GDE are selected from the combinations shown in the following table:

| Nucleic acid encoding the N-terminal part of GDE | | Nucleic acid encoding the C-terminal part of GDE | |
| --- | --- | --- | --- |
| 1-1692 of SEQ ID NO:12 | 1693-2688 of SEQ ID NO: 12 | 1693-2688 of SEQ ID NO: 12 | 2689-4599 of SEQ ID NO:12 |
| 1-1692 of SEQ ID NO:12 | 1693-2688 of SEQ ID NO: 13 | 1693-2688 of SEQ ID NO: 13 | 2689-4599 of SEQ ID NO:12 |
| 1-1692 of SEQ ID NO: 12 | 1693-2688 of SEQ ID NO: 14 | 1693-2688 of SEQ ID NO: 14 | 2689-4599 of SEQ ID NO:12 |
| 1-1692 of SEQ ID NO:12 | 1693-2688 of SEQ ID NO: 15 | 1693-2688 of SEQ ID NO: 15 | 2689-4599 of SEQ ID NO:12 |
| 1-1692 of SEQ ID NO:13 | 1693-2688 of SEQ ID NO: 12 | 1693-2688 of SEQ ID NO: 12 | 2689-4599 of SEQ ID NO: 13 |
| 1-1692 of SEQ ID NO:13 | 1693-2688 of SEQ ID NO: 13 | 1693-2688 of SEQ ID NO: 13 | 2689-4599 of SEQ ID NO: 13 |
| 1-1692 of SEQ ID NO:13 | 1693-2688 of SEQ ID NO: 14 | 1693-2688 of SEQ ID NO: 14 | 2689-4599 of SEQ ID NO: 13 |
| 1-1692 of SEQ ID NO: 13 | 1693-2688 of SEQ ID NO: 15 | 1693-2688 of SEQ ID NO: 15 | 2689-4599 of SEQ ID NO: 13 |
| 1-1692 of SEQ ID NO:14 | 1693-2688 of SEQ ID NO: 12 | 1693-2688 of SEQ ID NO: 12 | 2689-4599 of SEQ ID NO: 14 |
| 1-1692 of SEQ ID NO:14 | 1693-2688 of SEQ ID NO: 13 | 1693-2688 of SEQ ID NO: 13 | 2689-4599 of SEQ ID NO: 14 |
| 1-1692 of SEQ ID NO:14 | 1693-2688 of SEQ ID NO: 14 | 1693-2688 of SEQ ID NO: 14 | 2689-4599 of SEQ ID NO: 14 |
| 1-1692 of SEQ ID NO:14 | 1693-2688 of SEQ ID NO: 15 | 1693-2688 of SEQ ID NO: 15 | 2689-4599 of SEQ ID NO: 14 |
| 1-1692 of SEQ ID NO: 15 | 1693-2688 of SEQ ID NO: 12 | 1693-2688 of SEQ ID NO: 12 | 2689-4599 of SEQ ID NO:15 |
| 2689-4599 of SEQ ID NO:15 | 1693-2688 of SEQ ID NO: 13 | 1693-2688 of SEQ ID NO: 13 | 2689-4599 of SEQ ID NO:15 |
| 2689-4599 of SEQ ID NO:15 | 1693-2688 of SEQ ID NO: 14 | 1693-2688 of SEQ ID NO: 14 | 2689-4599 of SEQ ID NO:15 |
| 2689-4599 of SEQ ID NO:15 | 1693-2688 of SEQ ID NO: 15 | 1693-2688 of SEQ ID NO: 15 | 2689-4599 of SEQ ID NO:15 |
| 1-1809 of SEQ ID NO:12 | 1810-2640 of SEQ ID NO: 12 | 1810-2640 of SEQ ID NO: 12 | 2641-4599 of SEQ ID NO:12 |
| 1-1809 of SEQ ID NO:12 | 1810-2640 of SEQ ID NO: 13 | 1810-2640 of SEQ ID NO: 13 | 2641-4599 of SEQ ID NO:12 |
| 1-1809 of SEQ ID NO:12 | 1810-2640 of SEQ ID NO: 14 | 1810-2640 of SEQ ID NO: 14 | 2641-4599 of SEQ ID NO:12 |
| 1-1809 of SEQ ID NO:12 | 1810-2640 of SEQ ID NO: 15 | 1810-2640 of SEQ ID NO: 15 | 2641-4599 of SEQ ID NO:12 |
| 1-1809 of SEQ ID NO:12 | SEQ ID NO: 18 | SEQ ID NO: 18 | 1-1809 of SEQ ID NO:12 |
| 1-1809 of SEQ ID NO:13 | 1810-2640 of SEQ ID NO: 12 | 1810-2640 of SEQ ID NO: 12 | 2641-4599 of SEQ ID NO: 13 |
| 1-1809 of SEQ ID NO:13 | 1810-2640 of SEQ ID NO: 13 | 1810-2640 of SEQ ID NO: 13 | 2641-4599 of SEQ ID NO: 13 |
| 1-1809 of SEQ ID NO:13 | 1810-2640 of SEQ ID NO: 14 | 1810-2640 of SEQ ID NO: 14 | 2641-4599 of SEQ ID NO: 13 |
| 1-1809 of SEQ ID NO:13 | 1810-2640 of SEQ ID NO: 15 | 1810-2640 of SEQ ID NO: 15 | 2641-4599 of SEQ ID NO: 13 |
| 1-1809 of SEQ ID NO:13 | SEQ ID NO: 18 | SEQ ID NO: 18 | 1-1809 of SEQ ID NO:13 |
| 1-1809 of SEQ ID NO:14 | 1810-2640 of SEQ ID NO: 12 | 1810-2640 of SEQ ID NO: 12 | 2641-4599 of SEQ ID NO: 14 |
| 2641-4599 of SEQ ID NO: 14 | 1810-2640 of SEQ ID NO: 13 | 1810-2640 of SEQ ID NO: 13 | 2641-4599 of SEQ ID NO: 14 |
| 1-1809 of SEQ ID NO:14 | 1810-2640 of SEQ ID NO: 14 | 1810-2640 of SEQ ID NO: 14 | 2641-4599 of SEQ ID NO: 14 |
| 1-1809 of SEQ ID NO:14 | 1810-2640 of SEQ ID NO: 15 | 1810-2640 of SEQ ID NO: 15 | 2641-4599 of SEQ ID NO: 14 |

-continued

| Nucleic acid encoding the N-terminal part of GDE | | Nucleic acid encoding the C-terminal part of GDE | |
| --- | --- | --- | --- |
| 1-1809 of SEQ ID NO:14 | SEQ ID NO: 18 | SEQ ID NO: 18 | 2641-4599 of SEQ ID NO: 14 |
| 1-1809 of SEQ ID NO:15 | 1810-2640 of SEQ ID NO: 12 | 1810-2640 of SEQ ID NO: 12 | 2641-4599 of SEQ ID NO:15 |
| 2641-4599 of SEQ ID NO:15 | 1810-2640 of SEQ ID NO: 13 | 1810-2640 of SEQ ID NO: 13 | 2641-4599 of SEQ ID NO:15 |
| 2641-4599 of SEQ ID NO:15 | 1810-2640 of SEQ ID NO: 14 | 1810-2640 of SEQ ID NO: 14 | 2641-4599 of SEQ ID NO:15 |
| 2641-4599 of SEQ ID NO:15 | 1810-2640 of SEQ ID NO: 15 | 1810-2640 of SEQ ID NO: 15 | 2641-4599 of SEQ ID NO:15 |
| 1-1809 of SEQ ID NO: 15 | SEQ ID NO: 18 | SEQ ID NO: 18 | 2641-4599 of SEQ ID NO:15 |

12. The dual AAV vector system according to claim 11, wherein:
  a) the first AAV vector comprises a genome comprising, in the 5' to 3' orientation:
    a 5' ITR;
    a promoter optionally preceded by an enhancer;
    optionally, an intron;
    a nucleic acid sequence encoding a N-teiminal part of GDE selected in the group consisting of the nucleic acid sequences encoding a N-terminal part of GDE shown in table 2; and
    a 3'-ITR; and
  b) the second AAV vector comprises a genome comprising, in the 5' to 3' orientation:
    a 5' ITR;
    a nucleic acid sequence encoding a C-terminal part of GDE selected in the group consisting of the nucleic acid sequences encoding a C-terminal part of GDE shown in table 2;
    a polyadenylation signal; and
    a 3'-ITR

| Nucleic acid encoding the N-terminal part of GDE | | Nucleic acid encoding the C-terminal part of GDE | |
| --- | --- | --- | --- |
| 1-1692 of SEQ ID NO:12 | 1693-2688 of SEQ ID NO: 12 | 1693-2688 of SEQ ID NO: 12 | 2689-4599 of SEQ ID NO:12 |
| 1-1692 of SEQ ID NO:12 | 1693-2688 of SEQ ID NO: 13 | 1693-2688 of SEQ ID NO: 13 | 2689-4599 of SEQ ID NO:12 |
| 1-1692 of SEQ ID NO:12 | 1693-2688 of SEQ ID NO: 14 | 1693-2688 of SEQ ID NO: 14 | 2689-4599 of SEQ ID NO:12 |
| 1-1692 of SEQ ID NO:12 | 1693-2688 of SEQ ID NO: 15 | 1693-2688 of SEQ ID NO: 15 | 2689-4599 of SEQ ID NO:12 |
| 1-1692 of SEQ ID NO:13 | 1693-2688 of SEQ ID NO: 12 | 1693-2688 of SEQ ID NO: 12 | 2689-4599 of SEQ ID NO: 13 |
| 1-1692 of SEQ ID NO:13 | 1693-2688 of SEQ ID NO: 13 | 1693-2688 of SEQ ID NO: 13 | 2689-4599 of SEQ ID NO: 13 |
| 1-1692 of SEQ ID NO:13 | 1693-2688 of SEQ ID NO: 14 | 1693-2688 of SEQ ID NO: 14 | 2689-4599 of SEQ ID NO: 13 |
| 1-1692 of SEQ ID NO:13 | 1693-2688 of SEQ ID NO: 15 | 1693-2688 of SEQ ID NO: 15 | 2689-4599 of SEQ ID NO: 13 |
| 1-1692 of SEQ ID NO:14 | 1693-2688 of SEQ ID NO: 12 | 1693-2688 of SEQ ID NO: 12 | 2689-4599 of SEQ ID NO: 14 |
| 1-1692 of SEQ ID NO:14 | 1693-2688 of SEQ ID NO: 13 | 1693-2688 of SEQ ID NO: 13 | 2689-4599 of SEQ ID NO: 14 |
| 1-1692 of SEQ ID NO:14 | 1693-2688 of SEQ ID NO: 14 | 1693-2688 of SEQ ID NO: 14 | 2689-4599 of SEQ ID NO: 14 |
| 1-1692 of SEQ ID NO:14 | 1693-2688 of SEQ ID NO: 15 | 1693-2688 of SEQ ID NO: 15 | 2689-4599 of SEQ ID NO: 14 |
| 1-1692 of SEQ ID NO:15 | 1693-2688 of SEQ ID NO: 12 | 1693-2688 of SEQ ID NO: 12 | 2689-4599 of SEQ ID NO:15 |
| 2689-4599 of SEQ ID NO:15 | 1693-2688 of SEQ ID NO: 13 | 1693-2688 of SEQ ID NO: 13 | 2689-4599 of SEQ ID NO:15 |
| 2689-4599 of SEQ ID NO:15 | 1693-2688 of SEQ ID NO: 14 | 1693-2688 of SEQ ID NO: 14 | 2689-4599 of SEQ ID NO:15 |
| 2689-4599 of SEQ ID NO:15 | 1693-2688 of SEQ ID NO: 15 | 1693-2688 of SEQ ID NO: 15 | 2689-4599 of SEQ ID NO:15 |
| 1-1809 of SEQ ID NO:12 | 1810-2640 of SEQ ID NO: 12 | 1810-2640 of SEQ ID NO: 12 | 2641-4599 of SEQ ID NO:12 |
| 1-1809 of SEQ ID NO:12 | 1810-2640 of SEQ ID NO: 13 | 1810-2640 of SEQ ID NO: 13 | 2641-4599 of SEQ ID NO:12 |
| 1-1809 of SEQ ID NO:12 | 1810-2640 of SEQ ID NO: 14 | 1810-2640 of SEQ ID NO: 14 | 2641-4599 of SEQ ID NO:12 |
| 1-1809 of SEQ ID NO:12 | 1810-2640 of SEQ ID NO: 15 | 1810-2640 of SEQ ID NO: 15 | 2641-4599 of SEQ ID NO:12 |
| 1-1809 of SEQ ID NO:12 | SEQ ID NO: 18 | SEQ ID NO: 18 | 1-1809 of SEQ ID NO:12 |
| 1-1809 of SEQ ID NO:13 | 1810-2640 of SEQ ID NO: 12 | 1810-2640 of SEQ ID NO: 12 | 2641-4599 of SEQ ID NO: 13 |
| 1-1809 of SEQ ID NO:13 | 1810-2640 of SEQ ID NO: 13 | 1810-2640 of SEQ ID NO: 13 | 2641-4599 of SEQ ID NO: 13 |

-continued

| Nucleic acid encoding the N-terminal part of GDE | | Nucleic acid encoding the C-terminal part of GDE | |
|---|---|---|---|
| 1-1809 of SEQ ID NO:13 | 1810-2640 of SEQ ID NO: 14 | 1810-2640 of SEQ ID NO: 14 | 2641-4599 of SEQ ID NO: 13 |
| 1-1809 of SEQ ID NO:13 | 1810-2640 of SEQ ID NO: 15 | 1810-2640 of SEQ ID NO: 15 | 2641-4599 of SEQ ID NO: 13 |
| 1-1809 of SEQ ID NO:13 | SEQ ID NO: 18 | SEQ ID NO: 18 | 1-1809 of SEQ ID NO:13 |
| 1-1809 of SEQ ID NO:14 | 1810-2640 of SEQ ID NO: 12 | 1810-2640 of SEQ ID NO: 12 | 2641-4599 of SEQ ID NO: 14 |
| 2641-4599 of SEQ ID NO: 14 | 1810-2640 of SEQ ID NO: 13 | 1810-2640 of SEQ ID NO: 13 | 2641-4599 of SEQ ID NO: 14 |
| 1-1809 of SEQ ID NO:14 | 1810-2640 of SEQ ID NO: 14 | 1810-2640 of SEQ ID NO: 14 | 2641-4599 of SEQ ID NO: 14 |
| 1-1809 of SEQ ID NO:14 | 1810-2640 of SEQ ID NO: 15 | 1810-2640 of SEQ ID NO: 15 | 2641-4599 of SEQ ID NO: 14 |
| 1-1809 of SEQ ID NO:14 | SEQ ID NO: 18 | SEQ ID NO: 18 | 2641-4599 of SEQ ID NO: 14 |
| 1-1809 of SEQ ID NO:15 | 1810-2640 of SEQ ID NO: 12 | 1810-2640 of SEQ ID NO: 12 | 2641-4599 of SEQ ID NO:15 |
| 2641-4599 of SEQ ID NO:15 | 1810-2640 of SEQ ID NO: 13 | 1810-2640 of SEQ ID NO: 13 | 2641-4599 of SEQ ID NO:15 |
| 2641-4599 of SEQ ID NO:15 | 1810-2640 of SEQ ID NO: 14 | 1810-2640 of SEQ ID NO: 14 | 2641-4599 of SEQ ID NO:15 |
| 2641-4599 of SEQ ID NO:15 | 1810-2640 of SEQ ID NO: 15 | 1810-2640 of SEQ ID NO: 15 | 2641-4599 of SEQ ID NO:15 |
| 1-1809 of SEQ ID NO:15 | SEQ ID NO: 18 | SEQ ID NO: 18 | 2641-4599 of SEQ ID NO:15 |

13. The dual AAV vector system according to claim 11, wherein:
   the nucleic acid sequence encoding the N-terminal part of GDE is the nucleotide sequence comprised between nucleotides 1 and 2688 of SEQ ID NO:13 or a corresponding optimized sequence; and
   the nucleic acid sequence encoding the C-terminal part of GDE is the nucleotide sequence comprised between nucleotides 1693 and 4599 of SEQ ID NO:13 or a corresponding optimized sequence.

14. The dual AAV vector system according to claim 11, wherein:
   the nucleic acid sequence encoding the N-terminal part of GDE is the nucleotide sequence comprised between nucleotides 1 and 2688 of SEQ ID NO:13 or a corresponding optimized sequence selected from SEQ ID NO:27 or SEQ ID NO:28; and
   the nucleic acid sequence encoding the C-terminal part of GDE is the nucleotide sequence comprised between nucleotides 1693 and 4599 of SEQ ID NO:13 or a corresponding optimized sequence selected from SEQ ID NO:29 or SEQ ID NO:30.

15. The dual AAV vector system according to claim 11, wherein:
   the nucleic acid sequence encoding the N-terminal part of GDE is the nucleotide sequence comprised between nucleotides 1 and 1809 of SEQ ID NO:13, or a corresponding optimized sequence selected from nucleotides 1-1809 of SEQ ID NO:25, 27 or 28; and
   the nucleic acid sequence encoding the C-teiminal part of GDE is the nucleotide sequence comprised between nucleotides 2641 and 4599 of SEQ ID NO:13, or a corresponding optimized sequence selected from nucleotides 949-2907 of SEQ ID NO:26, 29 or 30.

16. The dual AAV vector system according to claim 10, wherein:
   said promoter is a muscle-specific promoter, an ubiquitous promoter or a promoter directing expression in muscle and in liver cells; and/or
   said intron is selected in the group consisting of a human beta globin b2 intron, a FIX intron and a chicken beta-globin intron, wherein said intron is optionally a modified intron selected from a modified HBB2 intron of SEQ ID NO:9, a modified FIX intron of SEQ ID NO:10, or a modified chicken beta-globin intron of SEQ ID NO:11; and/or
   said polyadenylation signal is selected from the human beta globin polyadenylation signal, the bovine growth hormone polyadenylation signal, the SV40 polyadenylation signal, or another naturally occurring or artificial polyadenylation signal.

17. The dual AAV system according to claim 1, wherein each of said first and second AAV vectors is an AAV vector with an AAV-derived capsid.

18. A cell transduced with the dual AAV system according to claim 1.

19. A composition comprising, in a pharmaceutically acceptable carrier, the dual AAV system according to claim 1 or a cell comprising said dual AAV system.

20. A method of treating glycogen storage disease III comprising administering the dual AAV system according to claim 1 or a cell comprising said dual AAV system to a subject having glycogen storage disease III.

21. An AAV vector corresponding to the first or second AAV vector of the dual AAV vector system according to claim 1.

* * * * *

SEQUENCE LISTING

<160> NUMBER OF SEQ ID NOS: 36

<210> SEQ ID NO 1
<211> LENGTH: 865
<212> TYPE: DNA
<213> ORGANISM: Homo sapiens

<400> SEQUENCE: 1

```
ccccgggtgc gcggcgtcgg tggtgccggc gggggcgcc aggtcgcagg cggtgtaggg      60
ctccaggcag gcggcgaagg ccatgacgtg cgctatgaag gtctgctcct gcacgccgtg     120
aaccaggtgc gcctgcgggc cgcgcgcgaa caccgccacg tcctcgcctg cgtgggtctc     180
ttcgtccagg ggcactgctg actgctgccg atactcgggg ctcccgctct cgctctcggt     240
aacatccggc cgggcgccgt ccttgagcac atagcctgga ccgtttccgt ataggaggac     300
cgtgtaggcc ttcctgtccc gggccttgcc agcggccagc ccgatgaagg agctccctcg     360
```

```
caggggtag cctccgaagg agaagacgtg ggagtggtcg gcagtgacga ggctcagcgt    420
gtcctcctcg ctggtgagct ggcccgccct ctcaatggcg tcgtcgaaca tgatcgtctc    480
agtcagtgcc cggtaagccc tgctttcatg atgaccatgg tcgatgcgac caccctccac    540
gaagaggaag aagccgcggg ggtgtctgct cagcaggcgc agggcagcct ctgtcatctc    600
catcagggag gggtccagtg tggagtctcg gtggatctcg tatttcatgt ctccaggctc    660
aaagagaccc atgagatggg tcacagacgg gtccagggaa gcctgcatga gctcagtgcg    720
gttccacacg taccgggcac cctggcgttc gccgagccat tcctgcacca gattcttccc    780
gtccagcctg gtcccacctt ggctgtagtc atctgggtac tcagggtctg ggttcccat    840
gcgaaacatg tactttcggc ctcca                                         865

<210> SEQ ID NO 2
<211> LENGTH: 437
<212> TYPE: DNA
<213> ORGANISM: Homo sapiens

<400> SEQUENCE: 2
ccccgggtgc gcggcgtcgg tggtgccggc gggggcgcc aggtcgcagg cggtgtaggg     60
ctccaggcag gcggcgaagg ccatgacgtg cgctatgaag gtctgctcct gcacgccgtg    120
aaccaggtgc gcctgcgggc gcgcgcgaa caccgccacg tcctcgcctg cgtgggtctc    180
ttcgtccagg ggcactgctg actgctgccg atactcgggg ctcccgctct cgctctcggt    240
aacatccggc cgggcgccgt ccttgagcac atagcctgga ccgtttccgt ataggaggac    300
cgtgtaggcc ttcctgtccc gggccttgcc agcggccagc ccgatgaagg agctccctcg    360
caggggtag cctccgaagg agaagacgtg ggagtggtcg gcagtgacga ggctcagcgt     420
gtcctcctcg ctggtga                                                  437

<210> SEQ ID NO 3
<211> LENGTH: 428
<212> TYPE: DNA
<213> ORGANISM: Homo sapiens

<400> SEQUENCE: 3
gctggcccgc cctctcaatg gcgtcgtcga acatgatcgt ctcagtcagt gcccggtaag     60
ccctgctttc atgatgacca tggtcgatgc gaccaccctc cacgaagagg aagaagccgc    120
ggggggtgtct gctcagcagg cgcagggcag cctctgtcat ctccatcagg gaggggtcca    180
gtgtggagtc tcggtggatc tcgtatttca tgtctccagg ctcaaagaga cccatgagat    240
gggtcacaga cgggtccagg gaagcctgca tgagctcagt gcggttccac acgtaccggg    300
cacccctggcg ttcgccgagc cattcctgca ccagattctt cccgtccagc ctggtcccac    360
cttggctgta gtcatctggg tactcagggt ctggggttcc catgcgaaac atgtactttc    420
ggcctcca                                                            428

<210> SEQ ID NO 4
<211> LENGTH: 287
<212> TYPE: DNA
<213> ORGANISM: Homo sapiens

<400> SEQUENCE: 4
ccccgggtgc gcggcgtcgg tggtgccggc gggggcgcc aggtcgcagg cggtgtaggg     60
ctccaggcag gcggcgaagg ccatgacgtg cgctatgaag gtctgctcct gcacgccgtg    120
```

```
aaccaggtgc gcctgcgggc cgcgcgcgaa caccgccacg tcctcgcctg cgtgggtctc      180
ttcgtccagg ggcactgctg actgctgccg atactcgggg ctcccgctct cgctctcggt      240
aacatccggc cgggcgccgt ccttgagcac atagcctgga ccgtttc                    287
```

```
<210> SEQ ID NO 5
<211> LENGTH: 290
<212> TYPE: DNA
<213> ORGANISM: Homo sapiens

<400> SEQUENCE: 5
cgtataggag gaccgtgtag gccttcctgt cccgggcctt gccagcggcc agcccgatga      60
aggagctccc tcgcaggggg tagcctccga aggagaagac gtgggagtgg tcggcagtga     120
cgaggctcag cgtgtcctcc tcgctggtga gctggcccgc cctctcaatg cgtcgtcga      180 acatgatcgt ctcagtcagt gcccggtaag ccctgctttc atgatgacca tggtcgatgc     240 gaccacccctc cacgaagagg aagaagccgc gggggtgtct gctcagcagg               290
```

```
<210> SEQ ID NO 6
<211> LENGTH: 288
<212> TYPE: DNA
<213> ORGANISM: Homo sapiens

<400> SEQUENCE: 6
cgcagggcag cctctgtcat ctccatcagg gaggggtcca gtgtggagtc tcggtggatc      60
tcgtatttca tgtctccagg ctcaaagaga cccatgagat gggtcacaga cgggtccagg     120
gaagcctgca tgagctcagt gcggttccac acgtaccggg caccctggcg ttcgccgagc     180
cattcctgca ccagattctt cccgtccagc ctggtccac cttggctgta gtcatctggg      240
tactcagggt ctggggttcc catgcgaaac atgtactttc ggcctcca                  288
```

```
<210> SEQ ID NO 7
<211> LENGTH: 285
<212> TYPE: DNA
<213> ORGANISM: artificial
<220> FEATURE:
<223> OTHER INFORMATION: AP1

<400> SEQUENCE: 7
ccccgggtgc gcggcgtcgg tggtgccggc gggggcgcc aggtcgcagg cggtgtaggg       60
ctccaggcag gcggcgaagg ccatgacgtg cgctatgaag gtctgctcct gcacgccgtg     120
aaccagggcg cctgcgggcc gcgcgcgaac accgccacgt cctcgcctgc gtgggtctct     180
tcgtccaggg gcactgctga ctgctgccga tactcggggc tcccgctctc gctctcggta     240
acatccggcc gggcccgtcc ttgagcacat agcctggacc gtttc                     285
```

```
<210> SEQ ID NO 8
<211> LENGTH: 77
<212> TYPE: DNA
<213> ORGANISM: artificial
<220> FEATURE:
<223> OTHER INFORMATION: AK, F1 phage recombinogenic sequence

<400> SEQUENCE: 8
gggattttgc cgatttcggc ctattggtta aaaaatgagc tgatttaaca aaaatttaac     60
gcgaatttta acaaaat                                                    77
```

```
<210> SEQ ID NO 9
<211> LENGTH: 441
```

```
<212> TYPE: DNA
<213> ORGANISM: artificial
<220> FEATURE:
<223> OTHER INFORMATION: modified HBB2 intron

<400> SEQUENCE: 9
gtacacatat tgaccaaatc agggtaattt tgcatttgta attttaaaaa atgctttctt      60
cttttaatat acttttttgt ttatcttatt tctaatactt tccctaatct ctttctttca     120
gggcaataat gatacaatgt atcatgcctc tttgcaccat tctaaagaat aacagtgata     180
atttctgggt taaggcaata gcaatatttc tgcatataaa tatttctgca tataaattgt     240
aactgatgta agaggtttca tattgctaat agcagctaca atccagctac cattctgctt     300
ttattttctg gttgggataa ggctggatta ttctgagtcc aagctaggcc ttttgctaa      360 tcttgttcat acctcttatc ttcctcccac agctcctggg caacctgctg gtctctctgc     420
tggcccatca ctttggcaaa g                                               441

<210> SEQ ID NO 10
<211> LENGTH: 1438
<212> TYPE: DNA
<213> ORGANISM: artificial
<220> FEATURE:
<223> OTHER INFORMATION: modified FIX intron

<400> SEQUENCE: 10
ggtttgtttc cttttttaaa atacattgag tatgcttgcc ttttagatat agaaatatct      60
gatgctgtct tcttcactaa attttgatta catgatttga cagcaatatt gaagagtcta     120
acagccagca cgcaggttgg taagtactgg ttctttgtta gctaggtttt cttcttcttc     180
atttttaaaa ctaaatagat cgacattgct tttgttgcat ttatgtttaa taaacactgt     240
tcagttcatg atttggtcat gtaattcctg ttagaaaaca ttcatctcct tggtttaaaa     300
aaattaaaag tgggaaaaca aagaaatagc agaatatagt gaaaaaaaat aaccacatta     360
tttttgtttg gacttaccac tttgaaatca aattgggaaa caaaagcaca acaatggcc      420 ttatttacac aaaaagtctg attttaagat atatgacatt tcaaggtttc agaagtatgt     480
aatgaggtgt gtctctaatt ttttaaatta tatatcttca atttaaagtt ttagttaaaa     540
cataaagatt aacctttcat tagcaagctg ttagttatca ccaacgcttt tcatggatta     600
ggaaaaaatc attttgtctc tttgtcaaac atcttggagt tgatatttgg ggaaacacaa     660
tactcagttg agttccctag gggagaaaag cacgcttaag aattgacata agagtagga      720 agttagctat tgcaacatat atcactttgt ttttcacaa ctacagtgac ttttgtatt      780 tcccagagga aggcatacag ggaagaaatt atcccatttg acaaacagc ttgttctcac      840 aggaagcatt tatcacactt acttgtcaac tttctagaat caaatctagt agctgacagt     900
accaggatca ggggtgccaa ccctaagcac ccccagaaag ctgactggcc ctgtggttcc     960
cactccagac atgatgtcag ctgtgaaatc gacgtcgctg gaccataatt aggcttctgt    1020
tcttcaggag acatttgttc aaagtcattt gggcaaccat attctgaaaa cagcccagcc    1080
agggtgttgg atcactttgc aaagatcctc attgagctat tttcaagtgt tgacaaagtg    1140
tgaagttaac cgctcatttg agaactttct ttttcatcca agtaaattc aaatatgatt    1200 agaaatctga ccttttatta ctggaattct cttgactaaa agtaaaattg aattttaatt    1260
cctaaatctc catgtgtata cagtactgtg ggaacatcac agattttggc tccatgccct    1320
```

| aaagagaaat tggctttcag attatttgga ttaaaaacaa agactttctt aagagatgta | 1380 |
| aaattttctt gttgttttct tttttgctaa aactaaagaa ttattctttt acatttca | 1438 |

<210> SEQ ID NO 11
<211> LENGTH: 881
<212> TYPE: DNA
<213> ORGANISM: artificial
<220> FEATURE:
<223> OTHER INFORMATION: modified chicken beta globin intron

<400> SEQUENCE: 11

| gcgggagtcg ctgcgttgcc ttcgccccgt gccccgctcc gccgccgcct cgcgccgccc | 60 |
| gccccggctc tgactgaccg cgttactccc acaggtgagc gggcgggacg gcccttctcc | 120 |
| tccgggctgt aattagcgct tggtttaatg acggcttgtt tcttttctgt ggctgcgtga | 180 |
| aagccttgag gggctccggg agggccctttt gtgcgggggg agcggctcgg ggggtgcgtg | 240 |
| cgtgtgtgtg tgcgtgggga gcgccgcgtg cggctccgcg ctgcccggcg gctgtgagcg | 300 |
| ctgcgggcgc ggcgcggggc tttgtgcgct ccgcagtgtg cgcgagggga gcgcggccgg | 360 |
| gggcggtgcc ccgcggtgcg ggggggctg cgagggaac aaaggctgcg tgcggggtgt | 420 |
| gtgcgtgggg gggtgagcag ggggtgtggg cgcgtcggtc gggctgcaac ccccctgca | 480 |
| cccccctccc cgagttgctg agcacggcc ggcttcgggt gcggggctcc gtacggggcg | 540 |
| tggcgcgggg ctcgccgtgc cgggcggggg gtggcggcag gtgggggtgc cgggcggggc | 600 |
| ggggccgcct cgggccgggg agggctcggg ggagggggcgc ggcggccccc ggagcgccgg | 660 |
| cggctgtcga ggcgcggcga gccgcagcca ttgccttttt tggtaatcgt gcgagagggc | 720 |
| gcagggactt cctttgtccc aaatctgtgc ggagccgaaa tctgggaggc gccgccgcac | 780 |
| cccctctagc gggcgcgggg cgaagcggtg cggcgccggc aggaaggaat tgggcgggga | 840 |
| gggccttcgt gcgtcgccgc gccgccgtcc ccttctccct c | 881 |

<210> SEQ ID NO 12
<211> LENGTH: 4599
<212> TYPE: DNA
<213> ORGANISM: Homo sapiens

<400> SEQUENCE: 12

| atgggacaca gtaaacagat tcgaatttta cttctgaacg aaatggagaa actggaaaag | 60 |
| accctcttca gacttgaaca agggtatgag ctacagttcc gattaggccc aactttacag | 120 |
| ggaaaagcag ttaccgtgta tacaaattac ccatttcctg agaaacatt taatagagaa | 180 |
| aaattccgtt ctctggattg ggaaaatcca acagaaagag aagatgattc tgataaatac | 240 |
| tgtaaactta atctgcaaca atctggttca tttcagtatt atttccttca aggaaatgag | 300 |
| aaaagtggtg gaggttacat agttgtggac cccatttac gtgttggtgc tgataatcat | 360 |
| gtgctacccct tggactgtgt tactcttcag acatttttag ctaagtgttt gggaccttt | 420 |
| gatgaatggg aaagcagact tagggttgca aaagaatcag gctacaacat gattcatttt | 480 |
| accccattgc agactcttgg actatctagg tcatgctact cccttgccaa tcagttagaa | 540 |
| ttaaatcctg acttttcaag acctaataga agtatacct ggaatgatgt tggacagcta | 600 |
| gtggaaaaat taaaaaagga atggaatgtt atttgtatta ctgatgttgt ctacaatcat | 660 |
| actgctgcta atagtaaatg gatccaggaa catccagaat gtgcctataa tcttgtgaat | 720 |
| tctccacact taaaacctgc ctgggtctta gacagagcac tttggcgttt ctcctgtgat | 780 |

```
gttgcagaag ggaaatacaa agaaaaggga atacctgctt tgattgaaaa tgatcaccat    840
atgaattcca tccgaaaaat aatttgggag gatattttc caaagcttaa actctgggaa    900
tttttccaag tagatgtcaa caaagcggtt gagcaattta gaagacttct tacacaagaa   960
aataggcgag taaccaagtc tgatccaaac caacacctta cgattattca agatcctgaa  1020
tacagacggt ttggctgtac tgtagatatg aacattgcac taacgacttt cataccacat  1080 gacaagggc cagcagcaat tgaagaatgc tgtaattggt ttcataaaag aatggaggaa   1140
ttaaattcag agaagcatcg actcattaac tatcatcagg aacaggcagt taattgcctt  1200
ttgggaaatg tgttttatga acgactggct ggccatggtc caaaactagg acctgtcact  1260
agaaagcatc ctttagttac caggtatttt actttcccat tgaagagat agacttctcc   1320 atggaagaat ctatgattca tctgccaaat aaagcttgtt ttctgatggc acacaatgga  1380
tgggtaatgg gagatgatcc tcttcgaaac tttgctgaac cgggttcaga agtttaccta  1440
aggagagaac ttatttgctg gggagacagt gttaaattac gctatgggaa taaaccagag  1500
gactgtcctt atctctgggc acacatgaaa aaatacactg aaataactgc aacttatttc  1560
cagggagtac gtcttgataa ctgccactca acacctcttc acgtagctga gtacatgttg  1620
gatgctgcta ggaatttgca acccaattta tatgtagtag ctgaactgtt cacaggaagt  1680
gaagatctgg acaatgtctt tgttactaga ctgggcatta gttccttaat aagagaggca  1740
atgagtgcat ataatagtca tgaagaggc agattagttt accgatatgg aggagaacct   1800
gttggatcct ttgttcagcc ctgtttgagg cctttaatgc cagctattgc acatgccctg  1860
tttatggata ttacgcatga taatgagtgt cctattgtgc atagatcagc gtatgatgct  1920
cttccaagta ctacaattgt ttctatggca tgttgtgcta gtggaagtac aagaggctat  1980
gatgaattag tgcctcatca gatttcagtg gtttctgaag aacggtttta cactaagtgg  2040
aatcctgaag cattgccttc aaacacaggt gaagttaatt tccaaagcgg cattattgca  2100
gccaggtgtg ctatcagtaa acttcatcag gagcttggag ccaagggttt tattcaggtg  2160
tatgtggatc aagttgatga agacatagtg gcagtaacaa gacactcacc tagcatccat  2220
cagtctgttg tggctgtatc tagaactgct ttcaggaatc ccaagacttc attttacagc  2280
aaggaagtgc ctcaaatgtg catccctggc aaaattgaag aagtagttct tgaagctaga  2340
actattgaga gaaacacgaa accttatagg aaggatgaga attcaatcaa tggaacacca  2400
gatatcacag tagaaattag agaacatatt cagcttaatg aaagtaaaat tgttaaacaa  2460
gctggagttg ccacaaaagg gcccaatgaa tatattcaag aaatagaatt tgaaaacttg  2520
tctccaggaa gtgttattat attcagagtt agtcttgatc cacatgcaca agtcgctgtt  2580
ggaattcttc gaaatcatct gacacaattc agtcctcact ttaaatctgg cagcctagct  2640
gttgacaatg cagatcctat attaaaaatt ccttttgctt ctcttgcctc cagattaact  2700
ttggctgagc taaatcagat cctttaccga tgtgaatcag aagaaaagga agatggtgga  2760
gggtgctatg acataccaaa ctggtcagcc cttaaatatg caggtcttca aggtttaatg  2820
tctgtattgg cagaaataag accaagaat gacttggggc atccttttg taataatttg    2880 agatctggag attggatgat tgactatgtc agtaaccggc ttatttcacg atcaggaact  2940
attgctgaag ttggtaaatg gttgcaggct atgttcttct acctgaagca gatcccacgt  3000
taccttatcc catgttactt tgatgctata ttaattggtg catataccac tcttctggat  3060
acagcatgga agcagatgtc aagctttgtt cagaatggtt caacctttgt gaaacacctt  3120
tcattgggtt cagttcaact gtgtggagta ggaaaattcc cttccctgcc aattctttca  3180
```

-continued

```
cctgccctaa tggatgtacc ttataggtta aatgagatca caaaagaaaa ggagcaatgt    3240
tgtgtttctc tagctgcagg cttacctcat ttttcttctg gtattttccg ctgctgggga    3300
agggatactt ttattgcact tagaggtata ctgctgatta ctggacgcta tgtagaagcc    3360
aggaatatta ttttagcatt tgcgggtacc ctgaggcatg gtctcattcc taatctactg    3420
ggtgaaggaa tttatgccag atacaattgt cgggatgctg tgtggtggtg gctgcagtgt    3480
atccaggatt actgtaaaat ggttccaaat ggtctagaca ttctcaagtg cccagttttcc   3540 agaatgtatc ctacagatga ttctgctcct ttgcctgctg gcacactgga tcagccattg    3600
tttgaagtca tacaggaagc aatgcaaaaa cacatgcagg gcatacagtt ccgagaaagg    3660
aatgctggtc cccagataga tcgaaacatg aaggacgaag gttttaatat aactgcagga    3720
gttgatgaag aaacaggatt tgtttatgga ggaaatcgtt tcaattgtgg cacatggatg    3780
gataaaatgg gagaaagtga cagagctaga acagaggaa tcccagccac accaagagat     3840
gggtctgctg tggaaattgt gggcctgagt aaatctgctg ttcgctggtt gctggaatta    3900
tccaaaaaaa atattttccc ttatcatgaa gtcacagtaa aaagacatgg aaaggctata    3960
aaggtctcat atgatgagtg aacagaaaa atacaagaca actttgaaaa gctatttcat     4020
gtttccgaag acccttcaga tttaaatgaa aagcatccaa atctggttca caaacgtggc    4080
atatacaaag atagttatgg agcttcaagt ccttggtgtg actatcagct caggcctaat    4140
tttaccatag caatggttgt ggcccctgag ctctttacta cagaaaaagc atggaaagct    4200
ttggagattg cagaaaaaaa attgcttggt ccccttggca tgaaaacttt agatccagat    4260
gatatggttt actgtggaat ttatgacaat gcattagaca atgacaacta caatcttgct    4320
aaaggtttca attatcacca aggacctgag tggctgtggc ctattgggta ttttcttcgt    4380
gcaaaattat attttttccag attgatgggc ccggagacta ctgcaaagac tatagttttg    4440
gttaaaaatg ttcttttcccg acattatgtt catcttgaga gatcccctttg gaaaggactt   4500 ccagaactga ccaatgagaa tgcccagtac tgtccttttca gctgtgaaac acaagcctgg   4560
tcaattgcta ctattcttga gacactttat gatttatag                           4599
```

<210> SEQ ID NO 13
<211> LENGTH: 4599
<212> TYPE: DNA
<213> ORGANISM: artificial
<220> FEATURE:
<223> OTHER INFORMATION: GDE wtGNT

<400> SEQUENCE: 13

```
atgggacaca gtaaacagat tcgaattta cttctgaacg aaatggagaa actggaaaag      60 acctcttca gacttgaaca agggtatgag ctacagttcc gattaggccc aactttacag     120
ggaaaagcag ttaccgtgta tacaaattac ccatttcctg agaaacatt taatagagaa     180 aaattccgtt ctctggattg gaaaatcca acagaaagag aagatgattc tgataaatac    240
tgtaaactta atctgcaaca atctggttca tttcagtatt atttccttca aggaaatgag    300
aaaagtggtg gaggttacat agttgtggac cccatttac gtgttggtgc tgataatcat    360
gtgctaccct tggactgtgt tactcttcag acatttttag ctaagtgttt gggaccttt     420 gatgaatggg aaagcagact tagggttgca aaagaatcag gctacaacat gattcatttt   480
accccattgc agactcttgg actatctagg tcatgctact cccttgccaa tcagttagaa   540
ttaaatcctg acttttcaag acctaataga aagtatacct ggaatgatgt tggacagcta   600
```

```
gtggaaaaat taaaaaagga atggaatgtt atttgtatta ctgatgttgt ctacaatcat    660
actgctgcta atagtaaatg gatccaggaa catccagaat gtgcctataa tcttgtaaat    720
tctccacact taaaacctgc ctgggtctta gacagagcac tttggcgttt ctcctgtgat    780
gttgcagaag ggaaatacaa agaaaaggga atacctgctt tgattgaaaa tgatcaccat    840
atgaactcca tccgaaaaat aatttgggag atattttc caaagcttaa actctgggaa      900 ttttccaag tagatgtcaa caaagcggtt gagcaattta aagacttct tacacaagaa      960 aataggcgag taaccaagtc tgatccaaac caacaccta cgattattca agatcctgaa    1020
tacagacggt ttggctgtac tgtagatatg aacattgcac taacgacttt cataccacat   1080 gacaagggc cagcagcaat tgaagaatgc tgtaattggt ttcataaaag aatggaggaa    1140
ttaaattcag agaagcatcg actcattaac tatcatcagg aacaggcagt taattgcctt   1200
ttgggaaatg tgttttatga acgactggct ggccatggtc caaaactagg acctgtcact   1260
agaaagcatc ctttagttac caggtatttt actttcccat ttgaagagat agacttctcc   1320
atggaagaat ctatgattca tctgccaaat aaagcttgtt ttctgatggc acacaatgga   1380
tgggtaatgg gagatgatcc tcttcgaaac tttgctgaac cggggttcaga agtttaccta   1440 aggagagaac ttatttgctg gggagacagt gttaaattac gctatgggaa taaaccagag   1500
gactgtcctt atctctgggc acacatgaaa aaatacactg aaataactgc aacttatttc   1560
cagggagtac gtcttgataa ctgccactca acacctcttc acgtagctga gtacatgttg   1620
gatgctgcta ggaatttgca acccaattta tatgtagtag ctgaactgtt cacaggaagt   1680
gaggacctag acaatgtctt tgttactaga ctgggcatta gttccttaat aagagaggca   1740
atgagtgcat ataatagtca tgaagagggc agattagttt accgatatgg aggagaacct   1800
gttggatcct ttgttcagcc ctgtttgagg ccttttaatgc cagctattgc acatgccctg   1860
tttatggata ttacgcatga taatgagtgt cctattgtgc atagatcagc gtatgatgct   1920
cttccaagta ctacaattgt ttctatggca tgttgtgcta gtggaagtac aagaggctat   1980
gatgaattag tgcctcatca gatttcagtg gtttctgaag aacggtttta cactaagtgg   2040
aatcctgaag cattgccttc aaacacaggt gaagttaatt tccaaagcgg cattattgca   2100
gccaggtgtg ctatcagtaa acttcatcag gagcttggag ccaagggttt tattcaggtg   2160
tatgtggatc aagttgatga agacatagtg gcagtaacaa gacactcacc tagcatccat   2220
cagtctgttg tggctgtaac tagaactgct ttcaggaatc ccaagacttc attttacagc   2280
aaggaagtgc ctcaaatgtg catccctggc aaaattgaag aagtagttct tgaagctaga   2340
actattgaga gaaacacgaa accttatagg aaggatgaaa attcaatcaa tggaacacca   2400
gatatcacag tagaaattag agaacatatt cagcttaatg aaagtaaaat tgttaaacaa   2460
gctggagttg ccacaaaagg gcccaatgaa tatattcaag aaatagaatt tgaaaacttg   2520
tctccaggaa gtgttattat attcagagtt agtcttgatc cacatgcaca agtcgctgtt   2580
ggcattcttc gaaatcatct gacacaattc agtcctcact ttaaatctgg cagcctagct   2640
gttgacaatg cagatcctat attaaaaatt ccttttgctt ctcttgccta tagattaact   2700
ttggctgagc taaatcagat cctttaccga tgtgaatcag aagaaaagga agatggtgga   2760
gggtgctatg acataccaaa ctggtcagcc cttaaatatg caggtcttca aggtttaatg   2820
tctgtattgg cagaaataag accaaagaat gacttggggc atccttttg taataatttg   2880 aggtctggag attggatgat tgactatgtc agtaaccggc ttatttcacg atcaggaact   2940
attgctgaag ttggtaaatg gttgcaggct atgttcttct acctgaagca gatcccacgt   3000
```

```
tacctatcc catgttactt tgatgctata ttaattggtg catataccac tcttctggat    3060
acagcatgga agcagatgtc aagctttgtt cagaatggtt caacctttgt gaaacacctt    3120
tcattgggtt cagttcaact gtgtggagta ggaaaattcc cttccctgcc aattctttca    3180
cctgccctaa tggatgtacc ttataggtta aatgagatca caaaagaaaa ggagcaatgt    3240
tgtgtttctc tagctgcagg cttacctcat ttttcttctg gtattttccg ctgctgggga    3300
agggatactt ttattgcact tagaggtata ctgctgatta ctggacgcta tgtagaagcc    3360
aggaatatta ttttagcatt tgcgggtacc ctgaggcatg gtctcattcc taatctactg    3420
ggtgaaggaa tttatgccag atacaattgt cgggatgctg tgtggtggtg gctgcagtgt    3480
atccaggatt actgtaaaat ggttccaaat ggactagaca ttctcaagtg cccagtttcc    3540
agaatgtatc ctacagatga ttctgctcct ttgcctgctg gcacactgga tcagccattg    3600
tttgaagtca tacaggaagc aatgcaaaaa cacatgcagg gcatacagtt ccgagaaagg    3660
aatgctggtc cccagataga tcgaaacatg aaggacgaag gttttaatat aactgcagga    3720
gttgatgaag aaacaggatt tgtttatgga ggaaatcgtt tcaattgtgg cacatggatg    3780
gataaaatgg gagaaagtga cagagctaga acagaggaa tcccagccac accaagagat    3840
gggtctgctg tggaaattgt gggcctgagt aaatctgctg ttcgctggtt gctggaatta    3900
tccaaaaaaa atattttccc ttatcatgaa gtcacagtaa aaagacatgg aaaggctata    3960
aaggtctcat atgatgagtg aacagaaaa atacaagaca actttgaaaa gctatttcat    4020
gtttccgaag acccttcaga tttaaatgaa aagcatccaa atctggttca caaacgtggc    4080
atatacaaag atagttatgg agcttcaagt ccttggtgtg actatcagct caggcctaat    4140
tttaccatag caatggttgt ggcccctgag ctctttacta cagaaaaagc atggaaagct    4200
ttggagattg cagaaaaaaa attgcttggt ccccttggca tgaaaacttt agatccagat    4260
gatatggttt actgtggaat ttatgacaac gcattagaca tgacaacta caatcttgct    4320 aaaggtttca attatcacca aggacctgag tggctgtggc tattgggta ttttcttcgt    4380 gcaaaattat attttcccag attgatgggc ccggagacta ctgcaaagac tatagttttg    4440
gttaaaaatg ttctttcccg acattatgtt catcttgaga gatcccttg gaaggaactt    4500 ccagaactga ccaatgagaa tgcccagtac tgtccttca gctgtgaaac acaagcctgg    4560
tcaattgcta ctattcttga gacactttat gatttatag                          4599
```

<210> SEQ ID NO 14
<211> LENGTH: 4599
<212> TYPE: DNA
<213> ORGANISM: artificial
<220> FEATURE:
<223> OTHER INFORMATION: GDEco1 (entire sequence)

<400> SEQUENCE: 14

```
atgggccata gtaaacagat tcgcatactc ctcttgaacg agatggagaa actggagaag      60
acattgtttc ggttggagca ggggtacgag ctccagtttc gcctgggacc gacgctccaa     120
ggcaaagctg tgactgtata cacgaactat ccattcccgg gggagacgtt taacagggag     180
aagtttaggt ccctggactg ggagaaccca accgaacgag gaggacgattc cgataaatat    240 tgcaagctca acttgcagca aagtggcagc tttcaatatt actttctcca aggcaatgag    300
aaaagtgggg ggggtatat tgttgtcgat ccaatactgc gcgtaggggc agataatcac    360
gttctcccgc tggattgcgt cactctccag acattcttgg ctaaatgctt ggggccgttt    420
```

```
gatgaatggg agtctcgctt gcgagtggcc aaagagtcag gttataacat gattcacttc      480
acaccactcc agacattggg acttagtcgg agctgttact cactcgcaaa tcaattggag      540
cttaacccag acttcagtcg gccaaatcgg aagtacacgt ggaacgacgt tggacaactt      600
gtcgaaaagt tgaagaaaga gtggaatgtg atttgcatca ctgacgtggt gtacaatcac      660
accgcagcca acagcaagtg gattcaggag cacccagagt gtgcgtacaa cctggtgaac      720
tcacctcacc tcaaacccgc ctgggtgctc gatagggctt tgtggcgctt ttcttgcgac      780
gtagcggaag gaaagtataa agagaaagga atacccgccc tcatagaaaa cgatcatcac      840
atgaattcta tacggaaaat catctgggag gatatatttc cgaaacttaa actttgggag      900
ttctttcaag tagatgtaaa caaggcggtg gagcaattca ggaggctcct cacccaagag      960
aatcgccggg ttactaaatc tgacccgaat caacaccta caataatcca agatccggaa     1020
tacaggaggt ttggttgcac tgtcgatatg aatattgcgc ttactacgtt catcccccac     1080
gacaagggcc cggccgcaat agaagaatgc tgcaattggt tccacaagcg gatggaagaa     1140
ctgaactctg aaaagcaccg ccttataaat tatcaccaag agcaggctgt gaactgtctg     1200
ctcggtaacg tttttacga gcgcctggcc ggacacggac ctaaactcgg gccagtcact     1260
cgaaaacacc cactggttac gcgatacttc acattcccgt tcgaggagat cgacttttct     1320
atggaggaat ctatgatcca cctcccaaat aaagcttgtt ttcttatggc gcacaacgga     1380
tgggttatgg gggacgaccc actgcgaaac ttcgcagaac cgggtagtga ggtctacctt     1440
aggcgcgagc tcatttgttg gggcgacagc gtcaagctcc ggtatggaaa taagccagag     1500
gattgccctt acttgtgggc acacatgaag aagtatacgg aaataacagc tacctacttc     1560
cagggggtac gactggataa ctgccactcc acaccgttgc acgtggccga gtatatgctc     1620
gacgctgcgc gcaatttgca gccaaatctg tacgtcgtgg cagagctttt cactggaagt     1680
gaggacttgg ataacgtctt tgtgactcgc ctgggaatta gtagcttgat aagggaggct     1740
atgtccgcgt acaacagtca cgaggaagga cgattggttt atcgatatgg gggcgagcct     1800
gtaggctcct ttgtgcaacc ctgcttgcgg ccccttatgc ccgctatagc acacgcgctc     1860
ttcatggata tcacgcacga taatgaatgc cccatagtac acagatccgc ctacgacgcc     1920
cttccatcta cgacaatcgt ctctatggcc tgctgcgcct ccggcagcac tagaggctac     1980
gacgaactcg tcccacacca gatttcagtg gtatcgagag aacggtttta cactaaatgg     2040
aaccctgagg cgctcccatc taatactggc gaagtaaatt tccagtccgg aatcattgcg     2100
gcccgctgtg ctatctccaa gttgcatcag gaacttggag ctaaaggttt cattcaagta     2160
tatgtcgatc aggtcgatga agatattgtg gctgtgaccc gacactcccc atcaattcat     2220
caaagtgtag tggctgtaac tcggacggct tttcgcaacc caaagacttc attctactcc     2280
aaagaggttc cacagatgtg tattccggga aagatagaag aagtggtatt ggaagcccgg     2340
accatcgaga ggaacactaa accatatcga aaagacgaga actccattaa cggaaccccct     2400 gacatcactg ttgagatccg cgagcatatt cagcttaacg aaagcaaaat cgttaagcag     2460
gccggcgttg ccactaaggg accaaacgaa tatatccaag aaatcgaatt cgaaaacctc     2520
agtcctggct ccgttattat cttcgcgta tccctcgacc cacacgccca agttgcggta     2580
gggatcttga gaaaccacct cacacagttc agcccacact ttaaatcagg ctccctcgcc     2640
gttgataacg cggacccaat acttaagatc ccctttgcat cccttgcgta tcgacttact     2700
ctcgcagagc ttaatcaaat attgtaccgc tgcgagtccg aagagaagga agacggtggt     2760
ggctgctacg acatccctaa ttggagtgca cttaagtacg cggggctgca gggactgatg     2820
```

```
tcagtgcttg cagagataag gccgaagaat gaccttggcc atccattttg taataatctc   2880
cgaagtggtg attggatgat agattacgta tcaaaccgct tgatcagtcg gtctggtacc   2940
atcgcggaag tgggaaagtg gttgcaggca atgttctttt atctcaaaca aatcccacgg   3000
tacttgatac cttgctattt cgacgcaatt ctcatcggtg catacacgac cttgctggac   3060
acggcctgga agcagatgtc tagcttcgtt cagaacggtt ctaccttcgt aaagcacctc   3120
tcattgggtt cagtccaact ctgcggagtc gggaaattcc cttcacttcc tattctctca   3180
cctgccctca tggacgtgcc ctaccggctg aacgaaatta ctaaggagaa ggaacagtgt   3240
tgtgtttctt tggcggcagg cttgccgcac ttttccagtg gaatcttcag atgttgggga   3300
cgggacacat tcattgcgct ccggggtatt tgttgataac ggccgata cgttgaggca   3360 cgaaatatta ttctggcatt cgccgggacc ttgcggcacg ggctgatacc caacctgctg   3420
ggcgaaggga tttacgctcg ctataactgc cgagacgcag tttggtggtg gctgcagtgt   3480
attcaggact attgtaagat ggtaccgaac gggctcgaca tcttgaagtg tcccgttagt   3540
cgaatgtatc ccaccgacga ttcagctccc ctgcccgcgg aacacttga ccaaccactc   3600 tttgaagtga tccaagaggc tatgcagaaa cacatgcagg aatacagtt ccgagaacga   3660 aacgcagggc cgcagattga tcgaaatatg aaagacgaag gattttaatat cacggcaggg   3720 gtcgacgaag agacggggtt tgtctacggc gggaatagat ttaactgcgg cacctggatg   3780
gataaaatgg gagaaagtga ccgagcacgg aaccggggca taccagcaac cccccgagac   3840
gggagcgctg ttgagatcgt gggtctgtct aagagtgcgg ttcgctggct tctcgagctt   3900
tcaaaaaaaa atatatttcc ttaccacgag gtcacggtca aaaggcatgg aaaagccata   3960
aaagtgtcat acgacgagtg gaataggaaa atacaagata actttgaaaa gctgtttcac   4020
gttagcgaag atcccagcga tctcaacgaa aaacatccca atctggttca caaacgcggg   4080
atctataaag actcatatgg agctagttct ccttggtgcg attatcaact gagaccgaac   4140
tttacaatcg ccatggtagt tgcgcccgag ctctttacta cagaaaaagc ctggaaggca   4200
cttgagattg cggaaaagaa actgcttggc cctctcggga tgaaaacgct tgatcccgac   4260
gacatggtct attgcgggat ttacgacaac gcattggaca acgacaacta caacttggcg   4320
aaaggattta attatcacca gggtcctgag tggttgtggc ccattggata ctttcttcga   4380
gcgaagctgt attttttcaag gctgatgggg ccggaaacga cagcgaaaac tattgtgctt   4440
gtcaaaaacg tgcttagcag gcattacgtg cacctcgagc gcagcccttg aaaggactt   4500 ccggagctta cgaacgaaaa cgcccagtat tgtccattta gctgtgagac gcaggcctgg   4560
tctattgcta ccatcctcga gacactctac gacttgtag                         4599
```

<210> SEQ ID NO 15  
<211> LENGTH: 4599  
<212> TYPE: DNA  
<213> ORGANISM: artificial  
<220> FEATURE:  
<223> OTHER INFORMATION: GDEco2 (entire sequence)

<400> SEQUENCE: 15

```
atgggccaca gcaagcagat cagaatcctg ctgctgaacg agatggaaaa gctggaaaag    60
accctgttcc ggctcgagca gggctacgag ctgcagttta gactgggccc tacactgcag   120
ggcaaagccg tgaccgtgta cacaaaactac cccttccctg cgaaaccctt caaccgcgag   180
aagttcagaa gcctggactg ggagaacccc accgagagag aggacgacag cgacaagtac   240
```

```
tgcaagctga acctgcagca gagcggctcc ttccagtact acttcctgca aggcaacgag    300
aagtccggcg gaggctacat cgtggtggac cctattctga gagtgggcgc cgacaatcac    360
gtgctgcctc tggattgtgt gaccctgcag accttcctgg ccaagtgtct gggccctttc    420
gatgagtggg agagcagact gcgcgtggcc aaagaaagcg gctacaacat gatccacttc    480 accccctctgc agaccctggg cctgagcaga agctgttaca gcctggccaa ccagctggaa    540
ctgaaccccg acttcagcag acccaaccgg aagtacacct ggaacgatgt gggccagctg    600
gtggaaaaac tgaagaaaga tggaacgtg atctgcatca ccgacgtggt gtacaaccac    660
accgccgcca acagcaagtg gatccaagag caccctgagt gcgcctacaa cctggtcaac    720
agccctcacc tgaaacctgc ctgggtgctc gatagagccc tgtggcggtt tagctgtgat    780
gtggccgagg gcaagtacaa agagaagggc atccccgctc tgatcgagaa cgaccaccac    840
atgaacagca tccggaagat catctgggaa gatattttcc ccaagctgaa gctgtgggag    900
ttcttccagg tggacgtgaa caaggccgtg aacagttca gacggctgct gacccaagag    960
aacagaagag tgaccaagag cgaccccaac cagcacctga ccatcattca ggaccccgag   1020
tatcggagat tcggctgcac cgtggacatg aatatcgccc tgaccacctt cattccccac   1080
gacaaaggac ctgccgccat cgaggaatgc tgcaactggt ccacaagcg gatggaagaa   1140 ttgaacagcg agaagcaccg gctgatcaac taccaccaag agcaggccgt gaactgcctg   1200
ctgggcaacg tgttctatga gagactggcc ggacacggcc taagctggg acctgtgaca   1260 agaaagcacc ctctggttac ccggtacttc acctttccat cgaagagat cgacttctcc   1320 atggaagaga gcatgatcca tctgcctaac aaggcctgct tcctgatggc tcacaacggc   1380
tgggttatgg gcgacgaccc tctgagaaat tcgccgagc ctggcagcga ggtgtacctg   1440
agaagagaac tgatctgttg gggcgacagc gtgaagctga gatacggcaa caagcccgag   1500 gactgcccttt acctgtgggc ccatatgaag aagtacacag agatcaccgc cacctacttt   1560
cagggcgtca gactggacaa ctgccacagc acacctctgc acgtggccga gtacatgctg   1620
gacgccgcta gaaatctgca gcccaacctg tatgtggtgg ccgagctgtt taccggctcc   1680
gaggacctgg acaatgtgtt cgtgaccaga ctgggcatca gcagcctgat cagagaagcc   1740
atgtccgcct acaatagcca cgaagagggc agactggtgt acagatatgg cggcgagcct   1800
gtgggcagct tcgttcagcc ttgtctgagg cctctgatgc ccgccattgc tcacgccctg   1860
ttcatggaca tcacccacga taacgagtgc cccatcgtgc acagaagcgc ctacgacgct   1920
ctgcctagca ccaccattgt gtccatggcc tgttgtgcca gcggcagcac aagaggctat   1980
gacgaactgg tgccccacca gatttccgtg gtgtccgagg aacggttcta caccaagtgg   2040
aaccccgagg ctctgcccag caataccggc gaagtgaatt ccagagcgg catcattgcc   2100 gccagatgcg ccatcagcaa gctgcaccaa gaactgggcg ccaagggctt cattcaggtg   2160
tacgtggacc aggtcgacga ggacattgtg ccgtgacaa gacacagccc cagcatccat   2220
cagagcgtgg tggctgtgac cagaaccgcc ttcagaaacc ccaagaccag cttctacagc   2280
aaagaggtgc cccagatgtg catccccggc aagattgagg aagtggtgct cgaggcccgg   2340
accatcgaga gaaacaccaa gccttaccgg aaggacgaga actccatcaa cggcacccct   2400
gacatcaccg tggaaatcag agagcacatc cagctcaacg agcaagat cgtgaaacag   2460 gccggcgtgg ccacaaaggg ccccaacgag tatatccaag agattgagtt cgagaatctg   2520
agccccggca gcgtgatcat cttcagagtg tccctggatc ctcacgctca ggtggccgtg   2580
ggcatcctga gaaatcacct gacacagttc agcccacact tcaagagcgg aagcctggcc   2640
```

-continued

```
gtggacaacg ccgatcctat cctgaagatc cccttcgcct ctctggccta cagactgaca      2700
ctggctgagc tgaaccagat cctgtacaga tgcgagtccg aagagaaaga ggatggcgga      2760
ggctgctacg acatccccaa ttggagcgcc ctgaagtatg ccggactgca gggactgatg      2820
tctgtgctgg ccgagatcag acccaagaac gacctgggac acccttctg caacaacctg       2880 agatccggcg actggatgat cgactacgtg tccaacagac tgatcagcag atccggcaca      2940
atcgccgaag tcggcaaatg gctgcaggcc atgttcttct acctgaagca gatccctcgg      3000
tatctgatcc cctgctactt cgacgccatc ctgatcggcg cctacaccac actgctggat      3060
accgcctgga agcagatgtc cagcttcgtg cagaacggca gcaccttcgt gaagcacctg      3120
tctctgggaa gcgtgcagct gtgtggcgtg ggcaaatttc ccagcctgcc tatcctgtct      3180
cctgcactga tggacgtgcc ctaccggctg aatgagatca ccaaagaaaa agagcagtgc      3240
tgcgtcagcc tggctgctgg cctgcctcat ttttccagcg gcatcttccg gtgttgggc       3300 agagacacct ttattgccct gagaggcatc ctgctgatta ccggcagata cgtggaagcc      3360
cggaacatca tcctggcctt tgccggcaca ctgcggcacg gactgattcc taatctgctc      3420
ggcgagggca tctacgccag atacaactgc agagatgccg tgtggtggtg gctccagtgc      3480
atccaggact actgcaagat ggtgcccaac ggcctggaca tcctgaagtg ccctgtgtcc      3540
agaatgtacc ctaccgacga tagcgcccct ctgcctgccg gaacacttga ccagcctctg      3600
ttcgaagtga ttcaagaggc catgcagaaa cacatgcagg gaatccagtt cgcgagcgg       3660 aatgccggac ctcagatcga cagaaacatg aaggatgagg gcttcaacat caccgctggc      3720
gtggacgaag agacaggctt tgtgtacggc ggcaaccggt tcaattgcgg cacctggatg      3780
gacaagatgg gcgagtctga ccgggccaga aacagaggaa ttcccgccac acctagagat      3840
ggcagcgctg tggaaatcgt gggcctgtct aagtctgctg tgcggtggct gctcgaactg      3900
agcaagaaga atatctttcc gtaccacgaa gtgaccgtga agcggcacgg caaggccatc      3960
aaggtgtcct acgacgagtg gaacagaaag atccaggaca cttcgaaaa gctgttccat       4020 gtgtctgagg acccccagcga cctgaacgaa agcacccca acctggtgca agcgcggc       4080 atctacaagg acagctacgg cgcctcttct ccttggtgcg attaccagct gcggcccaac      4140
ttcaccattg ccatggtggt tgcccctgag ctgttcacca cagagaaggc ctggaaggcc      4200
ctggaaatcg ccgagaagaa actgctgggc cctctgggca tgaagacact ggaccccgac      4260
gacatggtgt actgcggaat ctacgacaac gccctggata cgacaacta caatctggcc       4320 aagggggttca attaccatca gggacccgag tggctgtggc ctatcggcta tttcctgcgg      4380
gccaagctgt acttctccag actgatgggc cctgagacaa ccgccaagac aatcgtgctc      4440
gtgaagaacg tgctgagccg gcactatgtg cacctggaaa gaagcccctg gaagggactg      4500
cccgagctga ccaatgagaa cgcccagtac tgcccttca gctgcgaaac acaggcctgg       4560
tctatcgcca ccatcctgga aaccctgtac gacctgtga                             4599
```

<210> SEQ ID NO 16
<211> LENGTH: 831
<212> TYPE: DNA
<213> ORGANISM: artificial
<220> FEATURE:
<223> OTHER INFORMATION: RRco1

<400> SEQUENCE: 16

```
ttcgtgcaac cctgccttag gccgttgatg ccagcgattg cccatgctct tttcatggac    60
ataactcacg acaacgagtg tcccatcgtg catcggagtg cttatgacgc cctcccatcc    120
acgaccatcg taagcatggc ttgttgcgcc agcggatcta ctcgaggata tgacgaactg    180
gtccctcatc aaataagcgt ggtgtcagaa gagaggtttt acaccaaatg gaaccccgag    240
gcgcttccga gcaatacagg tgaggttaac ttccaatctg gaataattgc tgctcgatgt    300
gcaatcagca aacttcatca agagctcggt gcaaagggct ttatccaagt ttatgttgac    360
caggtagatg aggacatagt tgcagtgact cgccactcac cctcaataca tcaatccgtc    420
gtagctgtat cacgcacggc tttcagaaac cccaaaactt cctttattc aaaagaagtg    480
ccgcaaatgt gtatccccgg taaaatagag gaagttgtcc tcgaagcaag aacgatagag    540
aggaatacaa aaccttatcg aaaggacgaa aacagcatta acggaacgcc cgacattact    600
gtggagatcc gcgaacatat ccagcttaac gaaagtaaga tcgtaaagca agcaggagtc    660
gctactaaag gtcctaatga gtacatccaa gaaatagagt tcgagaatct ctcacccggt    720
tcagttatta ttttcagggt aagcctggat cctcatgcac aggtggcagt aggaatcctt    780
aggaatcatc tgacacaatt cagtccccac tttaaatctg gatcattggc t             831
```

<210> SEQ ID NO 17
<211> LENGTH: 831
<212> TYPE: DNA
<213> ORGANISM: artificial
<220> FEATURE:
<223> OTHER INFORMATION: RRco2

<400> SEQUENCE: 17

```
ttcgtgcagc cttgtctgag gcctctgatg ccgccattg ctcacgccct gttcatggac    60
atcacccacg acaacgagtg ccccatcgtg cacagatccg cctatgatgc cctgcctagc    120
accaccatcg tgtccatggc ttgttgtgcc agcggcagca ccagaggcta tgatgaactg    180
gtgccccacc agatcagcgt ggtgtccgag gaacggttct acaccaagtg gaaccccgag    240
gctctgccca gcaataccgg cgaagtgaat ttccagagcg catcattgc cgccagatgc    300
gccatcagca agctgcacca agagctggga gccaagggct tcatccaggt gtacgtggac    360
caggtggacg aggacattgt ggccgtgaca agacacagcc ccagcatcca tcagtctgtg    420
gtggccgtgt ccagaaccgc cttcagaaac cccaagacca gcttctacag caaagaggtg    480
ccccagatgt gcatccccgg caagattgag gaagtggtgc tggaagcccg gaccatcgag    540
agaaacacca gccttaccg gaaggacgag aacagcatca acggcacccc tgacatcacc    600
gtggaaatca gagagcacat ccagctgaac gagagcaaga tcgtgaagca ggctggcgtg    660
gccacaaagg gccccaacga gtacatccaa gagatcgagt tcgagaatct gagccccggc    720
agcgtgatca tcttcagagt gtccctggat cctcacgctc aggtggcagt gggcatcctg    780
agaaaccacc tgacacagtt cagccctcac ttcaagtctg gcagcctggc t             831
```

<210> SEQ ID NO 18
<211> LENGTH: 831
<212> TYPE: DNA
<213> ORGANISM: artificial
<220> FEATURE:
<223> OTHER INFORMATION: RRco3

```
<400> SEQUENCE: 18
ttcgtgcagc cctgcctgcg cccctgatg cccgccatcg cccacgccct gttcatggac      60
atcacccacg acaacgagtg ccccatcgtg caccgcagcg cctacgacgc cctgcccagc    120
accaccatcg tgagcatggc ctgctgcgcc agcggcagca cccgcggcta cgacgagctg    180
gtgccccacc agatcagcgt ggtgagcgag gagcgcttct acaccaagtg gaaccccgag    240
gccctgccca gcaacaccgg cgaggtgaac ttccagagcg gcatcatcgc cgcccgctgc    300
gccatcagca agctgcacca ggagctgggc gccaagggct tcatccaggt gtacgtggac    360
caggtggacg aggacatcgt ggccgtgacc cgccacagcc ccagcatcca ccagagcgtg    420
gtggccgtga gccgcaccgc cttccgcaac cccaagacca gcttctacag caaggaggtg    480
ccccagatgt gcatccccgg caagatcgag gaggtggtgc tggaggcccg caccatcgag    540
cgcaacacca gccctaccg caaggacgag aacagcatca acggcacccc cgacatcacc    600
gtggagatcc gcgagcacat ccagctgaac gagagcaaga tcgtgaagca ggccggcgtg    660
gccaccaagg cccccaacga gtacatccag gagatcgagt cgagaacct gagccccggc    720 agcgtgatca tcttccgcgt gagcctggac ccccacgccc aggtggccgt gggcatcctg    780
cgcaaccacc tgacccagtt cagcccccac ttcaagagcg gcagcctggc c            831

<210> SEQ ID NO 19
<211> LENGTH: 831
<212> TYPE: DNA
<213> ORGANISM: artificial
<220> FEATURE:
<223> OTHER INFORMATION: RRwt (1810-2640)

<400> SEQUENCE: 19
tttgttcagc cctgtttgag gcctttaatg ccagctattg cacatgccct gtttatggat     60
attacgcatg ataatgagtg tcctattgtg catagatcag cgtatgatgc tcttccaagt    120
actacaattg tttctatggc atgttgtgct agtggaagta caagaggcta tgatgaatta    180
gtgcctcatc agatttcagt ggtttctgaa gaacggtttt acactaagtg gaatcctgaa    240
gcattgcctt caaacacagg tgaagttaat ttccaaagcg gcattattgc agccaggtgt    300
gctatcagta aacttcatca ggagcttgga gccaagggtt ttattcaggt gtatgtggat    360
caagttgatg aagacatagt ggcagtaaca agacactcac ctagcatcca tcagtctgtt    420
gtggctgtaa ctagaactgc tttcaggaat cccaagactt cattttacag caaggaagtg    480
cctcaaatgt gcatccctgg caaaattgaa gaagtagttc ttgaagctag aactattgag    540
agaaacacga aaccttatag gaaggatgaa aattcaatca atggaacacc agatatcaca    600
gtagaaatta gagaacatat tcagcttaat gaaagtaaaa ttgttaaaca agctggagtt    660
gccacaaaag ggcccaatga atatattcaa gaaatagaat ttgaaaactt gtctccagga    720
agtgttatta tattcagagt tagtcttgat ccacatgcac aagtcgctgt tggcattctt    780
cgaaatcatc tgacacaatt cagtcctcac tttaaatctg gcagcctagc t            831

<210> SEQ ID NO 20
<211> LENGTH: 397
<212> TYPE: DNA
<213> ORGANISM: artificial
<220> FEATURE:
<223> OTHER INFORMATION: hAAT promoter
```

<400> SEQUENCE: 20

```
gatcttgcta ccagtggaac agccactaag gattctgcag tgagagcaga gggccagcta    60
agtggtactc tcccagagac tgtctgactc acgccacccc ctccaccttg gacacaggac   120
gctgtggttt ctgagccagg tacaatgact cctttcggta agtgcagtgg aagctgtaca   180
ctgcccaggc aaagcgtccg ggcagcgtag gcgggcgact cagatcccag ccagtggact   240
tagcccctgt ttgctcctcc gataactggg gtgaccttgg ttaatattca ccagcagcct   300
cccccgttgc ccctctggat ccactgctta atacggacg aggacagggc cctgtctcct   360
cagcttcagg caccaccact gacctgggac agtgaat                            397
```

<210> SEQ ID NO 21
<211> LENGTH: 321
<212> TYPE: DNA
<213> ORGANISM: artificial
<220> FEATURE:
<223> OTHER INFORMATION: ApoE control region

<400> SEQUENCE: 21

```
aggctcagag gcacacagga gtttctgggc tcaccctgcc cccttccaac ccctcagttc    60
ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctgggcaga ggtcagagac ctctctgggc ccatgccacc    240
tccaacatcc actcgacccc ttggaatttc ggtggagagg agcagaggtt gtcctggcgt   300
ggtttaggta gtgtgagagg g                                             321
```

<210> SEQ ID NO 22
<211> LENGTH: 441
<212> TYPE: DNA
<213> ORGANISM: artificial
<220> FEATURE:
<223> OTHER INFORMATION: HBB2 intron

<400> SEQUENCE: 22

```
gtacacatat tgaccaaatc agggtaattt tgcatttgta attttaaaaa atgctttctt    60
cttttaatat actttttgt ttatcttatt tctaatactt tccctaatct ctttctttca   120
gggcaataat gatacaatgt atcatgcctc tttgcaccat tctaaagaat aacagtgata   180
atttctgggt taaggcaata gcaatatttc tgcatataaa tatttctgca tataaattgt   240
aactgatgta agaggtttca tattgctaat agcagctaca atccagctac cattctgctt   300
ttattttatg gttgggataa ggctggatta ttctgagtcc aagctaggcc cttttgctaa   360
tcatgttcat acctcttatc ttcctcccac agctcctggg caacgtgctg gtctgtgtgc   420
tggcccatca ctttggcaaa g                                             441
```

<210> SEQ ID NO 23
<211> LENGTH: 1438
<212> TYPE: DNA
<213> ORGANISM: artificial
<220> FEATURE:
<223> OTHER INFORMATION: FIX intron

<400> SEQUENCE: 23

```
ggtttgtttc cttttttaaa atacattgag tatgcttgcc ttttagatat agaaatatct    60
gatgctgtct tcttcactaa attttgatta catgatttga cagcaatatt gaagagtcta   120
```

| | |
|---|---|
| acagccagca cgcaggttgg taagtactgg ttctttgtta gctaggtttt cttcttcttc | 180 |
| attttaaaa ctaaatagat cgacaatgct tatgatgcat ttatgtttaa taaacactgt | 240 |
| tcagttcatg atttggtcat gtaattcctg ttagaaaaca ttcatctcct tggtttaaaa | 300 |
| aaattaaaag tgggaaaaca aagaaatagc agaatatagt gaaaaaaaat aaccacatta | 360 |
| tttttgtttg gacttaccac tttgaaatca aatgggaaa caaaagcaca acaatggcc | 420 |
| ttatttacac aaaaagtctg attttaagat atatgacatt tcaaggtttc agaagtatgt | 480 |
| aatgaggtgt gtctctaatt ttttaaatta tatatcttca atttaaagtt ttagttaaaa | 540 |
| cataaagatt aacctttcat tagcaagctg ttagttatca ccaacgcttt tcatggatta | 600 |
| ggaaaaaatc attttgtctc tatgtcaaac atcttggagt tgatatttgg ggaaacacaa | 660 |
| tactcagttg agttccctag gggagaaaag cacgcttaag aattgacata aagagtagga | 720 |
| agttagctaa tgcaacatat atcactttgt tttttcacaa ctacagtgac tttatgtatt | 780 |
| tcccagagga aggcatacag ggaagaaatt atcccatttg acaaacagc atgttctcac | 840 |
| aggaagcatt tatcacactt acttgtcaac tttctagaat caaatctagt agctgacagt | 900 |
| accaggatca ggggtgccaa ccctaagcac ccccagaaag ctgactggcc ctgtggttcc | 960 |
| cactccagac atgatgtcag ctgtgaaatc gacgtcgctg gaccataatt aggcttctgt | 1020 |
| tcttcaggag acatttgttc aaagtcattt gggcaaccat attctgaaaa cagcccagcc | 1080 |
| agggtgatgg atcactttgc aaagatcctc aatgagctat tttcaagtga tgacaaagtg | 1140 |
| tgaagttaac cgctcatttg agaacttct ttttcatcca agtaaattc aaatatgatt | 1200 |
| agaaatctga cctttatta ctggaattct cttgactaaa agtaaaattg aattttaatt | 1260 |
| cctaaatctc catgtgtata cagtactgtg ggaacatcac agattttggc tccatgccct | 1320 |
| aaagagaaat tggctttcag attatttgga ttaaaaacaa agactttctt aagagatgta | 1380 |
| aaattttcat gatgttttct tttttgctaa aactaaagaa ttattctttt acatttca | 1438 |

<210> SEQ ID NO 24
<211> LENGTH: 881
<212> TYPE: DNA
<213> ORGANISM: artificial
<220> FEATURE:
<223> OTHER INFORMATION: chicken beta-globin intron

<400> SEQUENCE: 24

| | |
|---|---|
| gcgggagtcg ctgcgttgcc ttcgccccgt gccccgctcc gccgccgcct cgcgccgccc | 60 |
| gccccggctc tgactgaccg cgttactccc acaggtgagc gggcgggacg gcccttctcc | 120 |
| tccgggctgt aattagcgct tggtttaatg acggcttgtt tcttttctgt ggctgcgtga | 180 |
| aagccttgag gggctccggg agggcccttt gtgcgggggg agcggctcgg gggtgcgtg | 240 |
| cgtgtgtgtg tgcgtgggga cgccgcgtg cggctccgcg ctgcccggcg ctgtgagcg | 300 |
| ctgcgggcgc ggcgcggggc tttgtgcgct ccgcagtgtg cgcgagggga gcgcggccgg | 360 |
| gggcggtgcc ccgcggtgcg ggggggctg cgagggggaac aaaggctgcg tgcggggtgt | 420 |
| gtgcgtgggg gggtgagcag ggggtgtggg cgcgtcggtc gggctgcaac ccccctgca | 480 |
| cccccctccc cgagttgctg agcacggcc ggcttcgggt gcggggctcc gtacggggcg | 540 |
| tggcgcgggg ctcgccgtgc cgggcggggg gtggcggcag gtgggggtgc cggcggggc | 600 |
| ggggccgcct cgggccgggg agggctcggg ggaggggcgc ggcggccccc ggagcgccgg | 660 |
| cggctgtcga ggcgcggcga gccgcagcca ttgcctttta tggtaatcgt gcgagagggc | 720 |
| gcagggactt cctttgtccc aaatctgtgc ggagccgaaa tctgggaggc gccgccgcac | 780 |

```
cccctctagc gggcgcgggg cgaagcggtg cggcgccggc aggaaggaaa tgggcgggga    840
gggccttcgt gcgtcgccgc gccgccgtcc ccttctccct c                       881

<210> SEQ ID NO 25
<211> LENGTH: 2688
<212> TYPE: DNA
<213> ORGANISM: artificial
<220> FEATURE:
<223> OTHER INFORMATION: GDEwt HEAD

<400> SEQUENCE: 25
atgggacaca gtaaacagat tcgaatttta cttctgaacg aaatggagaa actggaaaag     60
accctcttca gacttgaaca agggtatgag ctacagttcc gattaggccc aactttacag    120
ggaaaagcag ttaccgtgta tacaaattac ccatttcctg agaaacatt taatagagaa     180 aaattccgtt ctctggattg ggaaaatcca acagaaagag aagatgattc tgataaatac    240
tgtaaactta atctgcaaca atctggttca tttcagtatt atttccttca aggaaatgag    300
aaaagtggtg gaggttacat agttgtggac cccatttac gtgttggtgc tgataatcat    360
gtgctaccct tggactgtgt tactcttcag acattttag ctaagtgttt gggaccttt     420 gatgaatggg aaagcagact tagggttgca aaagaatcag gctacaacat gattcatttt   480
accccattgc agactcttgg actatctagg tcatgctact cccttgccaa tcagttagaa    540
ttaaatcctg acttttcaag acctaataga agtatacct ggaatgatgt tggacagcta    600
gtggaaaaat taaaaaagga atggaatgtt atttgtatta ctgatgttgt ctacaatcat    660
actgctgcta atagtaaatg gatccaggaa catccagaat gtgcctataa tcttgtaaat    720
tctccacact taaaacctgc ctgggtctta gacagagcac tttggcgttt ctcctgtgat    780
gttgcagaag ggaaatacaa agaaaaggga atacctgctt tgattgaaaa tgatcaccat    840
atgaactcca tccgaaaaat aatttgggag atattttc caaagcttaa actctgggaa    900 ttttccaag tagatgtcaa caaagcggtt gagcaattta agagacttct tacacaagaa    960
aataggcgag taaccaagtc tgatccaaac caacaccta cgattattca agatcctgaa   1020
tacagacggt ttggctgtac tgtagatatg aacattgcac taacgacttt cataccacat   1080
gacaaggggc cagcagcaat tgaagaatgc tgtaattggt tcataaaag aatggaggaa   1140 ttaaattcag agaagcatcg actcattaac tatcatcagg aacaggcagt taattgcctt   1200
ttgggaaatg tgttttatga cgactggct ggccatggtc caaaactagg acctgtcact   1260
agaaagcatc ctttagttac caggtatttt actttcccat tgaagagat agacttctcc   1320 atggaagaat ctatgattca tctgccaaat aaagcttgtt ttctgatggc acacaatgga   1380
tgggtaatgg gagatgatcc tcttcgaaac tttgctgaac cggttcaga agtttaccta   1440 aggagagaac ttatttgctg gggagacagt gttaaattac gctatgggaa taaaccagag   1500
gactgtcctt atctctgggc acacatgaaa aaatacactg aaataactgc aacttatttc   1560
cagggagtac gtcttgataa ctgccactca acacctcttc acgtagctga gtacatgttg   1620
gatgctgcta ggaatttgca acccaattta tatgtagtag ctgaactgtt cacaggaagt   1680
gaggacctag acaatgtctt tgttactaga ctgggcatta gttccttaat aagagaggca   1740
atgagtgcat ataatagtca tgaagagggc agattagttt accgatatgg aggagaacct   1800
gttggatcct tgttcagcc ctgtttgagg cctttaatgc cagctattgc acatgccctg   1860
tttatggata ttacgcatga taatgagtgt cctattgtgc atagatcagc gtatgatgct   1920
```

| | |
|---|---|
| cttccaagta ctacaattgt ttctatggca tgttgtgcta gtggaagtac aagaggctat | 1980 |
| gatgaattag tgcctcatca gatttcagtg gtttctgaag aacggtttta cactaagtgg | 2040 |
| aatcctgaag cattgccttc aaacacaggt gaagttaatt tccaaagcgg cattattgca | 2100 |
| gccaggtgtg ctatcagtaa acttcatcag gagcttggag ccaagggttt tattcaggtg | 2160 |
| tatgtggatc aagttgatga agacatagtg gcagtaacaa gacactcacc tagcatccat | 2220 |
| cagtctgttg tggctgtaac tagaactgct ttcaggaatc ccaagacttc attttacagc | 2280 |
| aaggaagtgc ctcaaatgtg catccctggc aaaattgaag aagtagttct tgaagctaga | 2340 |
| actattgaga gaaacacgaa accttatagg aaggatgaaa attcaatcaa tggaacacca | 2400 |
| gatatcacag tagaaattag agaacatatt cagcttaatg aaagtaaaat tgttaaacaa | 2460 |
| gctggagttg ccacaaaagg gcccaatgaa tatattcaag aaatagaatt tgaaaacttg | 2520 |
| tctccaggaa gtgttattat attcagagtt agtcttgatc cacatgcaca agtcgctgtt | 2580 |
| ggcattcttc gaaatcatct gacacaattc agtcctcact ttaaatctgg cagcctagct | 2640 |
| gttgacaatg cagatcctat attaaaaatt ccttttgctt ctcttgcc | 2688 |

<210> SEQ ID NO 26
<211> LENGTH: 2907
<212> TYPE: DNA
<213> ORGANISM: artificial
<220> FEATURE:
<223> OTHER INFORMATION: GDEwt TAIL

<400> SEQUENCE: 26

| | |
|---|---|
| aatgtctttg ttactagact gggcattagt tccttaataa gagaggcaat gagtgcatat | 60 |
| aatagtcatg aagagggcag attagtttac cgatatggag gagaacctgt tggatccttt | 120 |
| gttcagccct gtttgaggcc tttaatgcca gctattgcac atgccctgtt tatggatatt | 180 |
| acgcatgata atgagtgtcc tattgtgcat agatcagcgt atgatgctct tccaagtact | 240 |
| acaattgttt ctatggcatg ttgtgctagt ggaagtacaa gaggctatga tgaattagtg | 300 |
| cctcatcaga tttcagtggt ttctgaagaa cggttttaca ctaagtggaa tcctgaagca | 360 |
| ttgccttcaa acacaggtga agttaatttc caaagcggca ttattgcagc caggtgtgct | 420 |
| atcagtaaac ttcatcagga gcttggagcc aagggtttta ttcaggtgta tgtggatcaa | 480 |
| gttgatgaag acatagtggc agtaacaaga cactcaccta gcatccatca gtctgttgtg | 540 |
| gctgtaacta gaactgcttt caggaatccc aagacttcat tttacagcaa ggaagtgcct | 600 |
| caaatgtgca tccctggcaa aattgaagaa gtagttcttg aagctagaac tattgagaga | 660 |
| aacacgaaac cttataggaa ggatgaaaat tcaatcaatg gaacaccaga tatcacagta | 720 |
| gaaattagag aacatattca gcttaatgaa agtaaaattg ttaaacaagc tggagttgcc | 780 |
| acaaaagggc ccaatgaata tattcaagaa atagaatttg aaaacttgtc tccaggaagt | 840 |
| gttattatat tcagagttag tcttgatcca catgcacaag tcgctgttgg cattcttcga | 900 |
| aatcatctga cacaattcag tcctcacttt aaatctggca gcctagctgt tgacaatgca | 960 |
| gatcctatat taaaaattcc ttttgcttct cttgcctata gattaacttt ggctgagcta | 1020 |
| aatcagatcc tttaccgatg tgaatcagaa gaaaaggaag atggtggagg tgctatgac | 1080 |
| ataccaaact ggtcagccct taaatatgca ggtcttcaag gtttaatgtc tgtattggca | 1140 |
| gaaataagac caaagaatga cttggggcat cctttttgta ataatttgag gtctggagat | 1200 |
| tggatgattg actatgtcag taaccggctt atttcacgat caggaactat tgctgaagtt | 1260 |
| ggtaaatggt tgcaggctat gttcttctac ctgaagcaga tcccacgtta ccttatccca | 1320 |

-continued

```
tgttactttg atgctatatt aattggtgca tataccactc ttctggatac agcatggaag    1380
cagatgtcaa gctttgttca gaatggttca acctttgtga acacctttc attgggttca    1440 gttcaactgt gtggagtagg aaaattccct tccctgccaa ttctttcacc tgccctaatg    1500
gatgtacctt ataggttaaa tgagatcaca aagaaaagg agcaatgttg tgtttctcta    1560
gctgcaggct tacctcattt ttcttctggt attttccgct gctggggaag ggatactttt    1620
attgcactta gaggtatact gctgattact ggacgctatg tagaagccag gaatattatt    1680
ttagcatttg cgggtaccct gaggcatggt ctcattccta atctactggg tgaaggaatt    1740
tatgccagat acaattgtcg ggatgctgtg tggtggtggc tgcagtgtat ccaggattac    1800
tgtaaaatgg ttccaaatgg actagacatt ctcaagtgcc cagtttccag aatgtatcct    1860
acagatgatt ctgctccttt gcctgctggc acactggatc agccattgtt tgaagtcata    1920
caggaagcaa tgcaaaaaca catgcagggc atacagttcc gagaaaggaa tgctggtccc    1980
cagatagatc gaaacatgaa ggacgaaggt tttaatataa ctgcaggagt tgatgaagaa    2040
acaggatttg tttatggagg aaatcgtttc aattgtggca catggatgga taaaatggga    2100
gaaagtgaca gagctagaaa cagaggaatc ccagccacac aagagatgg gtctgctgtg    2160 gaaattgtgg gcctgagtaa atctgctgtt cgctggttgc tggaattatc caaaaaaaat    2220
attttccctt atcatgaagt cacagtaaaa agacatggaa aggctataaa ggtctcatat    2280
gatgagtgga acagaaaaat acaagacaac tttgaaaagc tatttcatgt ttccgaagac    2340
ccttcagatt taaatgaaaa gcatccaaat ctggttcaca aacgtggcat atacaaagat    2400
agttatggag cttcaagtcc ttggtgtgac tatcagctca ggcctaattt taccatagca    2460
atggttgtgg cccctgagct ctttactaca gaaaaagcat ggaaagcttt ggagattgca    2520
gaaaaaaaat tgcttggtcc ccttggcatg aaaactttag atccagatga tatggtttac    2580
tgtggaattt atgacaacgc attagacaat gacaactaca atcttgctaa aggtttcaat    2640
tatcaccaag gacctgagtg gctgtggcct attgggtatt tcttcgtgc aaaattatat    2700 ttttccagat tgatgggccc ggagactact gcaaagacta tagttttggt taaaaatgtt    2760 cttttcccgac attatgttca tcttgagaga tccccttgga aaggacttcc agaactgacc    2820
aatgagaatg cccagtactg tcctttcagc tgtgaaacac aagcctggtc aattgctact    2880
attcttgaga cactttatga tttatag                                        2907
```

<210> SEQ ID NO 27
<211> LENGTH: 2688
<212> TYPE: DNA
<213> ORGANISM: artificial
<220> FEATURE:
<223> OTHER INFORMATION: GDEco1 HEAD

<400> SEQUENCE: 27

```
atgggccata gtaaacagat tcgcatactc ctcttgaacg agatggagaa actggagaag      60
acattgtttc ggttggagca ggggtacgag ctccagtttc gcctgggacc gacgctccaa     120
ggcaaagctg tgactgtata cacgaactat ccattcccgg gggagacgtt taacagggag     180
aagtttaggt ccctggactg ggagaaccca accgaacgag aggacgattc cgataaatat     240
tgcaagctca acttgcagca aagtggcagc tttcaatatt actttctcca aggcaatgag     300
aaaagtgggg gggggtatat tgttgtcgat ccaatactgc gcgtagggc agataatcac     360 gttctcccgc tggattgcgt cactctccag acattcttgg ctaaatgctt ggggccgttt    420
```

```
gatgaatggg agtctcgctt gcgagtggcc aaagagtcag gttataacat gattcacttc    480
acaccactcc agacattggg acttagtcgg agctgttact cactcgcaaa tcaattggag    540
cttaacccag acttcagtcg gccaaatcgg aagtacacgt ggaacgacgt tggacaactt    600
gtcgaaaagt tgaagaaaga gtggaatgtg atttgcatca ctgacgtggt gtacaatcac    660
accgcagcca acagcaagtg gattcaggag cacccagagt gtgcgtacaa cctggtgaac    720
tcacctcacc tcaaacccgc ctgggtgctc gatagggctt tgtggcgctt ttcttgcgac    780
gtagcggaag gaaagtataa agagaaagga atacccgccc tcatagaaaa cgatcatcac    840
atgaattcta tacggaaaat catctgggag gatatatttc cgaaacttaa actttgggag    900
ttcttttcaag tagatgtaaa caaggcggtg gagcaattca ggaggctcct cacccaagag    960
aatcgccggg ttactaaatc tgacccgaat caacaccta caataatcca agatccggaa    1020
tacaggaggt ttggttgcac tgtcgatatg aatattgcgc ttactacgtt catcccccac    1080
gacaagggcc cggccgcaat agaagaatgc tgcaattggt tccacaagcg gatggaagaa    1140
ctgaactctg aaaagcaccg ccttataaat tatcaccaag agcaggctgt gaactgtctg    1200
ctcggtaacg ttttttacga gcgcctggcc ggacacggac ctaaactcgg gccagtcact    1260
cgaaaacacc cactggttac gcgatacttc acattcccgt tcgaggagat cgactttttct    1320
atggaggaat ctatgatcca cctcccaaat aaagcttgtt ttcttatggc gcaacgga    1380
tgggttatgg gggacgaccc actgcgaaac ttcgcagaac cgggtagtga ggtctacctt    1440
aggcgcgagc tcatttgttg gggcgacagc gtcaagctcc ggtatggaaa taagccagag    1500
gattgccctt acttgtgggc acacatgaag aagtatacgg aaataacagc tacctacttc    1560
caggggtac gactggataa ctgccactcc acaccgttgc acgtggccga gtatatgctc    1620
gacgctgcgc gcaatttgca gccaaatctg tacgtcgtgg cagagctttt cactggaagt    1680
gaggacttgg ataacgtctt tgtgactcgc ctgggaatta gtagcttgat aagggaggct    1740
atgtccgcgt acaacagtca cgaggaagga cgattggttt atcgatatgg gggcgagcct    1800
gtaggctcct ttgtgcaacc ctgcttgcgg ccccttatgc ccgctatagc acacgcgctc    1860
ttcatggata tcacgcacga taatgaatgc cccatagtac acagatccgc ctacgacgcc    1920
cttccatcta cgacaatcgt ctctatggcc tgctgcgcct ccggcagcac tagaggctac    1980
gacgaactcg tcccacacca gatttcagtg gtatcagagg aacggtttta cactaaatgg    2040
aaccctgagg cgctcccatc taatactggc gaagtaaatt tccagtccgg aatcattgcg    2100
gcccgctgtg ctatctccaa gttgcatcag gaacttggag ctaaaggttt cattcaagta    2160
tatgtcgatc aggtcgatga agatattgtg gctgtgaccc gacactcccc atcaattcat    2220
caaagtgtag tggctgtaac tcggacggct tttcgcaacc caaagacttc attctactcc    2280
aaagaggttc cacagatgtg tattccggga aagatagaag aagtggtatt ggaagcccgg    2340
accatcgaga ggaacactaa accatatcga aagacgaga actccattaa cggaaccct    2400
gacatcactg ttgagatccg cgagcatatt cagcttaacg aaagcaaaat cgttaagcag    2460
gccggcgttg ccactaaggg accaaacgaa tatatccaag aaatcgaatt cgaaaacctc    2520
agtcctggct ccgttattat ctttcgcgta tccctcgacc cacacgccca agttgcggta    2580
gggatcttga gaaaccacct cacacagttc agcccacact ttaaatcagg ctccctcgcc    2640
gttgataacg cggacccaat acttaagatc cccttttgcat cccttgcg              2688

<210> SEQ ID NO 28
<211> LENGTH: 2688
```

<212> TYPE: DNA
<213> ORGANISM: artificial
<220> FEATURE:
<223> OTHER INFORMATION: GDEco2 HEAD

<400> SEQUENCE: 28

| | | | | | |
|---|---|---|---|---|---|
| atgggccaca | gcaagcagat | cagaatcctg | ctgctgaacg | agatggaaaa | gctggaaaag | 60 |
| accctgttcc | ggctcgagca | gggctacgag | ctgcagttta | gactgggccc | tacactgcag | 120 |
| ggcaaagccg | tgaccgtgta | cacaaactac | cccttccctg | cgaaaccttc | aaccgcgag | 180 |
| aagttcagaa | gcctggactg | ggagaacccc | accgagagag | aggacgacag | cgacaagtac | 240 |
| tgcaagctga | acctgcagca | gagcggctcc | ttccagtact | acttcctgca | aggcaacgag | 300 |
| aagtccggcg | gaggctacat | cgtggtggac | cctattctga | gagtgggcgc | cgacaatcac | 360 |
| gtgctgcctc | tggattgtgt | gaccctgcag | accttcctgg | ccaagtgtct | gggccctttc | 420 |
| gatgagtggg | agagcagact | gcgcgtggcc | aaagaaagcg | gctacaacat | gatccacttc | 480 |
| acccctctgc | agaccctggg | cctgagcaga | agctgttaca | gcctggccaa | ccagctggaa | 540 |
| ctgaaccccg | acttcagcag | acccaaccgg | aagtacacct | ggaacgatgt | gggccagctg | 600 |
| gtggaaaaac | tgaagaaaga | atggaacgtg | atctgcatca | ccgacgtggt | gtacaaccac | 660 |
| accgccgcca | cagcaagtg | atccaagag | caccctgagt | gcgcctacaa | cctggtcaac | 720 |
| agccctcacc | tgaaacctgc | ctgggtgctc | gatagagccc | tgtggcggtt | tagctgtgat | 780 |
| gtggccgagg | gcaagtacaa | agagaagggc | atccccgctc | tgatcgagaa | cgaccaccac | 840 |
| atgaacagca | tccggaagat | catctgggaa | gatattttcc | ccaagctgaa | gctgtgggag | 900 |
| ttcttccagg | tggacgtgaa | caaggccgtg | aacagttca | gacggctgct | gacccaagag | 960 |
| aacagaagag | tgaccaagag | cgaccccaac | cagcacctga | ccatcattca | ggaccccgag | 1020 |
| tatcggagat | cggctgcac | cgtggacatg | aatatcgccc | tgaccacctt | cattccccac | 1080 |
| gacaaaggac | ctgccgccat | cgaggaatgc | tgcaactggt | tccacaagcg | gatggaagaa | 1140 |
| ttgaacagcg | agaagcaccg | gctgatcaac | taccaccaag | agcaggccgt | gaactgcctg | 1200 |
| ctgggcaacg | tgttctatga | gagactggcc | ggacacggcc | taagctggg | acctgtgaca | 1260 |
| agaaagcacc | ctctggttac | ccggtacttc | acctttccat | cgaagagat | cgacttctcc | 1320 |
| atggaagaga | gcatgatcca | tctgcctaac | aaggcctgct | tcctgatggc | tcacaacggc | 1380 |
| tgggttatgg | gcgacgaccc | tctgagaaat | ttcgccgagc | ctggcagcga | ggtgtacctg | 1440 |
| agaagagaac | tgatctgttg | gggcgacagc | gtgaagctga | gatacggcaa | caagcccgag | 1500 |
| gactgccctt | acctgtgggc | ccatatgaag | aagtacacag | atcaccgc | cacctacttt | 1560 |
| cagggcgtca | gactggacaa | ctgccacagc | acacctctgc | acgtggccga | gtacatgctg | 1620 |
| gacgccgcta | gaaatctgca | gcccaacctg | tatgtggtgg | ccgagctgtt | taccggctcc | 1680 |
| gaggacctgg | acaatgtgtt | cgtgaccaga | ctgggcatca | gcagcctgat | cagagaagcc | 1740 |
| atgtccgcct | acaatagcca | cgaagagggc | agactggtgt | acagatatgg | cggcgagcct | 1800 |
| gtgggcagct | tcgttcagcc | ttgtctgagg | cctctgatgc | ccgccattgc | tcacgccctg | 1860 |
| ttcatggaca | tcacccacga | taacgagtgc | cccatcgtgc | acagaagcgc | ctacgacgct | 1920 |
| ctgcctagca | ccaccattgt | gtccatggcc | tgttgtgcca | gcggcagcac | aagaggctat | 1980 |
| gacgaactgg | tgccccacca | gatttccgtg | gtgtccgagg | aacggttcta | caccaagtgg | 2040 |
| aaccccgagg | ctctgcccag | caataccggc | gaagtgaatt | tccagagcgg | catcattgcc | 2100 |
| gccagatgcg | ccatcagcaa | gctgcaccaa | gaactgggcg | ccaagggctt | cattcaggtg | 2160 |

```
tacgtggacc aggtcgacga ggacattgtg gccgtgacaa gacacagccc cagcatccat    2220
cagagcgtgg tggctgtgac cagaaccgcc ttcagaaacc ccaagaccag cttctacagc    2280
aaagaggtgc cccagatgtg catccccggc aagattgagg aagtggtgct cgaggcccgg    2340
accatcgaga gaaacaccaa gccttaccgg aaggacgaga actccatcaa cggcacccct    2400
gacatcaccg tggaaatcag agagcacatc cagctcaacg agagcaagat cgtgaaacag    2460
gccggcgtgg ccacaaaggg ccccaacgag tatatccaag agattgagtt cgagaatctg    2520
agccccggca gcgtgatcat cttcagagtg tccctggatc ctcacgctca ggtggccgtg    2580
ggcatcctga gaaatcacct gacacagttc agcccacact tcaagagcgg aagcctggcc    2640
gtggacaacg ccgatcctat cctgaagatc cccttcgcct ctctggcc               2688
```

<210> SEQ ID NO 29
<211> LENGTH: 2907
<212> TYPE: DNA
<213> ORGANISM: artificial
<220> FEATURE:
<223> OTHER INFORMATION: GDEco1 TAIL

<400> SEQUENCE: 29

```
aacgtctttg tgactcgcct gggaattagt agcttgataa gggaggctat gtccgcgtac      60
aacagtcacg aggaaggacg attggtttat cgatatgggg gcgagcctgt aggctccttt     120
gtgcaaccct gcttgcggcc ccttatgccc gctatagcac acgcgctctt catggatatc     180
acgcacgata atgaatgccc catagtacac agatccgcct acgacgccct tccatctacg     240
acaatcgtct ctatggcctg ctgcgcctcc ggcagcacta gaggctacga cgaactcgtc     300
ccacaccaga tttcagtggt atcagaggaa cggttttaca ctaaatggaa ccctgaggcg     360
ctcccatcta atactggcga agtaaatttc cagtccggaa tcattgcggc ccgctgtgct     420
atctccaagt tgcatcagga acttggagct aaaggtttca ttcaagtata tgtcgatcag     480
gtcgatgaag atattgtggc tgtgacccga cactccccat caattcatca agtgtagtg      540 gctgtaactc ggacggcttt tcgcaaccca agacttcat tctactccaa agaggttcca      600
cagatgtgta ttccgggaaa gatagaagaa gtggtattgg aagcccggac catcgagagg     660
aacactaaac catatcgaaa agacgagaac tccattaacg gaaccctga catcactgtt      720 gagatccgcg agcatattca gcttaacgaa agcaaaatcg ttaagcaggc cggcgttgcc     780
actaagggac caaacgaata tatccaagaa atcgaattcg aaaacctcag tcctggctcc     840
gttattatct ttcgcgtatc cctcgaccca cacgcccaag ttgcggtagg gatcttgaga     900
aaccacctca cacagttcag cccacacttt aaatcaggct ccctcgccgt tgataacgcg     960
gacccaatac ttaagatccc cttttgcatcc cttgcgtatc gacttactct cgcagagctt    1020
aatcaaatat tgtaccgctg cgagtccgaa gagaaggaag acggtggtgg ctgctacgac    1080
atccctaatt ggagtgcact taagtacgcg gggctgcagg gactgatgtc agtgcttgca    1140
gagataaggc cgaagaatga ccttggccat ccatttttgta ataatctccg aagtggtgat   1200
tggatgatag attacgtatc aaaccgcttg atcagtcggt ctggtaccat cgcggaagtg    1260
ggaaagtggt tgcaggcaat gttctttttat ctcaaacaaa tcccacggta cttgatacct   1320
tgctatttcg acgcaattct catcggtgca tacacgacct tgctggacac ggcctggaag    1380
cagatgtcta gcttcgttca gaacggttct accttcgtaa agcacctctc attgggttca    1440
gtccaactct gcggagtcgg gaattccct tcacttccta ttctctcacc tgccctcatg     1500
gacgtgccct accggctgaa cgaaattact aaggagaagg aacagtgttg tgtttctttg   1560
```

```
gcggcaggct tgccgcactt ttccagtgga atcttcagat gttggggacg ggacacattc      1620
attgcgctcc ggggtatttt gttgataacg ggccgatacg ttgaggcacg aaatattatt      1680
ctggcattcg ccgggacctt gcggcacggg ctgatacccg acctgctggg cgaagggatt      1740
tacgctcgct ataactgccg agacgcagtt tggtggtggc tgcagtgtat tcaggactat      1800
tgtaagatgg taccgaacgg gctcgacatc ttgaagtgtc ccgttagtcg aatgtatccc      1860
accgacgatt cagctcccct gcccgcggga acacttgacc aaccactctt tgaagtgatc      1920
caagaggcta tgcagaaaca catgcaggga atacagttcc gagaacgaaa cgcagggccg      1980
cagattgatc gaaatatgaa agacgaagga tttaatatca cggcaggggt cgacgaagag      2040
acggggtttg tctacggcgg gaatagattt aactgcggca cctggatgga taaaatggga      2100
gaaagtgacc gagcacggaa ccggggcata ccagcaaccc cccgagacgg gagcgctgtt      2160
gagatcgtgg gtctgtctaa gagtgcggtt cgctggcttc tcgagctttc aaaaaaaaat      2220
atatttcctt accacgaggt cacggtcaaa aggcatggaa aagccataaa agtgtcatac      2280
gacgagtgga ataggaaaat acaagataac tttgaaaagc tgtttcacgt tagcgaagat      2340
cccagcgatc tcaacgaaaa acatcccaat ctggttcaca aacgcgggat ctataaagac      2400
tcatatggag ctagttctcc ttggtgcgat tatcaactga gaccgaactt tacaatcgcc      2460
atggtagttg cgcccgagct ctttactaca gaaaaagcct ggaaggcact tgagattgcg      2520
gaaaagaaac tgcttggccc tctcgggatg aaaacgcttg atcccgacga catggtctat      2580
tgcgggattt acgacaacgc attggacaac gacaactaca acttggcgaa aggatttaat      2640
tatcaccagg gtcctgagtg gttgtggccc attggatact ttcttcgagc gaagctgtat      2700
ttttcaaggc tgatggggcc ggaaacgaca gcgaaaacta ttgtgcttgt caaaaacgtg      2760
cttagcaggc attacgtgca cctcgagcgc agcccttgga aaggacttcc ggagcttacg      2820
aacgaaaacg cccagtattg tccatttagc tgtgagacgc aggcctggtc tattgctacc      2880
atcctcgaga cactctacga cttgtag                                         2907
```

<210> SEQ ID NO 30
<211> LENGTH: 2907
<212> TYPE: DNA
<213> ORGANISM: artificial
<220> FEATURE:
<223> OTHER INFORMATION: GDEco2 TAIL

<400> SEQUENCE: 30

```
aatgtgttcg tgaccagact gggcatcagc agcctgatca gagaagccat gtccgcctac       60
aatagccacg aagagggcag actggtgtac agatatggcg gcgagcctgt gggcagcttc      120
gttcagcctt gtctgaggcc tctgatgccc gccattgctc acgccctgtt catggacatc      180
acccacgata acgagtgccc catcgtgcac agaagcgcct acgacgctct gcctagcacc      240
accattgtgt ccatggcctg ttgtgccagc ggcagcacaa gaggctatga cgaactggtg      300
ccccaccaga tttccgtggt gtccgaggaa cggttctaca ccaagtggaa ccccgaggct      360
ctgcccagca ataccggcga agtgaatttc cagagcggca tcattgccgc cagatgcgcc      420
atcagcaagc tgcaccaaga actgggcgcc aagggcttca ttcaggtgta cgtggaccag      480
gtcgacgagg acattgtggc cgtgacaaga cacagcccca gcatccatca gagcgtggtg      540
gctgtgacca gaaccgccct cagaaacccc aagaccagct tctacagcaa agaggtgccc      600
cagatgtgca tccccggcaa gattgaggaa gtggtgctcg aggcccggac catcgagaga      660
```

```
aacaccaagc cttaccggaa ggacgagaac tccatcaacg gcacccctga catcaccgtg      720
gaaatcagag agcacatcca gctcaacgag agcaagatcg tgaaacaggc cggcgtggcc      780
acaaagggcc ccaacgagta tatccaagag attgagttcg agaatctgag ccccggcagc      840
gtgatcatct tcagagtgtc cctggatcct cacgctcagg tggccgtggg catcctgaga      900
aatcacctga cacagttcag cccacacttc aagagcggaa gcctggccgt ggacaacgcc      960
gatcctatcc tgaagatccc cttcgcctct ctggcctaca gactgacact ggctgagctg     1020
aaccagatcc tgtacagatg cgagtccgaa gagaagagg atggcggagg ctgctacgac     1080
atccccaatt ggagcgccct gaagtatgcc ggactgcagg gactgatgtc tgtgctggcc     1140
gagatcagac ccaagaacga cctgggacac cccttctgca caacctgag atccggcgac     1200
tggatgatcg actacgtgtc caacagactg atcagcagat ccggcacaat cgccgaagtc     1260
ggcaaatggc tgcaggccat gttcttctac ctgaagcaga tccctcggta tctgatcccc     1320
tgctacttcg acgccatcct gatcggcgcc tacaccacac tgctggatac cgcctggaag     1380
cagatgtcca gcttcgtgca gaacggcagc accttcgtga agcacctgtc tctgggaagc     1440
gtgcagctgt gtggcgtggg caaatttccc agcctgccta tcctgtctcc tgcactgatg     1500
gacgtgccct accggctgaa tgagatcacc aaagaaaaag agcagtgctg cgtcagcctg     1560
gctgctggcc tgcctcattt ttccagcggc atcttccggt gttggggcag agacaccttt     1620
attgccctga gaggcatcct gctgattacc ggcagatacg tggaagcccg aacatcatc     1680
ctggcctttg ccggcacact gcggcacgga ctgattccta atctgctcgg cgagggcatc     1740
tacgccagat acaactgcag agatgccgtg tggtggtggc tccagtgcat ccaggactac     1800
tgcaagatgg tgcccaacgg cctggacatc ctgaagtgcc ctgtgtccag aatgtaccct     1860
accgacgata gcgcccctct gcctgccgga acacttgacc agcctctgtt cgaagtgatt     1920
caagaggcca tgcagaaaca catgcaggga atccagtttc gcgagcggaa tgccggacct     1980
cagatcgaca gaaacatgaa ggatgagggc ttcaacatca ccgctggcgt ggacgaagag     2040
acaggctttg tgtacggcgg caaccggttc aattgcggca cctggatgga caagatgggc     2100
gagtctgacc gggccagaaa cagaggaatt cccgccacac ctagagatgg cagcgctgtg     2160
gaaatcgtgg gcctgtctaa gtctgctgtg cggtggctgc tcgaactgag caagaagaat     2220
atctttccgt accacgaagt gaccgtgaag cggcacggca aggccatcaa ggtgtcctac     2280
gacgagtgga acagaaagat ccaggacaac ttcgaaaagc tgttccatgt gtctgaggac     2340
cccagcgacc tgaacgaaaa gcaccccaac ctggtgcaca gcgcgggcat ctacaaggac     2400
agctacggcg cctcttctcc ttggtgcgat taccagctgc ggcccaactt caccattgcc     2460
atggtggttg cccctgagct gttcaccaca gagaaggcct ggaaggccct ggaaatcgcc     2520
gagaagaaac tgctgggccc tctgggcatg aagacactgg accccgacga catggtgtac     2580
tgcggaatct acgacaacgc cctggataac gacaactaca atctggccaa ggggttcaat     2640
taccatcagg accccgagtg gctgtggcct atcggctatt tcctgcgggc caagctgtac     2700
ttctccagac tgatgggccc tgagacaacc gccaagacaa tcgtgctcgt gaagaacgtg     2760
ctgagccggc actatgtgca cctggaaaga agcccctgga agggactgcc cgagctgacc     2820
aatgagaacg cccagtactg cccccttcagc tgcgaaacac aggcctggtc tatcgccacc     2880
atcctggaaa ccctgtacga cctgtga                                         2907
```

<210> SEQ ID NO 31  
<211> LENGTH: 1899

<212> TYPE: DNA
<213> ORGANISM: artificial
<220> FEATURE:
<223> OTHER INFORMATION: GDE-DY-HEAD

<400> SEQUENCE: 31

```
atgggacaca gtaaacagat tcgaatttta cttctgaacg aaatggagaa actggaaaag      60
accctcttca gacttgaaca agggtatgag ctacagttcc gattaggccc aactttacag     120
ggaaaagcag ttaccgtgta tacaaattac ccatttcctg agaaacatt  taatagagaa     180
aaattccgtt ctctggattg ggaaaatcca acagaaagag aagatgattc tgataaatac     240
tgtaaactta atctgcaaca atctggttca tttcagtatt atttccttca aggaaatgag     300
aaaagtggtg gaggttacat agttgtggac cccatttac  gtgttggtgc tgataatcat     360
gtgctaccct ggactgtgt  tactcttcag acattttag  ctaagtgttt gggacctttt     420
gatgaatggg aaagcagact tagggttgca aaagaatcag gctacaacat gattcatttt     480
accccattgc agactcttgg actatctagg tcatgctact cccttgccaa tcagttagaa     540
ttaaatcctg acttttcaag acctaataga agtatacct  ggaatgatgt tggacagcta     600
gtggaaaaat taaaaaagga atggaatgtt atttgtatta ctgatgttgt ctacaatcat     660
actgctgcta atagtaaatg gatccaggaa catccagaat gtgcctataa tcttgtaaat     720
tctccacact taaaacctgc ctgggtctta gacagagcac tttggcgttt ctcctgtgat     780
gttgcagaag ggaaatacaa agaaaaggga atacctgctt tgattgaaaa tgatcaccat     840
atgaactcca tccgaaaaat aatttgggag gatattttc  caaagcttaa actctgggaa     900
tttttccaag tagatgtcaa caaagcggtt gagcaattta aagacttct  tacacaagaa     960
aataggcgag taaccaagtc tgatccaaac caacaccta  cgattattca agatcctgaa    1020
tacagacggt ttggctgtac tgtagatatg aacattgcac taacgacttt cataccacat    1080
gacaaggggc cagcagcaat tgaagaatgc tgtaattggt tcataaaag  aatggaggaa    1140
ttaaattcag agaagcatcg actcattaac tatcatcagg aacaggcagt taattgcctt    1200
ttgggaaatg tgttttatga acgactggct ggccatggtc caaaactagg acctgtcact    1260
agaaagcatc ctttagttac caggtatttt actttcccat tgaagagat  agacttctcc    1320
atggaagaat ctatgattca tctgccaaat aaagcttgtt ttctgatggc acacaatgga    1380
tgggtaatgg gagatgatcc tcttcgaaac tttgctgaac cgggtcaga  agtttaccta    1440
aggagagaac ttatttgctg gggagacagt gttaaattac gctatgggaa taaaccagag    1500
gactgtcctt atctctgggc acacatgaaa aaatacactg aaataactgc aacttatttc    1560
cagggagtac gtcttgataa ctgccactca acacctcttc acgtagctga gtacatgttg    1620
gatgctgcta ggaatttgca acccaattta tatgtagtag ctgaactgtt cacaggaagt    1680
gaggacctag acaatgtctt tgttactaga ctgggcatta gttccttaat aagagaggca    1740
atgagtgcat ataatagtca tgaagagggc agattagttt accgatatgg aggagaacct    1800
gttggatcct tgttcagcc  ctgtttgagg cctttaatgc cagctattgc acatgccctg    1860
tttatggata ttacgcatga taatgagtgt cctattgtg                           1899
```

<210> SEQ ID NO 32
<211> LENGTH: 2700
<212> TYPE: DNA
<213> ORGANISM: artificial
<220> FEATURE:
<223> OTHER INFORMATION: GDE-DY-TAIL

```
<400> SEQUENCE: 32
catagatcag cgtatgatgc tcttccaagt actacaattg tttctatggc atgttgtgct     60
agtggaagta caagaggcta tgatgaatta gtgcctcatc agatttcagt ggtttctgaa    120
gaacggtttt acactaagtg gaatcctgaa gcattgcctt caaacacagg tgaagttaat    180
ttccaaagcg gcattattgc agccaggtgt gctatcagta aacttcatca ggagcttgga    240
gccaagggtt ttattcaggt gtatgtggat caagttgatg aagacatagt ggcagtaaca    300
agacactcac ctagcatcca tcagtctgtt gtggctgtaa ctagaactgc tttcaggaat    360
cccaagactt cattttacag caaggaagtg cctcaaatgt gcatccctgg caaaattgaa    420
gaagtagttc ttgaagctag aactattgag agaaacacga aaccttatag gaaggatgaa    480
aattcaatca atggaacacc agatatcaca gtagaaatta gagaacatat tcagcttaat    540
gaaagtaaaa ttgttaaaca agctggagtt gccacaaaag ggcccaatga atatattcaa    600
gaaatagaat ttgaaaactt gtctccagga agtgttatta tattcagagt tagtcttgat    660
ccacatgcac aagtcgctgt tggcattctt cgaaatcatc tgacacaatt cagtcctcac    720
tttaaatctg gcagcctagc tgttgacaat gcagatccta tattaaaaat tccttttgct    780
tctcttgcct atagattaac tttggctgag ctaaatcaga tcctttaccg atgtgaatca    840
gaagaaaagg aagatggtgg agggtgctat gacataccaa actggtcagc ccttaaatat    900
gcaggtcttc aaggtttaat gtctgtattg cagaaataa gaccaaagaa tgacttgggg    960 catcctttt gtaataattt gaggtctgga gattggatga ttgactatgt cagtaaccgg   1020
cttatttcac gatcaggaac tattgctgaa gttggtaaat ggttgcaggc tatgttcttc   1080
tacctgaagc agatcccacg ttaccttatc ccatgttact ttgatgctat attaattggt   1140
gcatatacca ctcttctgga tacagcatgg aagcagatgt caagctttgt tcagaatggt   1200
tcaacctttg tgaaacacct ttcattgggt tcagttcaac tgtgtggagt aggaaaattc   1260
ccttccctgc caattctttc acctgcccta atggatgtac cttataggtt aaatgagatc   1320
acaaaagaaa aggagcaatg ttgtgtttct ctagctgcag gcttacctca ttttcttct   1380 ggtatttttcc gctgctgggg aagggatact tttattgcac ttagaggtat actgctgatt   1440
actggacgct atgtagaagc caggaatatt attttagcat ttgcgggtac cctgaggcat   1500
ggtctcattc ctaatctact gggtgaagga atttatgcca gatacaattg tcggatgct   1560 gtgtggtggt ggctgcagtg tatccaggat tactgtaaaa tggttccaaa tggactagac   1620
attctcaagt gcccagtttc cagaatgtat cctacagatg attctgctcc tttgcctgct   1680
ggcacactgg atcagccatt gtttgaagtc atacaggaag caatgcaaaa acacatgcag   1740
ggcatacagt tccgagaaag gaatgctggt ccccagatag atcgaaacat gaaggacgaa   1800
ggttttaata taactgcagg agttgatgaa gaaacaggat ttgtttatgg aggaaatcgt   1860
ttcaattgtg gcacatggat ggataaaatg ggagaaagtg acagagctag aaacagagga   1920
atcccagcca caccaagaga tgggtctgct gtggaaattg tgggcctgag taaatctgct   1980
gttcgctggt tgctggaatt atccaaaaaa atatttttcc cttatcatga agtcacagta   2040
aaaagacatg gaaaggctat aaaggtctca tatgatgagt ggaacagaaa aatacaagac   2100
aactttgaaa agctatttca tgtttccgaa gacccttcag atttaaatga aaagcatcca   2160
aatctggttc acaaacgtgg catatacaaa gatagttatg gagcttcaag tccttggtgt   2220
gactatcagc tcaggcctaa ttttaccata gcaatggttg tggcccctga gctctttact   2280
acagaaaaag catggaaagc tttggagatt gcagaaaaaa aattgcttgg tccccttggc   2340
```

```
atgaaaactt tagatccaga tgatatggtt tactgtggaa tttatgacaa cgcattagac    2400
aatgacaact acaatcttgc taaaggtttc aattatcacc aaggacctga gtggctgtgg    2460
cctattgggt attttcttcg tgcaaaatta tattttccca gattgatggg cccggagact    2520
actgcaaaga ctatagtttt ggttaaaaat gttctttccc gacattatgt tcatcttgag    2580
agatcccctt ggaaaggact tccagaactg accaatgaga atgcccagta ctgtcctttc    2640
agctgtgaaa cacaagcctg gtcaattgct actattcttg agacacttta tgatttatag    2700
```

<210> SEQ ID NO 33
<211> LENGTH: 82
<212> TYPE: DNA
<213> ORGANISM: artificial
<220> FEATURE:
<223> OTHER INFORMATION: SV40 splice donor

<400> SEQUENCE: 33

```
gtaagtatca aggttacaag acaggtttaa ggagaccaat agaaactggg cttgtcgaga    60
cagagaagac tcttgcgttt ct                                            82
```

<210> SEQ ID NO 34
<211> LENGTH: 51
<212> TYPE: DNA
<213> ORGANISM: artificial
<220> FEATURE:
<223> OTHER INFORMATION: SV40 splice acceptor

<400> SEQUENCE: 34

```
gataggcacc tattggtctt actgacatcc actttgcctt tctctccaca g             51
```

<210> SEQ ID NO 35
<211> LENGTH: 612
<212> TYPE: DNA
<213> ORGANISM: artificial
<220> FEATURE:
<223> OTHER INFORMATION: E-syn promoter

<400> SEQUENCE: 35

```
cactacgggt ctaggctgcc catgtaagga ggcaaggcct ggggacaccc gagatgcctg    60
gttataatta accccaacac ctgctgcccc cccccccca acacctgctg cctgagcctg    120
agcggttacc ccaccccggt gcctgggtct taggctctgt acaccatgga ggagaagctc    180
gctctaaaaa taaccctgtc cctggtggcg cgccgagctc caccgcggtg gcggccgtcc    240
gccctcggca ccatcctcac gacacccaaa tatggcgacg ggtgaggaat ggtggggagt    300
tatttttaga gcggtgagga aggtgggcag gcagcaggtg ttggcgctct aaaaataact    360
cccgggagtt attttagag cggaggaatg gtggacaccc aaatatggcc caaatatggc    420
gacggttcct cacccgtcgc catatttggg tgtccgccct cggccggggc cgcattcctg    480
ggggccgggc ggtgctcccg cccgcctcga taaaaggctc cggggccggc ggcggcccac    540
gagctacccg gaggagcggg aggcgccaag ctctagaact agtggatccc ccgggctgca    600
ggaattcgat at                                                       612
```

<210> SEQ ID NO 36
<211> LENGTH: 4005
<212> TYPE: DNA
<213> ORGANISM: artificial
<220> FEATURE:
<223> OTHER INFORMATION: GDE HEAD max overlap

<400> SEQUENCE: 36

```
atgggacaca gtaaacagat tcgaatttta cttctgaacg aaatggagaa actggaaaag      60
accctcttca gacttgaaca agggtatgag ctacagttcc gattaggccc aactttacag     120
ggaaaagcag ttaccgtgta tacaaattac ccatttcctg agaaacatt taatagagaa      180
aaattccgtt ctctggattg ggaaaatcca acagaaagag aagatgattc tgataaatac     240
tgtaaactta atctgcaaca atctggttca tttcagtatt atttccttca aggaaatgag     300
aaaagtggtg gaggttacat agttgtggac cccattttac gtgttggtgc tgataatcat     360
gtgctaccct tggactgtgt tactcttcag acattttag ctaagtgttt gggaccttt      420
gatgaatggg aaagcagact tagggttgca aaagaatcag ctacaacat gattcatttt      480
accccattgc agactcttgg actatctagg tcatgctact cccttgccaa tcagttagaa     540
ttaaatcctg acttttcaag acctaataga agtatacct ggaatgatgt tggacagcta     600
gtggaaaaat taaaaaagga atggaatgtt atttgtatta ctgatgttgt ctacaatcat     660
actgctgcta atagtaaatg gatccaggaa catccagaat gtgcctataa tcttgtaaat     720
tctccacact taaaacctgc ctgggtctta gacagagcac tttggcgttt ctcctgtgat     780
gttgcagaag ggaaatacaa agaaaaggga ataccctgctt tgattgaaaa tgatcaccat     840
atgaactcca tccgaaaaat aatttgggag atatttttc caaagcttaa actctgggaa     900
tttttccaag tagatgtcaa caaagcggtt gagcaattta aagacttct tacacaagaa     960
aataggcgag taaccaagtc tgatccaaac caacaccta cgattattca agatcctgaa    1020
tacagacggt ttggctgtac tgtagatatg aacattgcac taacgacttt cataccacat    1080
gacaaggggc cagcagcaat tgaagaatgc tgtaattggt ttcataaaag aatggaggaa    1140
ttaaattcag agaagcatcg actcattaac tatcatcagg aacaggcagt taattgcctt    1200
ttgggaaatg tgttttatga acgactggct ggccatggtc caaaactagg acctgtcact    1260
agaaagcatc ctttagttac caggtatttt actttcccat tgaagagat agacttctcc    1320
atggaagaat ctatgattca tctgccaaat aaagcttgtt ttctgatggc acacaatgga    1380
tgggtaatgg gagatgatcc tcttcgaaac tttgctgaac cgggttcaga agtttaccta    1440
aggagagaac ttatttgctg gggagacagt gttaaattac gctatgggaa taaaccagag    1500
gactgtcctt atctctgggc acacatgaaa aaatacactg aaataactgc aacttatttc    1560
cagggagtac gtcttgataa ctgccactca acacctcttc acgtagctga gtacatgttg    1620
gatgctgcta ggaatttgca acccaattta tatgtagtag ctgaactgtt cacaggaagt    1680
gaggacctag acaatgtctt tgttactaga ctgggcatta gttccttaat aagagaggca    1740
atgagtgcat ataatagtca tgaagagggc agattagttt accgatatgg aggagaacct    1800
gttggatcct ttgttcagcc ctgtttgagg cctttaatgc cagctattgc acatgccctg    1860
tttatggata ttacgcatga taatgagtgt cctattgtgc atagatcagc gtatgatgct    1920
cttccaagta ctacaattgt ttctatggca tgttgtgcta gtggaagtac aagaggctat    1980
gatgaattag tgcctcatca gatttcagtg gtttctgaag aacggtttta cactaagtgg    2040
aatcctgaag cattgccttc aaacacaggt gaagttaatt tccaaagcgg cattattgca    2100
gccaggtgtg ctatcagtaa acttcatcag gagcttggag ccaagggttt tattcaggtg    2160
tatgtggatc aagttgatga agacatagtg gcagtaacaa gacactcacc tagcatccat    2220
cagtctgttg tggctgtaac tagaactgct ttcaggaatc ccaagacttc attttacagc    2280
aaggaagtgc ctcaaatgtg catccctggc aaaattgaag aagtagttct tgaagctaga    2340
```

-continued

```
actattgaga gaaacacgaa accttatagg aaggatgaaa attcaatcaa tggaacacca    2400
gatatcacag tagaaattag agaacatatt cagcttaatg aaagtaaaat tgttaaacaa    2460
gctggagttg ccacaaaagg gcccaatgaa tatattcaag aaatagaatt tgaaaacttg    2520
tctccaggaa gtgttattat attcagagtt agtcttgatc cacatgcaca agtcgctgtt    2580
ggcattcttc gaaatcatct gacacaattc agtcctcact ttaaatctgg cagcctagct    2640
gttgacaatg cagatcctat attaaaaatt ccttttgctt ctcttgccta tagattaact    2700
ttggctgagc taaatcagat cctttaccga tgtgaatcag aagaaaagga agatggtgga    2760
gggtgctatg acataccaaa ctggtcagcc cttaaatatg caggtcttca aggtttaatg    2820
tctgtattgg cagaaataag accaaagaat gacttggggc atccttttg taataatttg    2880 aggtctggag attggatgat tgactatgtc agtaaccggc ttatttcacg atcaggaact    2940
attgctgaag ttggtaaatg gttgcaggct atgttcttct acctgaagca gatcccacgt    3000
taccttatcc catgttactt tgatgctata ttaattggtg catataccac tcttctggat    3060
acagcatgga agcagatgtc aagctttgtt cagaatggtt caacctttgt gaaacacctt    3120
tcattgggtt cagttcaact gtgtggagta ggaaaattcc cttccctgcc aattctttca    3180
cctgccctaa tggatgtacc ttataggtta aatgagatca caaagaaaa ggagcaatgt    3240 tgtgtttctc tagctgcagg cttacctcat ttttcttctg gtattttccg ctgctgggga    3300
agggatactt ttattgcact tagaggtata ctgctgatta ctggacgcta tgtagaagcc    3360
aggaatatta tttttagcatt tgcgggtacc ctgaggcatg gtctcattcc taatctactg    3420
ggtgaaggaa tttatgccag atacaattgt cgggatgctg tgtggtggtg gctgcagtgt    3480
atccaggatt actgtaaaat ggttccaaat ggactagaca ttctcaagtg cccagtttcc    3540
agaatgtatc ctacagatga ttctgctcct ttgcctgctg gcacactgga tcagccattg    3600
tttgaagtca tacaggaagc aatgcaaaaa cacatgcagg gcatacagtt ccgagaaagg    3660
aatgctggtc cccagataga tcgaaacatg aaggacgaag gttttaatat aactgcagga    3720
gttgatgaag aaacaggatt tgtttatgga ggaaatcgtt tcaattgtgg cacatggatg    3780
gataaaatgg gagaaagtga cagagctaga acagaggaa tcccagccac accaagagat    3840
gggtctgctg tggaaattgt gggcctgagt aaatctgctg ttcgctggtt gctggaatta    3900
tccaaaaaaa atattttccc ttatcatgaa gtcacagtaa aaagacatgg aaaggctata    3960
aaggtctcat atgatgagtg gaacagaaaa atacaagaca acttt    4005
```